(12) United States Patent
Remiszewski et al.

(10) Patent No.: US 6,211,193 B1
(45) Date of Patent: Apr. 3, 2001

(54) COMPOUNDS USEFUL FOR INHIBITION OF FARNESYL PROTEIN TRANSFERASE

(75) Inventors: Stacy W. Remiszewski, Washington Township; Ronald J. Doll, Maplewood; Carmen Alvarez, Roselle Park; Tarik Lalwani, Edison, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/094,720

(22) Filed: Jun. 15, 1998

Related U.S. Application Data

(60) Provisional application No. 60/049,953, filed on Jun. 17, 1997.

(51) Int. Cl.[7] .................. A61K 31/4545; C07D 401/04; C07D 401/14; A61P 35/00
(52) U.S. Cl. ................. 514/290; 514/278; 546/19; 546/93
(58) Field of Search ............. 546/93, 19; 514/290, 514/278

(56) References Cited

U.S. PATENT DOCUMENTS

| | | | |
|---|---|---|---|
| 4,826,853 | 5/1989 | Piwinski et al. | 514/290 |
| 5,089,496 | 2/1992 | Piwinski et al. | 514/253 |
| 5,151,423 | 9/1992 | Piwinski et al. | 514/254 |
| 5,393,890 | 2/1995 | Syoji et al. | 546/80 |
| 5,661,152 | 8/1997 | Bishop et al. | 514/254 |
| 5,672,611 | 9/1997 | Doll et al. | 514/325 |
| 5,684,013 | 11/1997 | Afonso et al. | 514/290 |
| 5,696,121 | 12/1997 | Bishop et al. | 514/254 |
| 5,700,806 | 12/1997 | Doll et al. | 514/290 |
| 5,703,090 | 12/1997 | Afonso et al. | 514/290 |
| 5,712,280 | 1/1998 | Doll et al. | 514/253 |
| 5,714,609 | 2/1998 | Bishop et al. | 546/93 |
| 5,719,148 | 2/1998 | Bishop et al. | 514/228.2 |
| 5,721,236 | 2/1998 | Bishop et al. | 514/255 |
| 5,728,703 | 3/1998 | Bishop et al. | 514/254 |
| 5,852,034 | * 12/1998 | Njoroge | 514/290 |
| 5,874,442 | * 2/1999 | Doll | 514/290 |

FOREIGN PATENT DOCUMENTS

| | | |
|---|---|---|
| 0270818 | 6/1988 | (EP) . |
| 396083 | 11/1990 | (EP) . |
| WO88/03138 | 5/1988 | (WO) . |
| 0495484 | 7/1992 | (WO) . |
| WO95/10515 | 4/1995 | (WO) . |
| WO95/10516 | 4/1995 | (WO) . |
| WO95/15949 | 6/1995 | (WO) . |
| WO96/30018 | 10/1996 | (WO) . |
| WO96/30362 | 10/1996 | (WO) . |
| WO96/30363 | 10/1996 | (WO) . |
| WO96/31477 | 10/1996 | (WO) . |
| WO96/31478 | 10/1996 | (WO) . |
| WO97/23478 | 7/1997 | (WO) . |
| WO 98 11092 | 3/1998 | (WO) . |

OTHER PUBLICATIONS

Khosravi–Far R. et al. Cell Growth & Differentiation. 3, 461–469, Jul. 1992.*
Bishop et al., The Journal of Biological Chemistry, vol. 270, No. 15, pp.30611–30618 (1995).
Njoroge et al., Bioorganic & Medicinal Chemistry Letters, vol. 6, No.24, pp.2977–2982 (1996).
Njoroge et al., J. Med. Chem. 98: vol. 41 (10); pp. 1561–1567.
Mallams et al., J. Med. Chem. 98: vol. 41 (6); pp. 877–893.

* cited by examiner

*Primary Examiner*—Evelyn Mei Huang
(74) *Attorney, Agent, or Firm*—Henry C. Jeanette; Margaret M. Albanese

(57) ABSTRACT

Novel compounds of the formula:

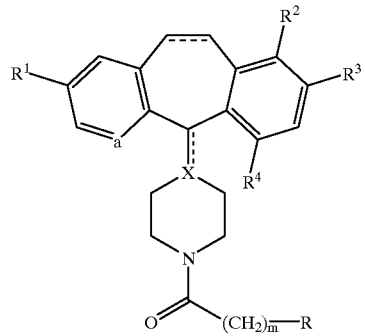

(1.0)

are disclosed. In Formula 1.0 a represents N or NO, $R^1$ and $R^3$ are halo, $R^2$ and $R^4$ are independently H or halo provided that at least one is H, X is C, CH or N, and R represents a cycloalkyl or a heterocycloalkyl ring that is substitued.

Also disclosed are methods of inhibiting farnesyl protein transferase and methods for treating tumor cells.

16 Claims, No Drawings

COMPOUNDS USEFUL FOR INHIBITION OF FARNESYL PROTEIN TRANSFERASE

This application claims the benefit of provisional application no. 60/049953, filed on Jun. 17, 1997.

BACKGROUND

WO 95/10516, published Apr. 20, 1995 discloses tricyclic compounds useful for inhibiting farnesyl protein transferase.

In view of the current interest in inhibitors of farnesyl protein transferase, a welcome. contribution to the art would be compounds useful for the inhibition of farnesyl protein transferase. Such a contribution is provided by this invention.

SUMMARY OF THE INVENTION

This invention provides compounds useful for the inhibition of farnesyl protein transferase (FPT). The compounds of this invention are represented by the formula:

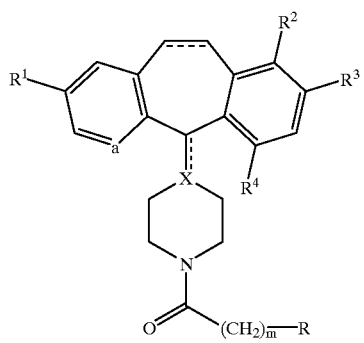

(1.0)

or a pharmaceutically acceptable salt or solvate thereof, wherein:

(A) a represents N or NO⁻;
(B) $R^1$ and $R^3$ are the same or different halo atom;
(C) $R^2$ and $R^4$ are selected from H and halo, provided that at least one of $R^2$ and $R^4$ is H;
(D) the dotted line (---) represents an optional bond;
(E) X is N, C when the optional bond to X is present, or CH when the optional bond to X is absent;
(F) m is 0, 1 or 2;
(G) R represents:
  1. a cycloalkyl ring selected from:

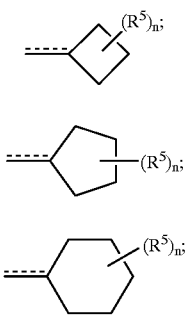

2.0

3.0

4.0

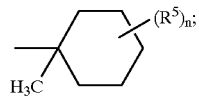

5.0

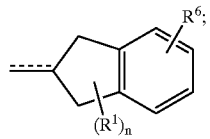

6.0

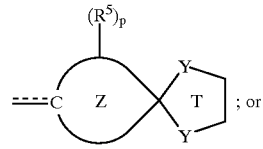

7.0

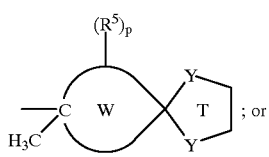

8.0

2. a heterocycloalkyl ring selected from:

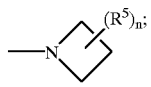

9.0

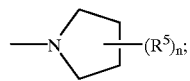

10.0

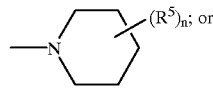

11.0

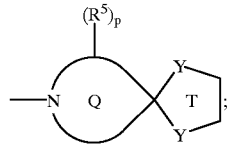

12.0

(H) p is 0, 1 or 2;
(I) when n or p is 1 then $R^5$ is selected from:
  (1) =O, with the proviso that when R is heterocycloalkyl Ring 10.0 and m is 0, 1 or 2 then the =O group is not bound to a carbon that is adjacent to the ring nitrogen, and with the proviso that when R is heterocycloalkyl Ring 11.0 and m is 1 or 2 then the =O group is not bound to a carbon that is adjacent to the ring nitrogen;
  (2) =N—OH;
  (3) =N—OR⁷ wherein $R^7$ represents a $C_1$ to $C_6$ alkyl group;
  (4) =N—N(H)—C(O)—R⁸ wherein $R^8$ represents —NH₂ or $C_1$ to $C_6$ alkyl;
  (5) =N—O—(CH₂)ᵣ—C(O)—R¹¹ wherein r is 1, 2, or 3, and $R^{11}$ is selected from: —OH, —O-alkyl or —NH₂;

(6) =N—O—(CH$_2$)$_s$—O—R$^{12}$, wherein s is 2, 3, or 4 and R$^{12}$ is selected from: H, alkyl or trialkylsilyl (e.g., Si(CH$_3$)$_2$—C(CH$_3$)$_3$);

(7) —NR$^{13}$R$^{14}$ wherein R$^{13}$ and R$^{14}$ are independently selected from:
(a) H;
(b) acyl;
(c) alkyl;
(d) aralkyl;
(d) cycloalkyl;
(e) heterocycloalkyl;
(f) heteroaralkyl;
(g) —S(O)$_2$R$^{15}$ wherein R$^{15}$ is C$_1$ to C$_6$ alkyl or aryl; or
(h) an aralkyl, cycloalkyl, heterocycloalkyl, heteroaryl or heteroaralkyl having from 1 to 3 substituents selected from: =O, halo, —OH or —O-alkyl, wherein said substiuents being bound to substitutable ring carbons; or (8) OR$^{16}$ wherein R$^{16}$ is selected from:
(a) H;
(b) C$_1$ to C$_6$ alkyl;
(c) —C(O)R$^{17}$ wherein R$^{17}$ is selected from: alkyl, aryl, heteroaryl or aralkyl; or
(d) —C(O)NHR$^{18}$ wherein R$^{18}$ is selected from: H, —C(O)R$^{19}$ wherein R$^{19}$ is selected from: —C(Cl)$_3$, alkyl or —(CH$_2$)$_2$OH;

(J) when n or p is 2, then each R$^5$ is the same or different and each R$^5$ is selected from:
(1) —NR$^{13}$R$^{14}$ wherein R$^{13}$ and R$^{14}$ are independently selected from:
(a) H;
(b) acyl;
(c) alkyl;
(d) aralkyl;
(d) cycloalkyl;
(e) heterocycloalkyl;
(f) heteroaralkyl;
(g) —S(O)$_2$R$^{15}$ wherein R$^{15}$ is C$_1$ to C$_6$ alkyl or aryl; or
(h) an aralkyl, cycloalkyl, heterocycloalkyl, heteroaryl or heteroaralkyl having from 1 to 3 substituents selected from: =O, halo, —OH or —O-alkyl, wherein said substiuents being bound to substitutable ring carbons; or;

(2) OR$^{16}$ wherein R$^{16}$ is selected from:
(a) H;
(b) C$_1$ to C$_6$ alkyl;
(c) —C(O)R$^{17}$ wherein R$^{17}$ is selected from: alkyl, aryl, heteroaryl or aralkyl; or
(d) —C(O)NHR$^{18}$ wherein R$^{18}$ is selected from: H, —C(O)R$^{19}$ wherein R$^{19}$ is selected from: —C(Cl)$_3$, alkyl or —(CH$_2$)$_2$OH; or (K) provided that R$^1$ is not bound to a carbon atom adjacent to the nitrogen atom in Rings 9.0, 10.0, 11.0 or 12.0;

(L) Y is selected from O or S, provided that each Y is the same;

(M) Z represents the remainder of cycloalkyl Rings 2.0, 3.0 or 4.0, such that spiro ring T is bound to one of the carbon atoms in said cycloalkyl ring;

(N) W represents the remainder of cycloalkyl Ring 5.0, such that spiro ring T is bound to one of the carbon atoms in said cycloalkyl ring;

(O) Q represents the remainder of heterocycloalkyl Rings 9.0, 10.0 or 11.0, such that spiro ring T is bound to one of the carbon atoms in said heterocycloalkyl ring, provided that spiro Ring T is not bound to a carbon atom adjacent to the nitrogen atom; and (P) R$^6$ is selected from: alkoxy, alkyl or —OH.

The compounds of this invention: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

The compounds of this invention inhibit farnesyl protein transferase and the farnesylation of the oncogene protein Ras. Thus, this invention further provides a method of inhibiting farnesyl protein transferase, (e.g., ras farnesyl protein transferase) in mammals, especially humans, by the administration of an effective amount of the tricyclic compounds described above. The administration of the compounds of this invention to patients, to inhibit farnesyl protein transferase, is useful in the treatment of the cancers described below.

This invention provides a method for inhibiting or treating the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention also provides a method for inhibiting or treating tumor growth by administering an effective amount of the tricyclic compounds, described herein, to a mammal (e.g., a human) in need of such treatment. In particular, this invention provides a method for inhibiting or treating the growth of tumors expressing an activated Ras oncogene by the administration of an effective amount of the above described compounds. Examples of tumors which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma, epidermal carcinoma, breast cancer and prostate cancer.

It is believed that this invention also provides a method for inhibiting or treating proliferative diseases, both benign and malignant, wherein Ras proteins are aberrantly activated as a result of oncogenic mutation in other genes—i.e., the Ras gene itself is not activated by mutation to an oncogenic form—with said inhibition or treatment being accomplished by the administration of an effective amount of the tricyclic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited or treated by the tricyclic compounds described herein.

The tricyclic compounds useful in the methods of this invention inhibit or treat the abnormal growth of cells.

Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

DETAILED DESCRIPTION OF THE INVENTION

As used herein, the following terms are used as defined below unless otherwise indicated:

BOC-represents tert-butyloxycarbonyl;

CBZ-represents benzyloxycarbonyl;

Et (or ET)-represents ethyl ($C_2H_5$);

MH+-represents the molecular ion plus hydrogen of the molecule in the mass spectrum;

acyl-represents a G—C(O)— group wherein G represents alkyl, aryl, heteroaryl, cycloalkyl, heterocycloalkyl, —O-alkyl, —O— aryl, or $NR^{100}R^{200}$ wherein $R^{100}$ and $R^{200}$ are independently selected from alkyl or aryl;

alkyl-represents straight and branched carbon chains and contains from one to twenty carbon atoms, preferably one to six carbon atoms;

aralkyl-represents an alkyl group, as defined above, substituted with an aryl, as defined below, such that the bond from another substituent is to the alkyl moiety;

aryl-(including the aryl portion of aryloxy and aralkyl)- represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted (e.g., 1 to 3) with one or more of halo, alkyl, hydroxy, alkoxy, phenoxy, $CF_3$, amino, alkylamino, dialkylamino, —$COOR^{300}$ or —$NO_2$, wherein $R^{300}$ represents alkyl or aryl; and cycloalkyl-represents saturated carbocyclic rings branched or unbranched of from 3 to 20 carbon atoms, preferably 3 to 7 carbon atoms;

halo-represents fluoro, chloro, bromo and iodo;

heteroaralkyl-represents and alkyl group, as defined above, substitued with a heteroaryl group, as defined below, such that the bond from another substituent is to the alkyl moiety;

heteroaryl-represents cyclic groups, optionally substituted with $R^3$ and $R^4$, having at least one heteroatom selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms, e.g., triazolyl, 2-, 3- or 4-pyridyl or pyridyl N-oxide (optionally substituted with $R^3$ and $R^4$), wherein pyridyl N-oxide can be represented as:

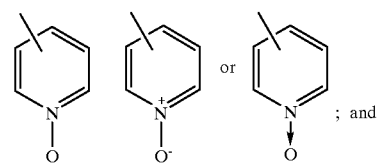

; and heterocycloalkyl-represents a saturated, branched or unbranched carbocylic ring containing from 3 to 15 carbon atoms, preferably from 4 to 6 carbon atoms, which carbocyclic ring is interrupted by 1 to 3 hetero groups selected from —O—, —S— or —$NR^{400}$, wherein $R^{400}$ represents alkyl, aryl or acyl-(suitable heterocycloalkyl groups including 2- or 3-tetrahydrofuranyl, 2- or 3-tetrahydrothienyl, 2-, 3- or 4-piperidinyl, 2- or 3-pyrrolidinyl, 2- or 3-piperizinyl, 2- or 4-dioxanyl, etc.).

The following solvents and reagents are referred to herein by the abbreviations indicated: ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxybenzotriazole (HOBT); 1-(3-dimethylaminopropyl)-3-ethyl carbodiimide hydrochloride (DEC); diisobutylaluminum hydride(DIBAL); and 4-methylmorpholine (NMM).

The positions in the tricyclic ring system are:

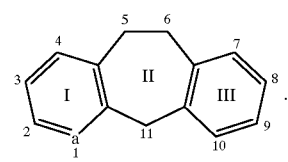

Preferred halo atoms for $R^1$, $R^2$, $R^3$, and $R^4$ in Formula 1.0 are selected from: Br, Cl or I, with Br and Cl being preferred.

Compounds of Formula 1.0 include compounds of Formulas 1.1 and 1.2:

(1.1)
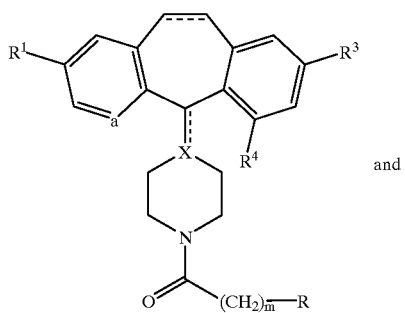

and (1.2)
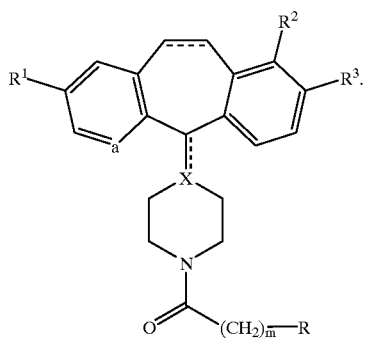

wherein $R^1$, $R^3$ and $R^4$ in Formula 1.1 are halo, and $R^1$, $R^2$ and $R^3$ in Formula 1.2 are halo. Compounds of Formula 1.1 are preferred.

Preferably, in Formula 1.1, $R^1$ is Br, $R^3$ is Cl, and $R^4$ is halo. More preferably, in Formula 1.1, $R^1$ is Br, $R^3$ is Cl, and $R^4$ is Br.

Preferably, in Formula 1.2, $R^1$ is Br, $R^2$ is halo, and $R^3$ is Cl. More preferably, in Formula 1.2, $R^1$ is Br, $R^2$ is Br, and $R^3$ is Cl.

Preferably, for compounds of Formulas 1.1 and 1.2, X is CH or N. For compounds of Formula 1.1, X is preferably CH.

Preferably, for the compounds of this invention, the optional bond between positions 5 and 6 (i.e., C5–C6) in the tricyclic system is absent.

Also, preferably, for the compounds of this invention, substituent a in Ring I represents N.

Those skilled in the art will appreciate that compounds of Formula 1.0 include compounds of Formulas 1.3 and 1.4:

(1.3)
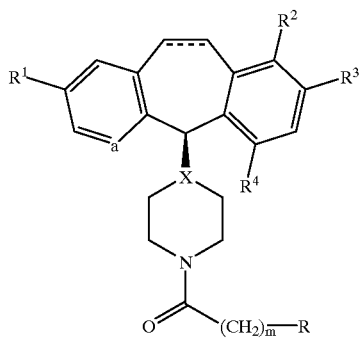

(1.4)
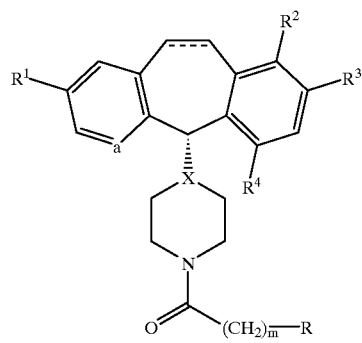

wherein X is CH or N, with compounds of 1.3 being preferred for compounds of Formula 1.1, and with compounds of Formula 1.4 being preferred for compounds of Formula 1.2.

Thus, compounds of the invention include compounds of the formulas:

(1.5)
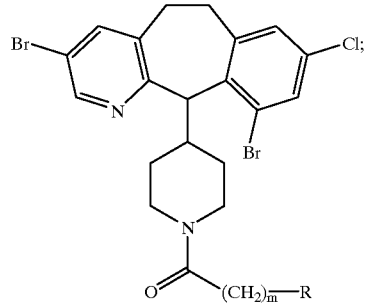

(1.6)
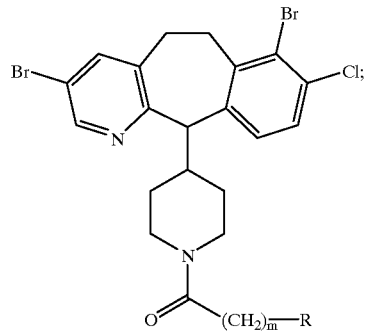

(1.7)
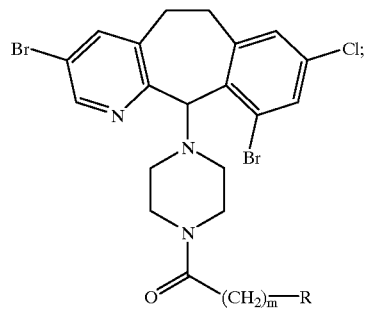

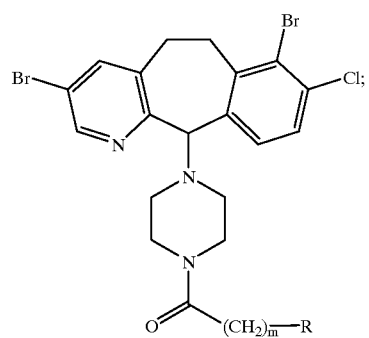
(1.8)
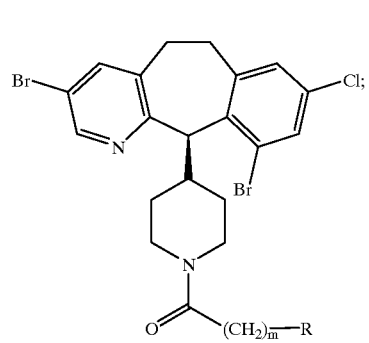
(1.9)
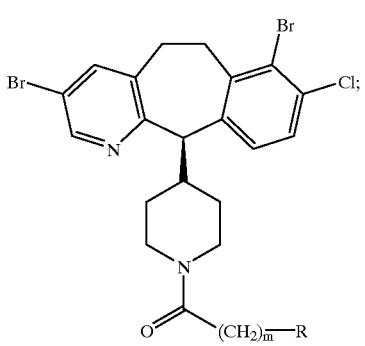
(1.10)
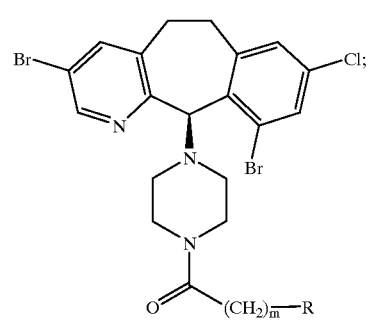
(1.11)
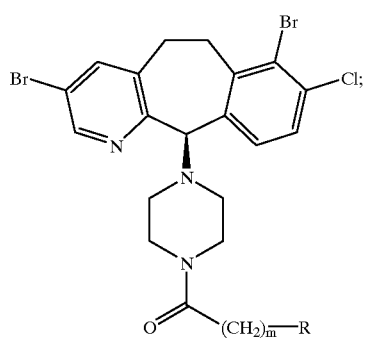
(1.12)
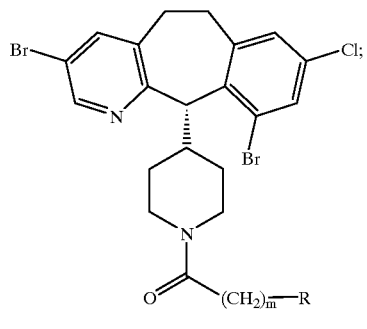
(1.13)
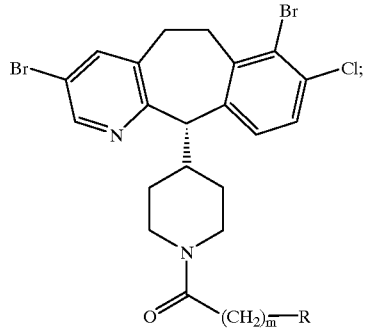
(1.14)
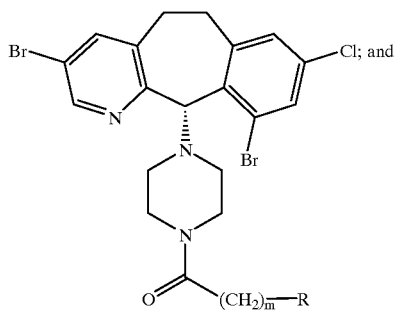
(1.15)

(1.16)

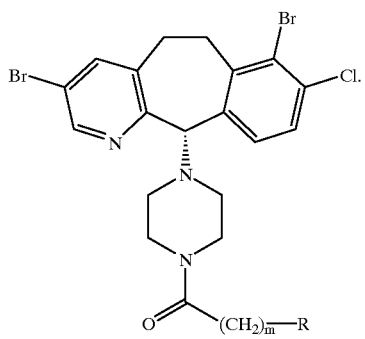

Compounds of Formula 1.9 are preferred.

Preferred cycloalkyl rings for substituent R are:

4.0

5.0
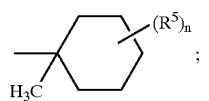

6.0
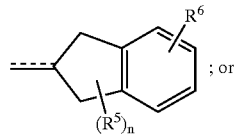

7.0
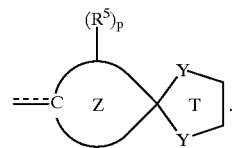

More preferred cycloalkyl rings for substituent R are:

4.0
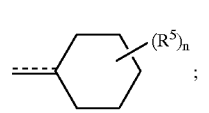

6.0
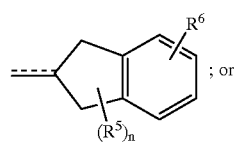

7.0
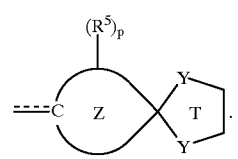

Most preferred cycloalkyl rings for substituent R is:

4.0
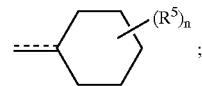

Preferably, the optional bond is absent in Formulas 2.0, 3.0, 4.0. 6.0 and 7.0. Also, preferably, for Ring 6.0, $R^6$ is —OCH$_3$.

Preferably, spiro Ring 7.0 is 7.1
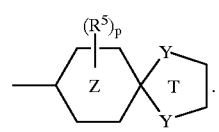

Most preferably, spiro Ring 7.0 is:

7.2
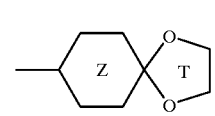

Preferred heterocycloalkyl rings for substituent R are 11.0
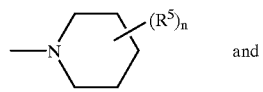 and 12.0
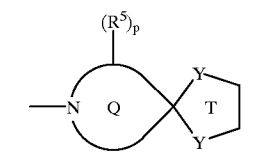

Preferably p is 0.

Preferably, R is a cycloalkyl ring, and more preferably R is cycloalkyl Ring 4.0. Preferably, when n is 1, $R^5$ is at the 4-position, i.e, preferably R is:

4.1

When R is a heterocycloalkyl ring, and when n is 1, then $R^5$ is preferably at the 4-position, i.e., R is 11.1
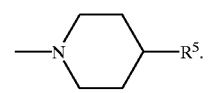

Preferably, when n is 1, $R^5$ is selected from: =O, =N—OH, =N—OCH$_3$, =N—NH—C(O)—NH$_2$, =N—NH—C(O)—CH$_3$, =N—O—CH$_2$—C(O)—OH, =N—O—(CH$_2$)$_2$—O—Si(CH$_3$)$_2$—C(CH$_3$)$_3$, —NHSO$_2$CH$_3$, —NH$_2$, —NHC(O)C(O)OC$_2$H$_5$, —NHC (O)NH$_2$, —NHC(O)OC(CH$_3$)$_3$, —NHC(O)C(O)NH$_2$, —OC(O)CH$_3$, or —OH.

More preferably, when n is 1, R$^5$ is selected from: =O, =N—OH, =N—OCH$_3$, =N—NH—C(O)—NH$_2$, =N—NH—C(O)—CH$_3$, =N—O—CH$_2$—C(O)—OH, or —OC(O)CH$_3$.

Those skilled in the art will recognize that the representative compounds listed below also serve to illustrate representative substituents for R, and hence R$^5$ in Formula 1.0.

Representative compounds of the invention include:

(13.0)

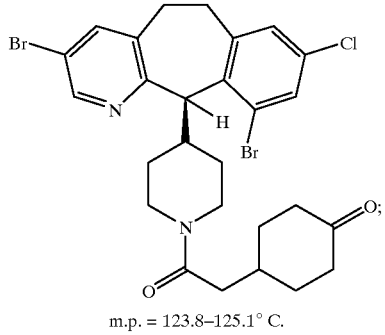

m.p. = 123.8–125.1° C.

(14.0)

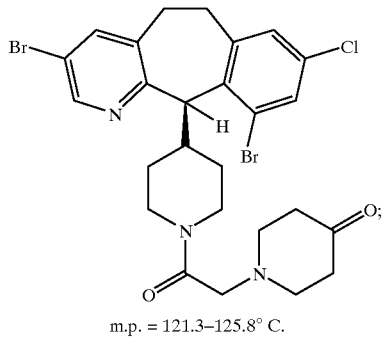

m.p. = 121.3–125.8° C.

(16.0)

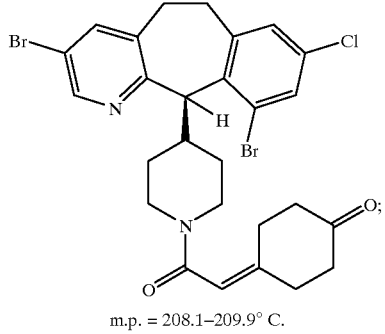

m.p. = 208.1–209.9° C.

(17.0A)

(Isomer A)

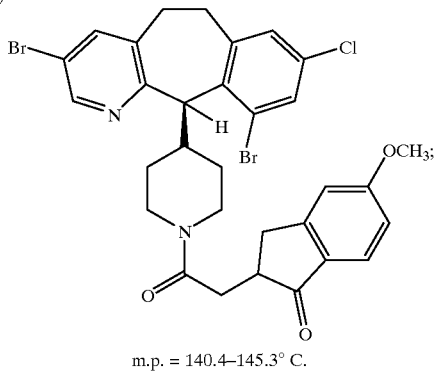

m.p. = 140.4–145.3° C.

(17.0B)

(Isomer B)

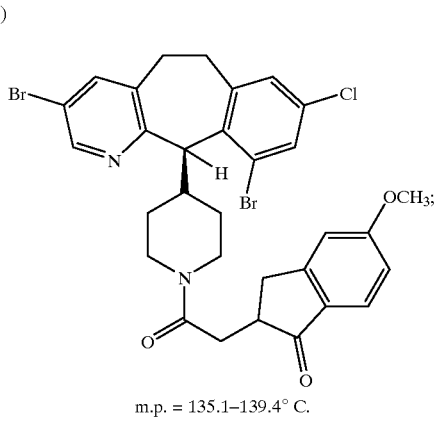

m.p. = 135.1–139.4° C.

(18.0)

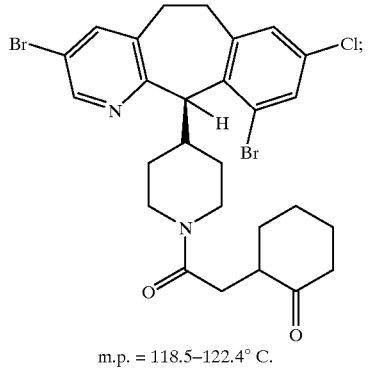

m.p. = 118.5–122.4° C.

(19.0)

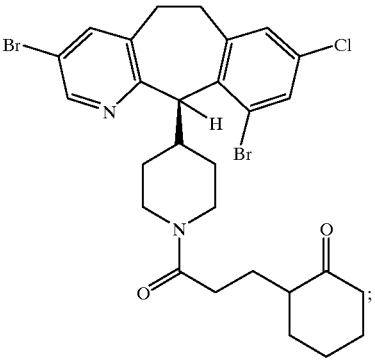

m.p. = 110.5–114.8° C.

(20.0)
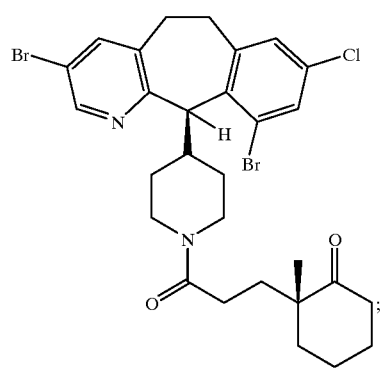
m.p. = 113.5–116.8° C.
(21.0)
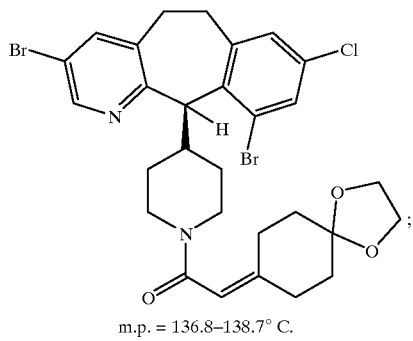
m.p. = 136.8–138.7° C.
(22.0)
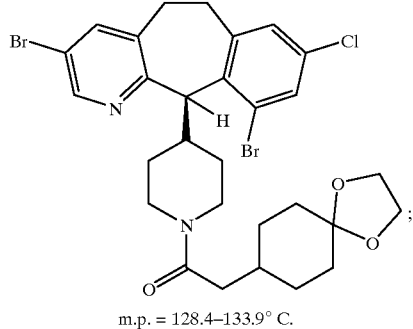
m.p. = 128.4–133.9° C.
(23.0)
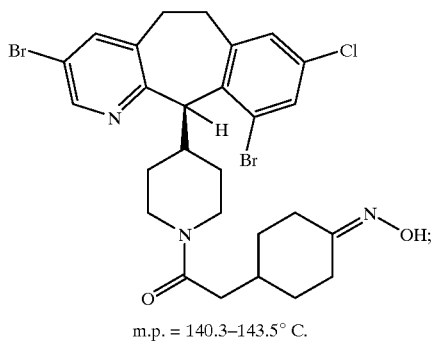
m.p. = 140.3–143.5° C.
(24.0)
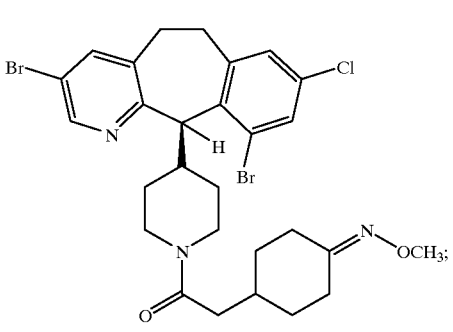
m.p. = 128.4–133.9° C.
(25.0)
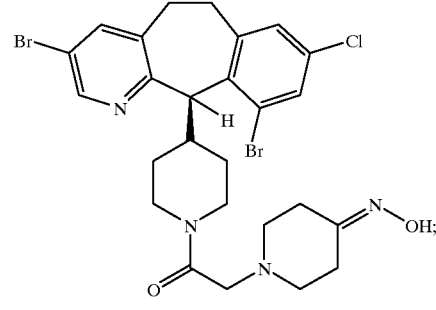
m.p. = 102.1–105.4° C.
(26.0)
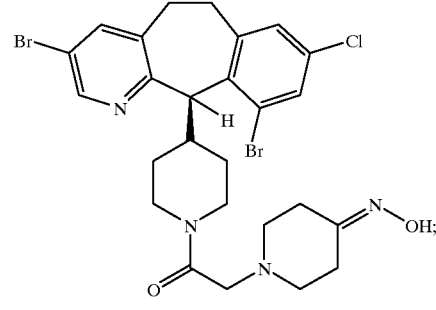
m.p. = 147.2–152.2° C.
(27.0)
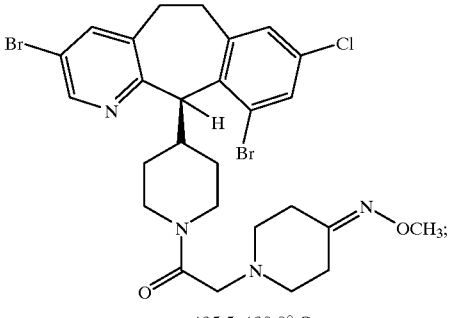
m.p. = 105.5–108.8° C.

(28.0)
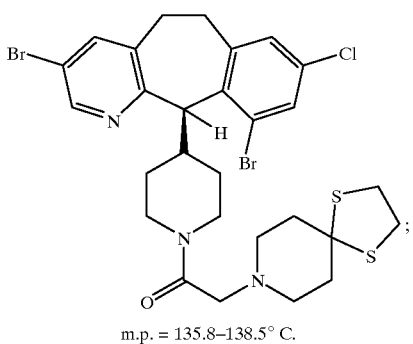
m.p. = 135.8–138.5° C.
(29.0)
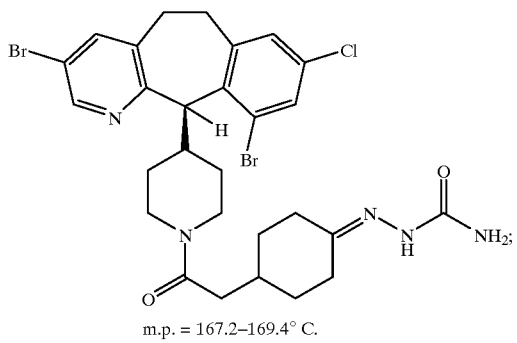
m.p. = 167.2–169.4° C.
(30.0)
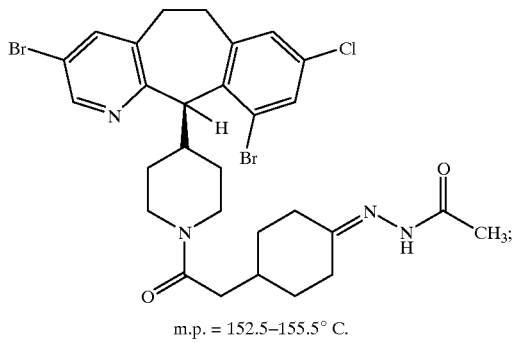
m.p. = 152.5–155.5° C.
(31.0)
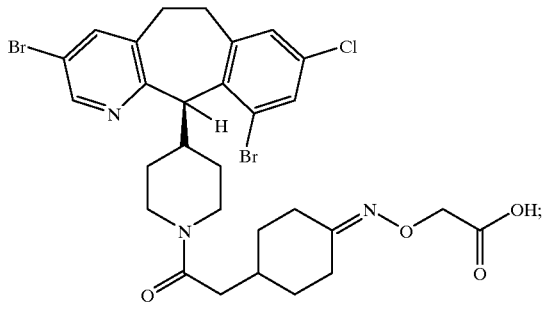
m.p. = 95.7–97.3° C.
(32.0)
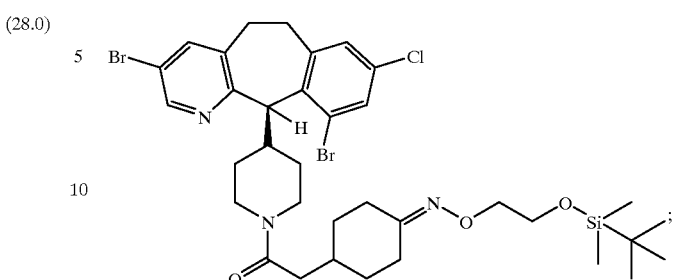
m.p. = 87.2–90.3° C.
(33.0)
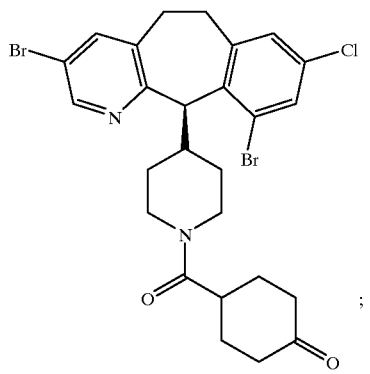
m.p. = 125.4–127.7° C.
(34.0)
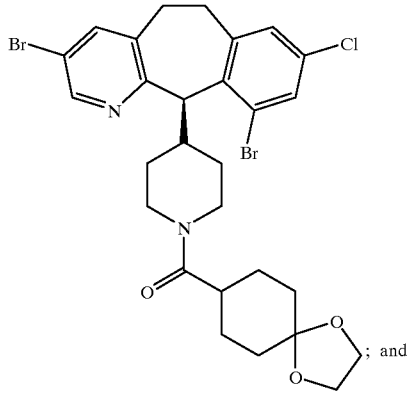
; and
m.p. = 119.3–121.6° C.
(35.0)
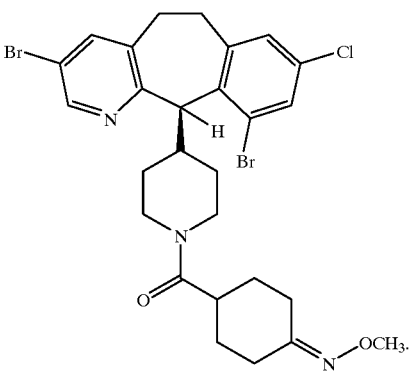
m.p. = 120.4–123.8° C.

Compounds of Formula 1.0 include compounds of the formula:

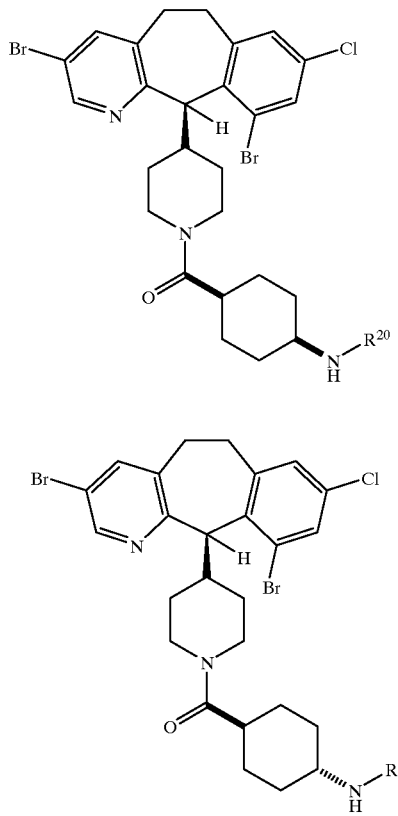

wherein $R^{20}$ is selected from the substituents listed in Table 1:

TABLE 1

| Compound | $R^{20}$ |
|---|---|
| 36.0 | ![](acetate with C(CH₃)₃) |
| 37.0 | H |
| 38.0 | ![](acetamide NH₂) |
| 39.0 | ![](pyruvate OC₂H₅) |
| 40.0 | —SO₂CH₃ |

TABLE 1-continued

| Compound | $R^{20}$ |
|---|---|
| 41.0 | ![](acetyl imidazolidinone) |
| 42.0 | |
| 42.1 | ![](pyruvamide NH₂) |
| 42.2 | ![](benzyl ester) |
| | — — |

Compounds of Formula 1.0 also include compounds of the formula:

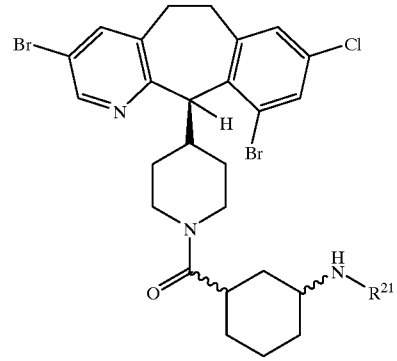

wherein $R^{21}$ is selected from the substituents listed in Table 2:

TABLE 2

| Compound | $R^{21}$ |
|---|---|
| 43.0 | ![](acetate with C(CH₃)₃) |
| 44.0 | H |

TABLE 2-continued
| Compound | R[21] |
|---|---|
| 45.0 | —CH₂C(O)NH₂ |
| 46.0 | —C(O)C(O)OC₂H₅ |
| 47.0 | 4-oxocyclohexyl-C(O)— |
| 48.0 | —SO₂CH₃ |
| 49.0 | —CH₂C₆H₅ |
| 49.1 | —C(O)C(O)NH₂ |
| 49.2 | —C(O)OCH₂C₆H₅ |
| — | — |
Compounds of Formula 1.0 also include compounds of the formula:
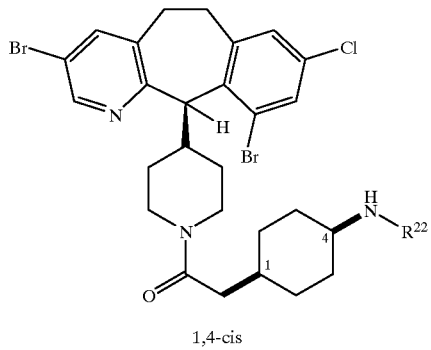
1,4-cis
or
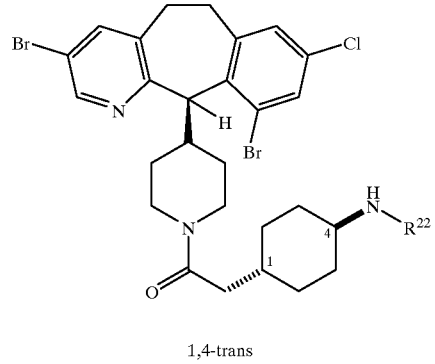
1,4-trans
wherein R[22] is selected from the substituents in Table 3:
TABLE 3
| Compound | R[22] |
|---|---|
| 50.0 | —C(O)CH₂OC(CH₃)₃ (cis) |
| 51.0 | H (cis) |
| 52.0 | —C(O)CH₂OC(CH₃)₃ (trans) |
| 53.0 | H (trans) |
| 54.0 | —C(O)CH₂NH₂ (cis) |
| 55.0 | —C(O)CH₂NH₂ (trans) |
| 56.0 | —C(O)C(O)OC₂H₅ (cis) |
| 57.0 | —C(O)C(O)OC₂H₅ (trans) |

TABLE 3-continued
| Compound | R²² |
|---|---|
| 58.0 | imidazolidinone-acetyl (cis) |
| 59.0 | imidazolidinone-acetyl (trans) |
| 60.0 | –SO₂CH₃ (cis) |
| 61.0 | –SO₂CH₃ (cis) |
| 62.0 | benzyl (cis) |
| 63.0 | benzyl (trans) |
Compounds of formula 1.0 also include compounds of the formula:
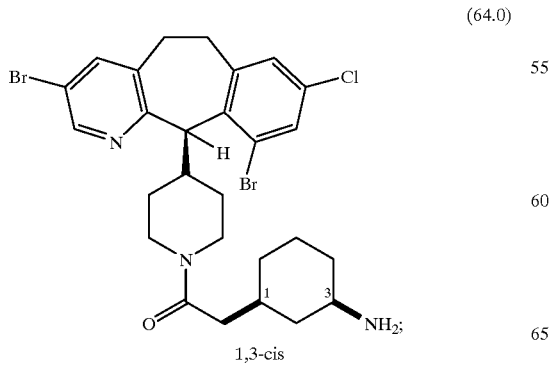
Compounds of Formula 1.0 also include compounds of the formula:
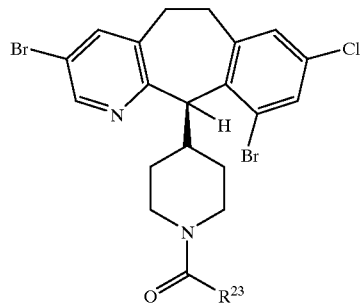

wherein $R^{23}$ is selected form the substituents in Table 4:

TABLE 4

| Compound | $R^{23}$ |
|---|---|
| 68.0 | (4-hydroxycyclohexyl, trans) |
| 69.0 | (4-acetoxycyclohexyl, trans, OC(O)CH₃) |
| 70.0 | (4-hydroxycyclohexyl, cis) |
| 71.0 | (3-hydroxy-1-methylcyclohexyl) (1,3-cis) |
| 72.0 | (3-hydroxy-1-methylcyclohexyl) (1,3-trans) |
| 73.0 | (1R,3S)-3-hydroxy-1-methylcyclohexyl |
| 74.0 | (1S,3R)-3-hydroxy-1-methylcyclohexyl |
| 75.0 | (1R,3R)-3-hydroxy-1-methylcyclohexyl |
| 76.0 | (1S,3S)-3-hydroxy-1-methylcyclohexyl |
| 77.0 | 3,4-dihydroxy-1-methylcyclohexyl (e.g., 1,3-cis, 1,4-trans, 3,4-trans, 1,3-trans, 1,4-cis, and 3,4-cis) |
| 78.0 | 3,5-dihydroxy-1-methylcyclohexyl (e.g., 1,3-cis, 1,5-cis, 3,5-cis, 1,3-trans, 1,5-trans, and 3,4-trans) |

TABLE 4-continued

| Compound | $R^{23}$ |
|---|---|
| 79.0 | (4-methoxycyclohexyl, trans) |
| 80.0 | (4-methoxycyclohexyl, cis) |
| 81.0 | (3-methoxy-1-methylcyclohexyl) (1,3-cis) |
| 82.0 | (3-methoxy-1-methylcyclohexyl) (1,3-trans) |
| 83.0 | (1R,3S)-3-methoxy-1-methylcyclohexyl |
| 84.0 | (1S,3R)-3-methoxy-1-methylcyclohexyl |
| 85.0 | (1R,3R)-3-methoxy-1-methylcyclohexyl |
| 86.0 | (1S,3S)-3-methoxy-1-methylcyclohexyl |
| 87.0 | 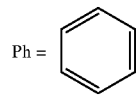 |
| | $Ph =$ (phenyl ring) |
| 88.0 | 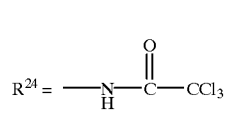 |
| | $R^{24} = -\underset{H}{N}-\overset{O}{\underset{\|}{C}}-CCl_3$ |

TABLE 4-continued
| Compound | R²³ |
|---|---|
| 89.0 | 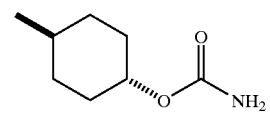 |
| 90.0 | 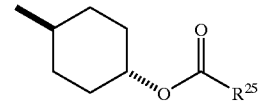<br>R²⁵ = 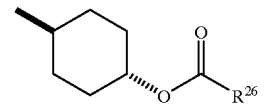 |
| 91.0 | 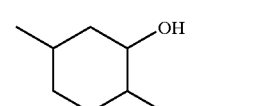<br>R²⁶ = —NH(CH₂)₂OH |
| 92.0 | 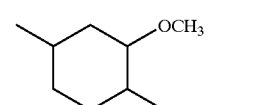 |
| 93.0 | 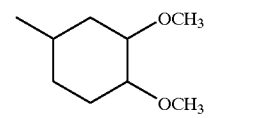 |
| 94.0 | 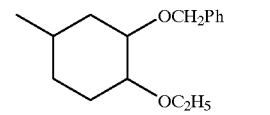 |
| 95.0 | 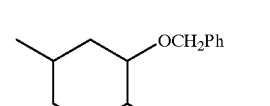<br>Ph = phenyl |
| 96.0 | 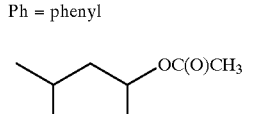<br>Ph = phenyl |
| 97.0 | 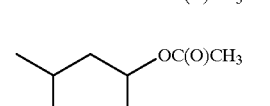 |
| 98.0 | 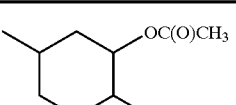 |
| 99.0 | 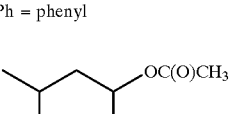<br>Ph = phenyl |
| 100.0 | 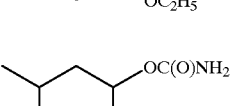 |
| 101.0 | 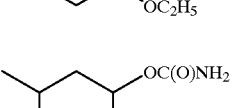 |
| 102.0 | 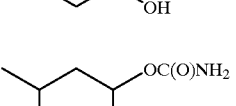 |
| 103.0 | 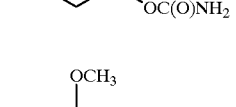 |
| 104.0 | 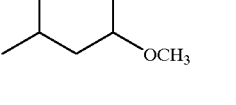 |
| 105.0 | 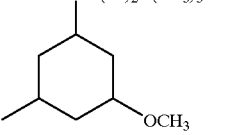<br>Ph = phenyl |
| 106.0 | 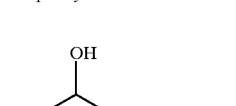 |
| 107.0 | 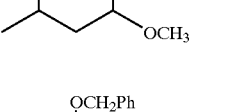<br>Ph = phenyl |

TABLE 4-continued

| Compound | R²³ |
|---|---|
| 108.0 | cyclohexane with OC(O)CH₃ and OC(O)CH₃ substituents and a methyl |
| 109.0 | cyclohexane with OSi(Ph)₂C(CH₃)₃ and OH substituents and a methyl; Ph = phenyl |
| 110.0 | cyclohexane with OSi(Ph)₂C(CH₃)₃ and OC(O)CH₃ substituents and a methyl; Ph = phenyl |
| 111.0 | cyclohexane with OH and OC(O)CH₃ substituents and a methyl; Ph = phenyl |
| 112.0 | cyclohexane with OC(O)Ph and OC(O)CH₃ substituents and a methyl; Ph = phenyl |
| 113.0 | cyclohexane with OC(O)CH₃ and OCH₃ substituents and a methyl |
| 114.0 | cyclohexane with OC(O)NH₂ and OCH₃ substituents and a methyl |
| 115.0 | cyclohexane with OC(O)NH₂ and OH substituents and a methyl |
| 116.0 | cyclohexane with OC(O)NH₂ and OC(O)NH₂ substituents and a methyl |

Lines drawn into the ring systems indicate that the indicated bond may be attached to any of the substitutable ring carbon atoms.

Certain compounds of the invention may exist in different isomeric (e.g., enantiomers, diastereoisomers, atropisomers) forms. The invention contemplates all such isomers both in pure form and in admixture, including racemic mixtures. Enol forms are also included.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds of the invention may be prepared according to the procedures described in WO 95/10516 published Apr. 20, 1995, U.S. Pat. No. 5,719,148 issued Feb. 17, 1998, and copending application Ser. No. 08/766,601 filed Dec. 12, 1996; the disclosures of each being incorporated herein by reference thereto; and according to the procedures described below.

Compounds of the invention can be prepared according to the reaction:

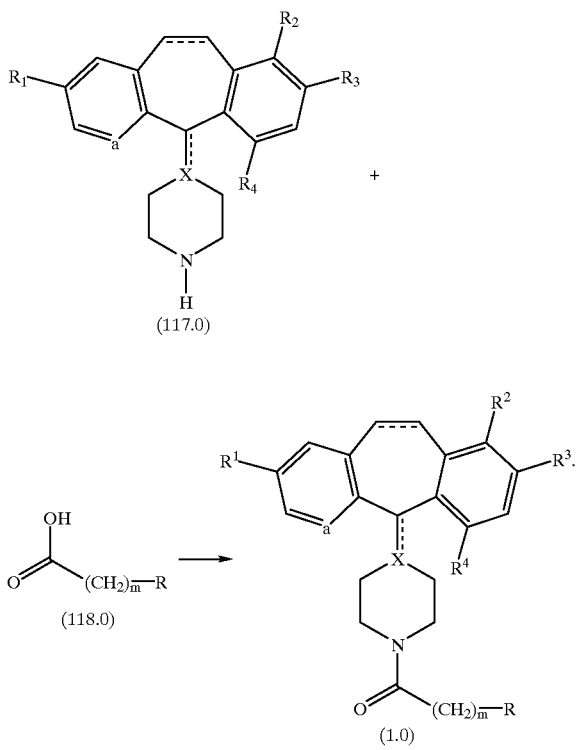

In the reaction, the keto acid, ketal acid, oxime acid or hydrazone carboxylic acid (118.0) is coupled to the tricyclic amine (117.0) using amide bond forming conditions well known to those skilled in the art. The substituents are as defined for Formula 1.0. For example, carbodiimide coupling methods (e.g., DEC) can be used. For example, the carboxylic acid (118.0) can be reacted with the tricyclic amine (117.0) using DEC/HOBT/-NMM in DMF at about 25° C. for a sufficient period of time, e.g., about 18 hours, to produce a compound of Formula 1.0.

For example, using the carbodiimide coupling methods, compounds of the invention can be produced according to the reaction:

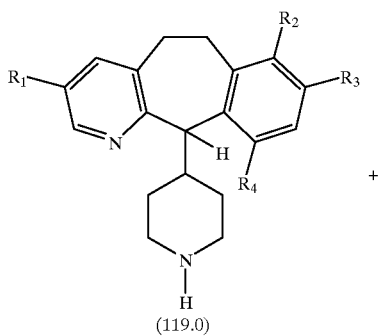

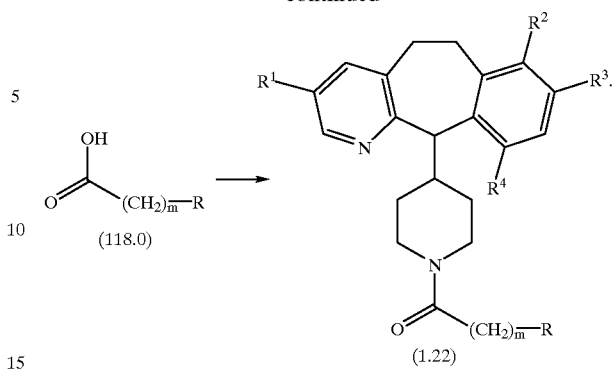

The keto acids, ketal acids, oxime acids or hydrazone acids (118.0) are either commercially available or can be prepared by methods well known in the art. In many cases the corresponding ketoesters, ketal esters, oxime esters or hydrazone esters, which can be hydrolyzed to the corresponding acids, are either commercially available or can be prepared by methods well known in the art. The keto, ketal, oxime and hydrazone groups in the intermediate (118.0), or in the product (1.22) can be interconverted by methods well known in the art.

Compounds of Formula 1.0 wherein m is 0 and R is

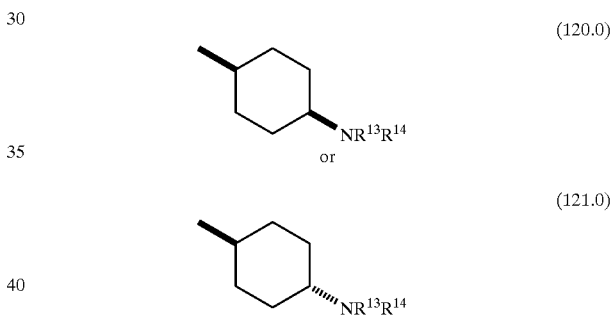

can be prepared by reaction of the corresponding carboxylic acid:

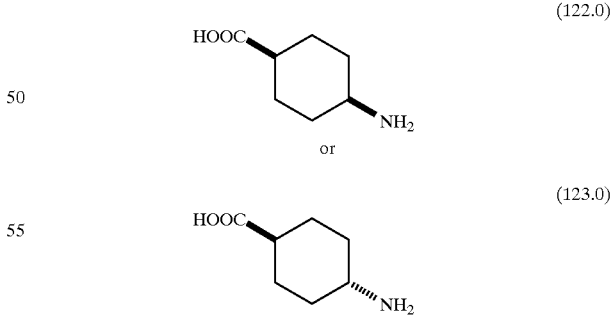

with a tricyclic amine of Formula 117.0. Carboxylic acids 122.0 and 123.0 can be prepared according to the procedure described in *J. Med. Chem.* 1993, 36, 1100. The N atom of 122.0 and 123.0 can be protected with a suitable protecting group, e.g., t-butoxycarbonyl (BOC), by techniques well known to those skilled in the art to provide intermediate acids 124.0 or 125.0:

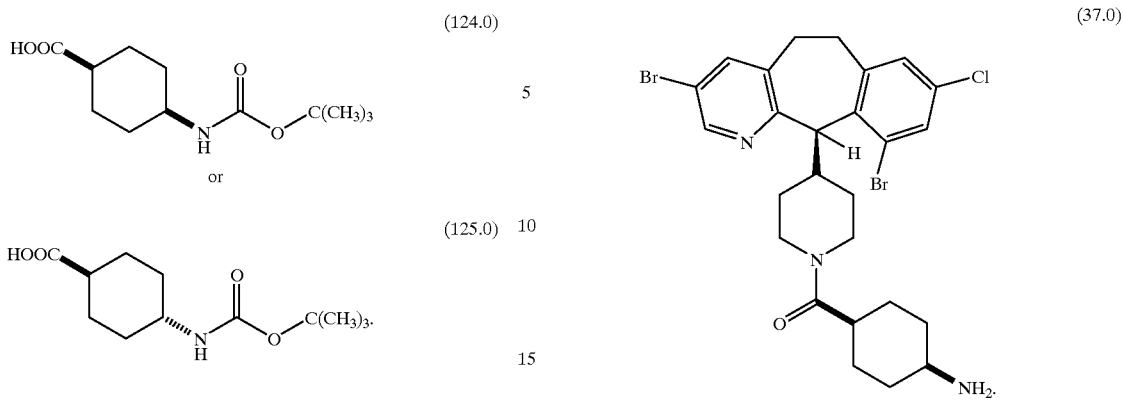

(124.0)

or (125.0)

The tricyclic amine of Formula 117.0 (e.g., Formula 119.0), is reacted with the N-protected 4-aminocyclohexanecarboxylic acid (124.0 or 125.0), a dehydrating agent (e.g., 1-(3-dimethylaminopropyl)-3-ethylcarbodiimide hydrochloride (DEC•HCl)), a catalyst (e.g., 1-hydroxy-benzotriazole hydrate (HOBT•H$_2$O)) and a base (e.g., N-methyl-morpholine (NMM)) in a suitable solvent (e.g., DMF) to give a compound of Formula 1.0.

For example,

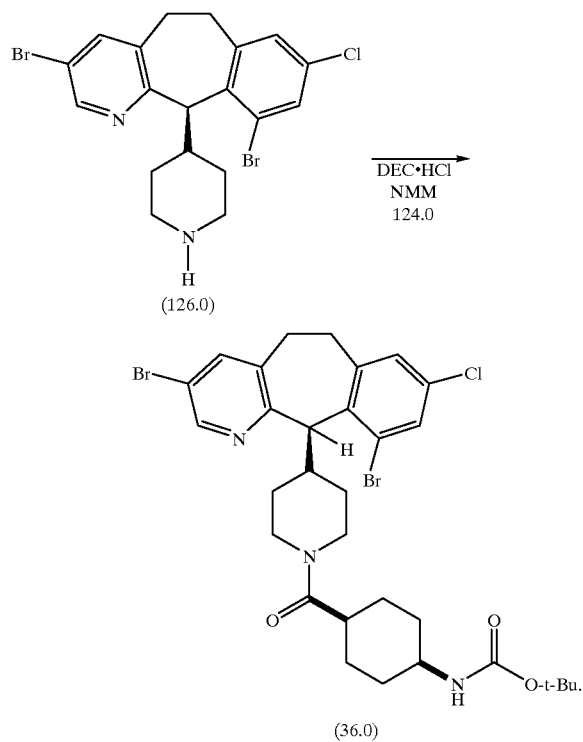

(126.0)

DEC•HCl
NMM
124.0

(36.0)

The BOC group (—C(O)O-t-Bu) can be removed by techniques known in the art to obtain another compound of the invention. For example, reaction of Formula 36.0 with trifluoroacetic acid (TFA) in a suitable solvent, e.g., CH$_2$Cl$_2$, provides a compound of Formula 37.0:

(37.0)

The compound of Formula 37.0 can be derivatized by reaction with different reagents using techniques well know in the art to give additional compounds of the invention, i.e., compounds of Formula 1.17a. Such reagents and conditions, and the compound that is produced are summarized in Table 5. $R^{20}$ in Table 5 refers to the substituent in Formula 1.17a (1.17a)

and the compound numbers in parenthesis in the column for $R^{20}$ refer to the compounds described above.

TABLE 5

| Reagent (Reagent Class) | Conditions | $R^{20}$ |
|---|---|---|
| TMS-NCO (Isocyanate) | CH$_2$Cl$_2$ | (38.0) |
| Ethyl Oxalyl Chloride (Acid Chloride) | CH$_2$Cl$_2$/Et$_3$N | (39.0) |
| Methanesulfonyl Chloride (Sulfonyl Chloride) | CH$_2$Cl$_2$/Et$_3$N | —SO$_2$CH$_3$ (40.0) |

TABLE 5-continued

| Reagent (Reagent Class) | Conditions | R²⁰ |
|---|---|---|
| 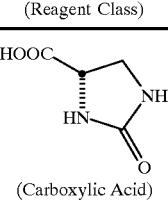 (Carboxylic Acid) | DEC•HOBT/ HOBT•H₂O/NMM | 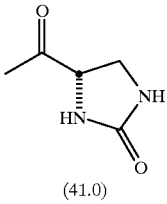 (41.0) |
| Benzaldehyde (Aldehyde) | CH₃C(O)OH/ Na(CN)₃BH | 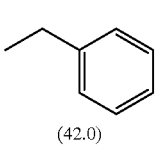 (42.0) |

The corresponding trans compounds can be prepared following the above procedure with Formula 125.0.

Compounds of Formula 1.0, wherein m is 0 and R is:

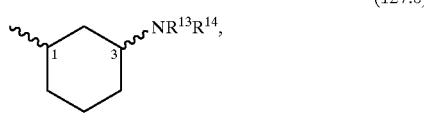 (127.0)

for example

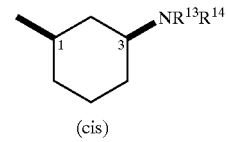 (128.0)

(cis)

or

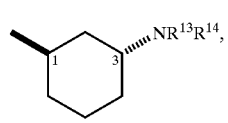 (129.0)

(trans)

can be prepared by reaction of 117.0 (e.g., 119.0) with the corresponding carboxylic acid

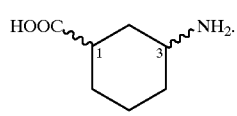 (130.0)

The carboxylic acid, 130.0, can be prepared according to techniques known in the art (e.g., *J. Am. Chem. Soc.* 1938, 60, 2341). The nitrogen atom of cis-(+/−)-3-aminocyclohexanecarboxylic acid 130.0 can be protected with a suitable protecting group (e.g., BOC) by techniques known in the art to provide intermediate acid 131.0:

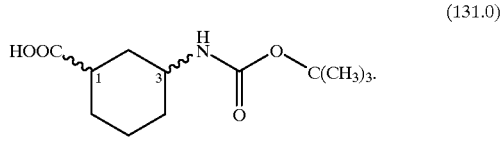 (131.0)

Following the procedures described above for the 1,4-cyclohexyl derivatives, the 1,3-cyclohexyl derivatives can be made from 131.0 and 117.0. Thus, for example, reaction of 126.0 with 131.0 provides Compound 43.0. Reaction of 43.0 with TFA yields Compound 44.0. Additional compounds of the invention are produced from Compound 1.18

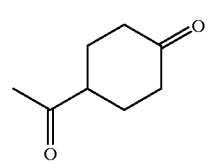 (1.18)

and the reagents listed in Table 6:

TABLE 6

| Reagent (Reagent Class) | Conditions | R²¹ |
|---|---|---|
| TMS-NCO (Isocyanate) | CH₂Cl₂ | 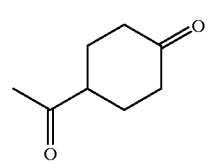 (45.0) |
| Ethyl Oxalyl Chloride (Acid Chloride) | CH₂Cl₂/Et₃N | 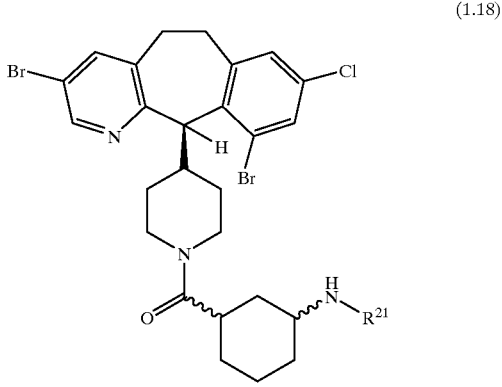 (46.0) |
| 4-Oxocyclohexane-carboxylic acid (Carboxylic Acid) | DEC•HOBT/HOBT H₂O/NMM | (47.0) |
| Methanesulfonyl Chloride (Sulfonyl Chloride) | CH₂Cl₂/Et₃N | —SO₂CH₃ (48.0) |

TABLE 6-continued

| Reagent (Reagent Class) | Conditions | $R^{21}$ |
|---|---|---|
| Benzaldehyde (Aldehyde) | $CH_3C(O)OH/$ $Na(CN)_3BH$ | 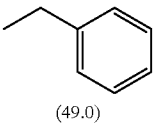 (49.0) |

Similar to the procedures described above, enantiomerically pure cis-3-aminocyclohexanecarboxylic acid (*Aust. J. Chem.* 1981, 34, 2231) having 1R,3S (132.0) or 1S,3R (133.0) absolute configuration

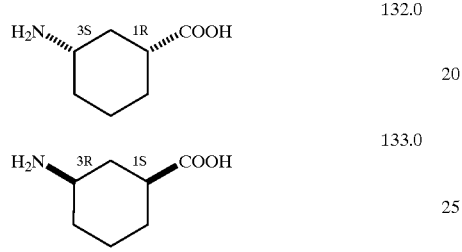

could be used to prepare compounds of Formula 1.0 that are similar to the compounds of Formulas 43.0 and 44.0 and their derivatives described above.

Compounds similar to 43.0 and 44.0, and their derivatives described above, can be prepared from (+/−)-trans-3-aminocyclohexanecarboxylic acid {(+/−)-134.0}

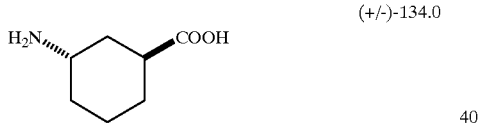

(*J. Org. Chem.* 1949, 14, 1013) by the methodology described above. Those skilled in the art will recognize that {(+/−)-134.0} can be resolved into individual enantiomers 135.0 and 136.0

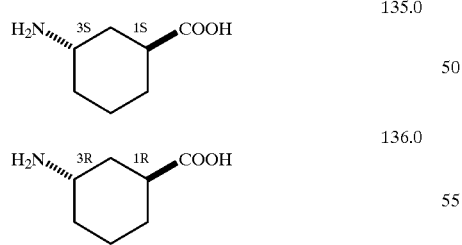

by using any of several standard techniques, e.g., chromatography of the acid or a suitable derivative on a "chiral" column; fractional crystallization of a diastereomerically enriched salt, e.g. brucine, strychnine, ornithine; preparation of a derivative using an enantiomerically pure reagent, e.g., (+)-menthyl chloroformate; or enzymatic resolution of an appropriate derivative, e.g. porcine pancreatic lipase hydrolysis of an ester, e.g. the ethyl ester. Compounds similar to 43.0 and 44.0 and their derivatives described above can be prepared from enantiomers 135.0 and 136.0 by the methodology described above.

Compounds of Formula 1.0, wherein m is 1 and R is

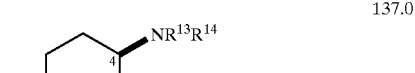

or

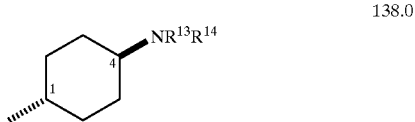

can be prepared by reaction of the corresponding N-protected (e.g., BOC) carboxylic acid:

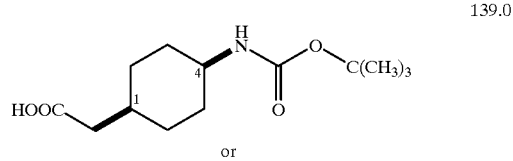

or

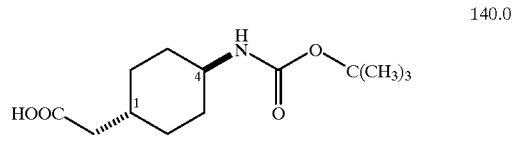

with the tricyclic amine 117.0. The N-protected 139.0 and 140.0 (*Chem. Ber.* 1934, 67, 245) can be prepared using techniques known in the art. From these compounds and a tricyclic amine 117.0, e.g., 119.0, Compounds 50.0, 51.0, 52.0 and 53.0 (described above) can be obtained. Derivatives of Compounds 51.0 and 53.0 can be prepared by procedures similar to those described above. Reagents and conditions for the preparation of Compounds of Formulas 1.19 and 1.20

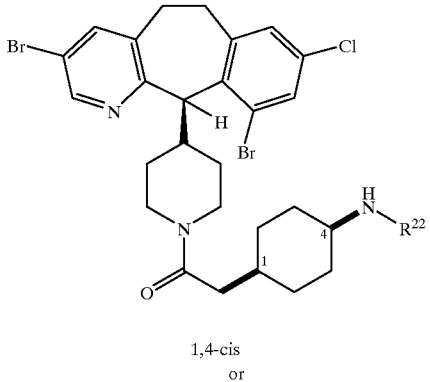

-continued (1.20)

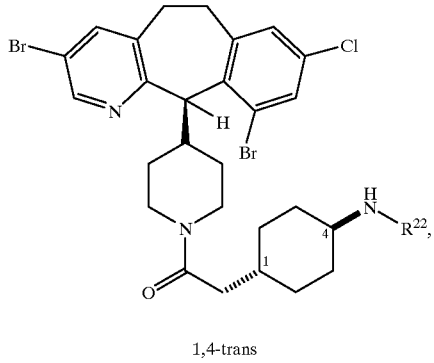

1,4-trans i.e., Compounds 54.0–57.0, are given in Table 7:

TABLE 7

| Reagent (Reagent Class) | Conditions | R²² |
|---|---|---|
| TMS—NCO (Isocyanate) | $CH_2Cl_2$ | (54.0-cis, 55.0-trans) |
| Ethyl Oxalyl Chloride (Acid Chloride) | $CH_2Cl_2/Et_3N$ | ![](ethyl oxalyl) (56.0-cis, 57.0-trans) |
| HOOC—(imidazolidinone) (Carboxylic Acid) | DEC.HOBT/HOBT. $H_2O$/NMM | ![](imidazolidinone ketone) (58.0-cis, 59.0-trans) |
| Methanesulfonyl Chloride (Sulfonyl Chloride) | $CH_2Cl_2/Et_3N$ | —$SO_2CH_3$ (60.0-cis, 61.0-trans) |
| Benzaldehyde (Aldehyde) | $CH_3C(O)OH/$ $Na(CN)_3BH$ | (62.0-cis, 63.0-trans) |

Compounds of Formula 1.0, wherein m is 1 and R is (141.0)

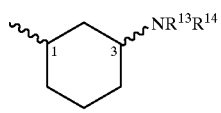

such as, for example, (142.0)

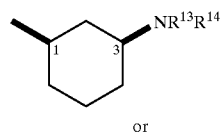

or (143.0)

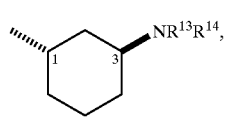

can be prepared by reaction of the corresponding carboxylic acid (144.0)

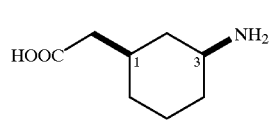

or (145.0)

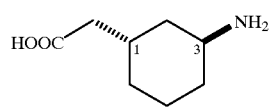

with a tricyclic amine 117.0. Carboxylic acids (+/−)-cis 144.0 and (+/−)-trans 145.0 can be prepared according to the procedure described in *J. Org. Chem.* 1949, 14, 1013. Each of these acids may be protected on nitrogen with, e.g., BOC, to give (+/−)-146.0 and (+/−)-147.0

(146.0)

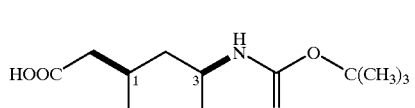

(147.0)

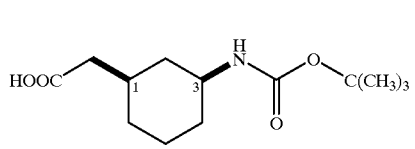

The N-protected acids (146.0 or 147.0) are reacted with a tricyclic amine 117.0, e.g., 119.0 (e.g., 126.0), according to the procedures discussed above (see for example the preparation of Compound 37.0). In this manner, Compounds 64.0 and 65.0, described above, can be prepared. Compounds 64.0 and 65.0 can be derivatized to produce compounds according to the procedure described above for the preparation of Compounds 58.0 to 63.0.

Those skilled in the art will recognize that (+/−)-146.0 and (+/−)-147.0 can be resolved into individual enantiomers by using any of several standard techniques, e.g., chromatography of the acid or a suitable derivative on a "chiral" column; fractional crystallization of a diastereomerically enriched salt, e.g. brucine, strychnine, or ornithine; preparation of a derivative using an enantiomerically pure reagent, e.g., (+)-menthyl chloroformate; or enzymatic resolution of an appropriate derivative, e.g., porcine pancreatic lipase hydrolysis of an ester, e.g., the ethyl ester. Further, nitrogen protected derivatives, e.g., BOC, of the individual enantiomers of cis- and trans-3-aminocyclohexylacetic acid, can be prepared using standard techniques known to those skilled in the art to provide intermediates 148.0, 149.0, 150.0 and 151.0 having the absolute stereochemistries drawn:

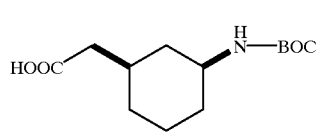

148.0

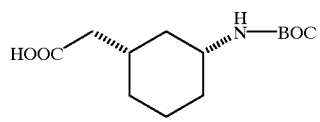

149.0

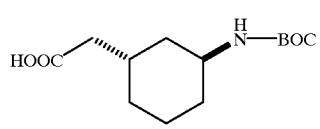

150.0

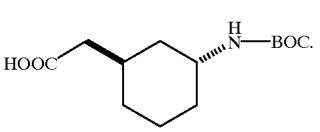

151.0

Compounds 148.0–151.0 can be reacted with a tricyclic amine of Formula 117.0, e.g., 126.0, according to the procedures described above, to produce compounds 64.0, 65.0, 66.0 and 67.0. Compounds 64.0–67.0 can be derivatized to produce compounds according to the procedure described above for the preparation of Compounds 58.0 to 63.0.

Compounds of Formula 1.0 wherein m is 0 and R is

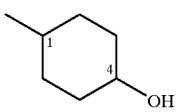

(152.0)

can be made by reacting the corresponding carboxylic acid with a tricyclic amine of Formula 117.0, e.g., 126.0.

Trans-4-hydroxycyclohexanecarboxylic acid (153.0)

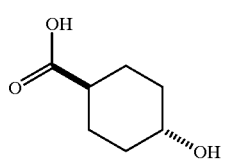

(153.0)

can be treated with, for example, 126.0, a dehydrating agent (e.g., DEC•HCl); a catalyst (e.g., HOBT•H$_2$O); and a base (e.g., NMM) in a suitable solvent (e.g., DMF) to give Compound 68.0.

Cis-4-hydroxycyclohexanecarboxylic acid (154.0)

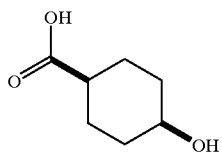

(154.0)

can be treated with an acid anhydride (e.g., acetic anhydride) and a base (e.g., pyridine) to afford cis-4-acetoxycyclohexanecarboxylic acid (155.0)

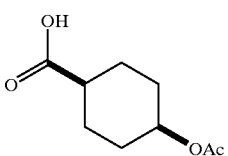

(155.0)

Compound 155.0 can be coupled with a tricyclic amine of formula 117.0, e.g., 126.0, using the procedures described above for the preparation of 68.0, to afford Compound 69.0. Compound 69.0 can be treated with an acid (e.g., 6 M HCl) to afford Compound 70.0.

Similar to the procedure described above for the 4-hydroxycyclohexyl derivatives, compounds of Formula 1.0 wherein m is 0 and R is

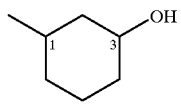

(156.0)

can be prepared. Thus, by reacting 126.0 with the acids

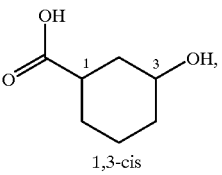

(157.0)

1,3-cis

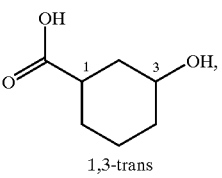

(158.0)

1,3-trans (159.0)

-continued

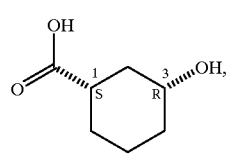
(160.0)

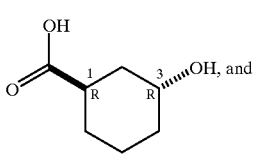
(161.0)

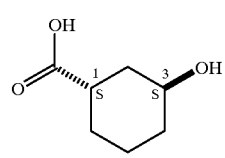
(162.0)

Compounds 71.0, 72.0, 73.0, 74.0, 75.0 and 76.0, respectively can be obtained.

Compounds of Formula 1.0 wherein m is 0 and R is

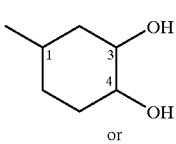
(163.0)

or

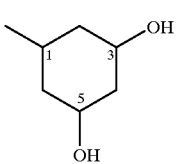
(164.0)

can be prepared by reacting a tricyclic amine of Formula 117.0, e.g., 126.0, with the corresponding carboxylic acid of 163.0 or 164.0 using to the procedures described above for preparing Compounds 68.0 and 70.0. Compounds 77.0 or 78.0 are prepared in this manner.

Compounds of Formula 1.0 wherein m is 0 and R is a cyclohexyl ring having an alkoxy substituent (e.g., methoxy)—see compounds 79.0 to 86.0—can be prepared from the corresponding carboxylic acid of the alkoxy substitued cyclohexyl ring by the procedures described above.

Compounds of Formula 1.0 wherein m is 0 and R is a cyclohexyl ring having an ester substituent (e.g., Compound 87.0) can be prepared by techniques known in the art from compounds having a hydroxy substitued cyclohexyl ring. For example, compound 87.0 can be prepared by treating Compound 68.0 with benzoyl chloridean an acid chloride (an acid chloride) and pyridine (a base) in dichloromethane (solvent).

Compounds of Formula 1.0 wherein m is 1 and R is a cyclohexyl ring substitued with a carbamate can be prepared from a corresponding compound that is a monoalcohol (i.e., R is a hydroxy substitued cyclohexyl ring). The carbamates can be prepared by techniques well known in the art, such as reaction with an isocyanate in a suitable base and a suitable solvent. For example, Compound 68.0 can be reacted with trichloroacetyl isocyanate and pyridine (base) in dichloromethane (solvent) to yield Compound 88.0. the trichloroacetyl group can be hydrolyzed to yield Compound 89.0. Hydrolysis can be done with $K_2CO_3$ in methanol.

Additionally, any of the alcohols mentioned above could be reacted with a chloroformate, e.g,. 4-nitrophenyl chloroformate, and a base, e.g., $Et_3N$, to give carbonate 90.0. Treatment of 90.0 with any primary or secondary amine, e.g., ethanolamine, would afford a carbamate, e.g., 91.0.

(+/−)-4-Ethoxy-3-hydroxycyclohexanecarboxylic acid (*J. Org. Chem.*; 1961, 26, 1405) can be coupled with a tricyclic amine of Formula 117.0, e.g., 126.0, using the procedures described above for the preparation of 68.0 and 70.0 to afford Compound 92.0 as a mixture of diastereomers. Similarly, a tricyclic amine, such as 126.0, can be coupled with (+/−)-4-hydroxy-3-methoxycyclohexanecarboxylic acid (*J. Org. Chem.*; 1992, 57, 1405) to afford compound 93.0 as a mixture of diastereomers. One of the tricyclic amines, such as 126.0, can be coupled with (+/−)-4,3-dimethoxycyclohexanecarboxylic acid to afford Compound 94.0 as a mixture of diastereomers. Treatment of one of the monoalcohols, e.g., 92.0, with an alkyl halide, e.g., benzyl bromide, a base, e.g., NaH, in a solvent, e.g., DMF would afford 3-benzyl-4-ethyl diether 95.0 as a mixture of diastereomers.

Epoxyester 165.0 (*Tetrahedron*, 1992, 48, 539) could be treated with an alcohol, e.g., benzyl alcohol, and a base, e.g., NaH, in a suitable solvent, e.g., THF, to afford a mixture of esters 166.0 and 167.0:

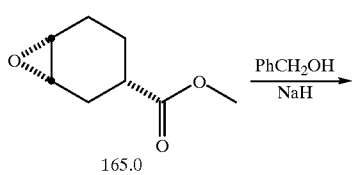
165.0

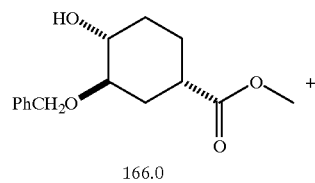
166.0

-continued

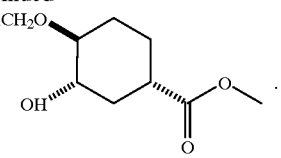

167.0

Hydrolysis of the esters and coupling of the resultant acids with a tricyclic amine of Formula 117.0, e.g., 126.0, using the procedures described above for the preparation of 68.0 and 70.0, yields compounds of the invention illustrated by Compound 96.0.

Compound 77.0 could be treated with an acid chloride, e.g., acetyl chloride, or a chemically equivalent reagent, and a base, e.g., pyridine, in a suitable solvent, e.g., dichloromethane, to obtain esterified compounds exemplified by diacetate Compound 97.0.

Acid 168.0, derived from ester 166.0 (described above), could be treated with two equivalents of a base, e.g., NaH, and one equivalent of a silyl chloride, e.g., t-butyldiphenylchlorosilane, in a suitable solvent, e.g., DMF, to afford acid 169.0

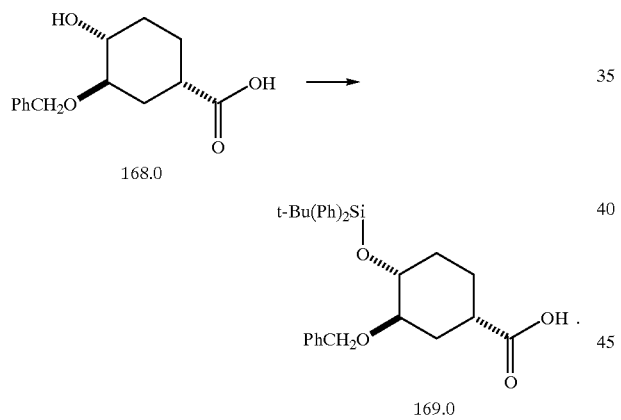

The benzyl group could be removed, e.g., by catalytic hydrogenation, and the resulting hydroxy acid 170.0 could be coupled with a tricyclic amine, e.g. 126.0, using the procedures described above for the preparation of 68.0 and 70.0, to afford the Compound 171.0

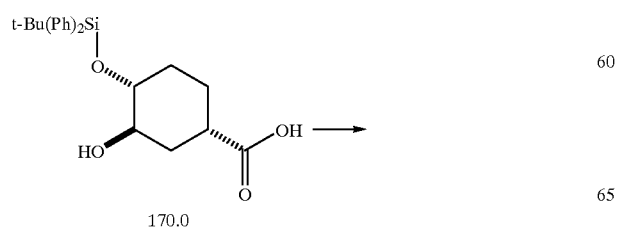

-continued

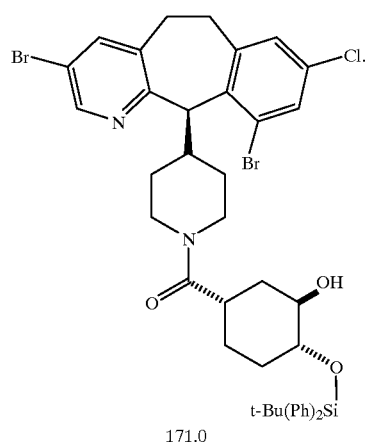

171.0

Alcohol 171.0 could be treated with an acid chloride, e.g., acetyl chloride or an equivalent reagent, and a base, e.g., pyridine, in a solvent, e.g., dichloromethane, to afford acetate 172.0

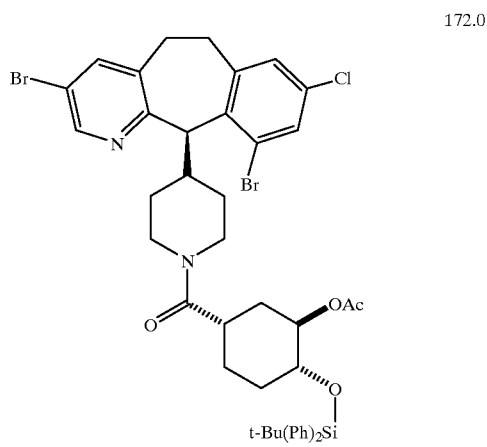

172.0

Removal of the silyl group by any of the methods known in the art would give hydroxyacetate 98.0A. Following a similar procedure starting with the acid derived from 167.0 would provide 98.0B

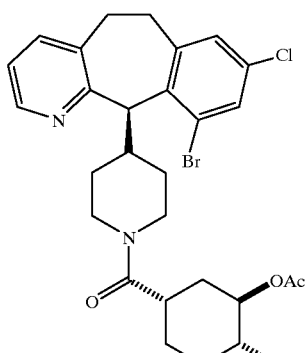

98.0A

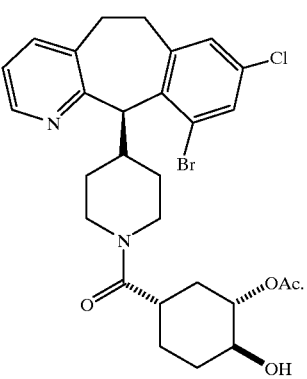

98.0B

The hydroxyacetates 98.0A and 98.0B could be treated with an acid chloride, e.g., benzoyl chloride or an equivalent reagent, and a base, e.g., pyridine, in a solvent, e.g., dichloromethane, to afford diesters 99.0A and 99.0B, respectively

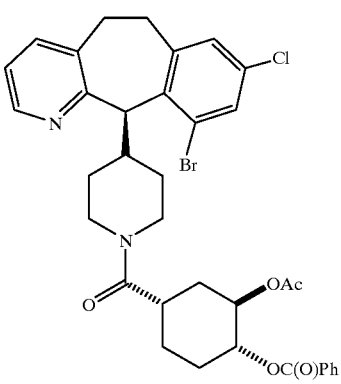

99.0A

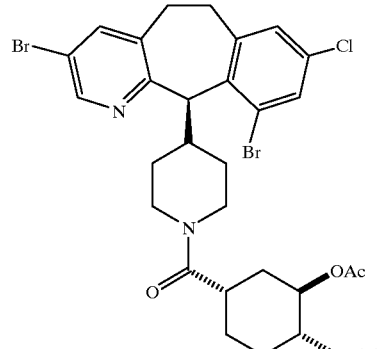

99.0B

Any of the monoethers described above, e.g., 92.0, could be treated with an acid chloride, e.g., acetyl chloride, or a chemically equivalent reagent, and a base, e.g., pyridine, in a suitable solvent, e.g., dichloromethane, to obtain esterified compounds exemplified by acetate Compound 100.0.

Starting from any of the monoalcohols or diols described above, and following the procedure outlined above for the preparation of 88.0, 89.0 and 91.0, carbamates exemplified by Compounds 101.0, 102.0 and 103.0 could be prepared.

(+/−)-3,5-Dimethoxycyclohexanecarboxylic acid (German Patent DE 81443) can be coupled with a tricyclic amine of formula 117.0, e.g., 126.0, using the procedures described above for the preparation of 68.0 and 70.0 to afford Compound 104.0 as a mixture of diastereomers.

Racemic ester 173.0 (J. Am. Chem. Soc. 1994, 116, 3296) could be hydrolyzed to the acid 174.0

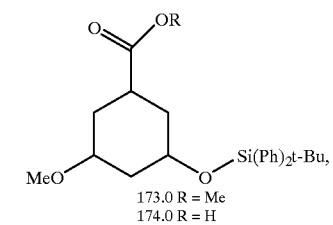

173.0 R = Me
174.0 R = H and 174.0 can be coupled with e.g., 126.0 (a tricyclic amine of 117.0) using the procedures described above for the preparation of 68.0 and 70.0 to afford Compound 105.0 as a mixture of diastereomers. Removal of the silyl group by methods known in the art would give hydroxyether 106.0. Treatment of 106.0 with an alkyl halide, e.g., benzyl bromide, a base, e.g., NaH, in a solvent, e.g., DMF would afford 3-benzyl-5-methyl ether 107.0 as a mixture of diastereomers.

Hydroxy Compound 78.0 could be treated with an acid chloride, e.g., acetyl chloride, or a chemically equivalent reagent, and a base, e.g., pyridine, in a suitable solvent, e.g., dichloromethane, to obtain an esterified target exemplified by diacetate 108.0.

Racemic hydroxyester 175.0 (*J. Am. Chem. Soc.* 1994, 116, 3296) could be hydrolyzed to the acid 176.0

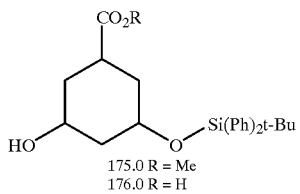

175.0 R = Me
176.0 R = H and 176.0 could be coupled with a tricyclic amine (117.0), e.g., 126.0, using the procedure described above for the preparation of 68.0 and 70.0 to afford Compound 109.0. Alcohol 109.0 could be treated with an acid chloride, e.g., acetyl chloride or an equivalent reagent, and a base, e.g., pyridine, in a solvent, e.g., dichloromethane, to afford acetate 110.0. Removal of the silyl group by methods known in the art would give hydroxyacetate 111.0. Hydroxyacetate 111.0 could be reacted with an acid chloride, e.g., benzoyl chloride, and a base, e.g., pyridine, in a suitable solvent, e.g., dichloromethane to afford diester 112.0.

A monoether e.g., 106.0, could be reacted with an acid chloride, e.g., acetyl chloride, or a chemically equivalent reagent, a base, e.g., pyridine, in a suitable solvent, e.g., dichloromethane, to obtain compounds exemplified by Compound 113.0.

Starting from any of the monoalcohols or diols described above, and following the procedures outlined above for the preparation of 88.0, 89.0 and 91.0, carbamates exemplified by Compounds 114.0, 115.0 and 116.0 can be obtained.

Cyclic ketones (177.0) can be alkylated next to the carbonyl with a bromo ester (178.0) under basic conditions as described in J. Am. Chem. Soc. (1957), 79, 3503. The corresponding ketoesters (179.0) are easily hydrolyzed with aqueous base to give the keto acids (180.0)

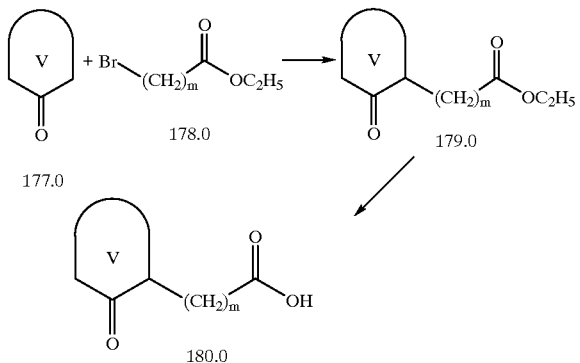

wherein Ring V represents a 4, 5 or 6 membered cycloalkyl ring defined above, and wherein m is as defined for Formula 1.0 above.

Cyclic ketoamines can be alkylated in the nitrogen with a bromoester and then hydrolyzed as described in J. Med. Chem. (1994), 37, 3883

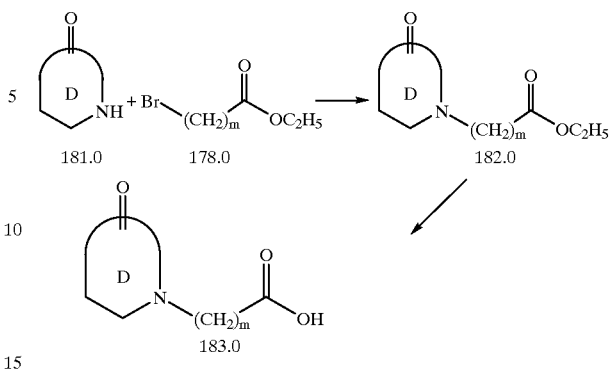

wherein Ring D represents a 4, 5 or 6 membered heterocycloalkyl ring, as defined above, (inclusive of the heteroatom N), wherein the =O substituent is not on a carbon adjacent to the N atom, and wherein m is as defined for Formula 1.0 above.

Monoprotected diketones can be reacted in a Wittig reaction followed by hydrolysis to the unsaturated keto acid, or by first reducing the double bond followed by hydrolysis to the saturated keto acid. Examples of this can be found in Tetrahedron (1995), 51, 10259, Synthetic Comm. (1990), 20, 2019, Chemical Abstracts (1958), 6370a and Chemical Abstracts (1957), 6371b.

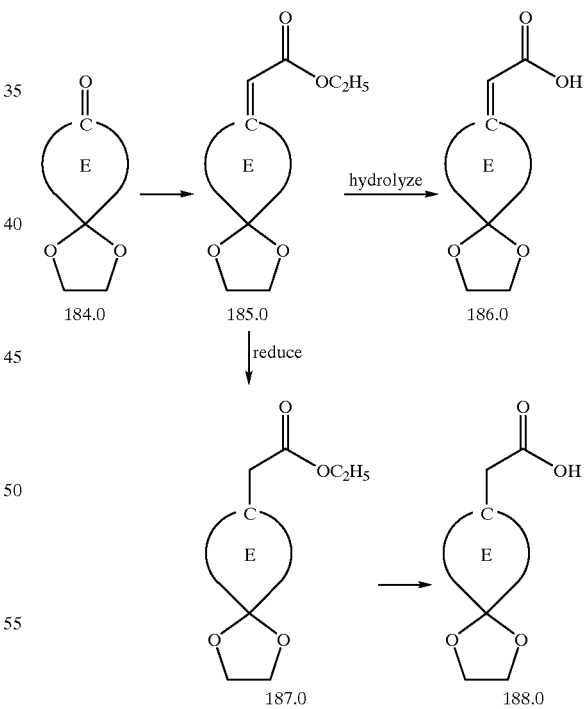

wherein Ring E represents a 4, 5, or 6 membered cycloalkyl ring defined above.

The ester in the above ketalesters can also be selectively hydrolyzed to the corresponding ketal acids which can be coupled to the tricyclic amine 119.0 to produce compounds of Formula 1.22 containing a ketal group

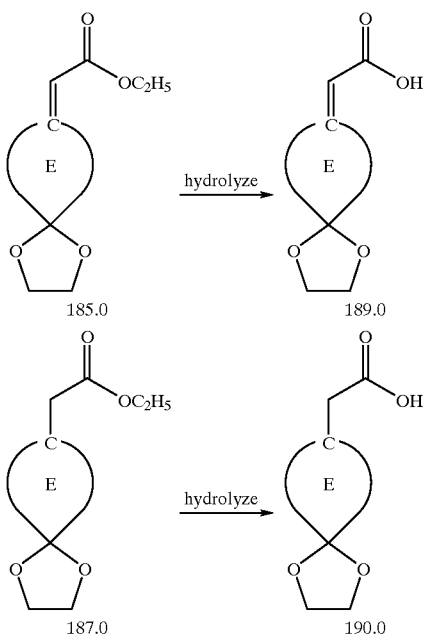

Compounds of Formula 117.0A

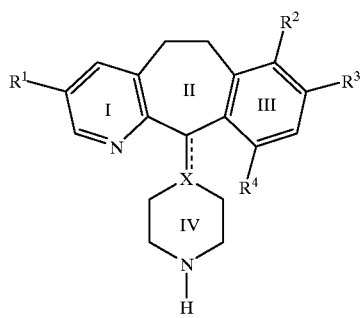
(117.0A)

are prepared by methods known in the art, for example by methods disclosed in WO 95/10516, in U.S. Pat. No. 5,151, 423 and those described below. Compounds of Formula 13.0a wherein X is C (when the double bond is present) or CH and the C-3 position of the pyridine ring in the tricyclic structure is substituted by bromo (i.e., $R^1$ is Br) can also be prepared by a procedure comprising the following steps:

(a) reacting an amide of the formula

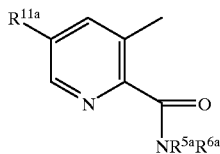

wherein $R^{11}$a is Br, $R^{5a}$ is hydrogen and $R^{6a}$ is $C_1$–$C_6$ alkyl, aryl or heteroaryl; $R^{5a}$ is $C_1$–$C_6$ alkyl, aryl or heteroaryl and $R^{6a}$ is hydrogen; $R^{5a}$ and $R^{6a}$ are independently selected from the group consisting of $C_1$–$C_6$ alkyl and aryl; or $R^{5a}$ and $R^{6a}$, together with the nitrogen to which they are attached, form a ring comprising 4 to 6 carbon atoms or comprising 3 to 5 carbon atoms and one hetero moiety selected from the group consisting of —O— and —$NR^{9a}$—, wherein $R^{9a}$ is H, $C_1$–$C_6$ alkyl or phenyl;

with a compound of the formula

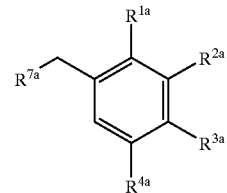

wherein $R^{1a}$, $R^{2a}$, $R^{3a}$ and $R^{4a}$ are are independently selected from the group consisting of hydrogen and halo and $R^{7a}$ is Cl or Br, in the presence of a strong base to obtain a compound of the formula

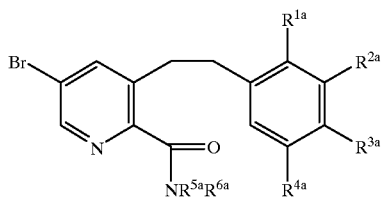

(b) reacting a compound of step (a) with
(i) $POCl_3$ to obtain a cyano compound of the formula

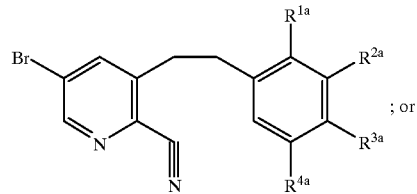

; or (ii) DIBALH to obtain an aldehyde of the formula

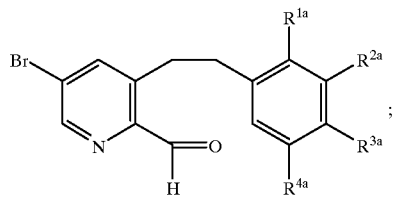

;

(c) reacting the cyano compound or the aldehyde with a piperidine derivative of the formula

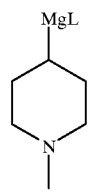

wherein L is a leaving group selected from the group consisting of Cl and Br, to obtain a ketone or an alcohol of the formula below, respectively:

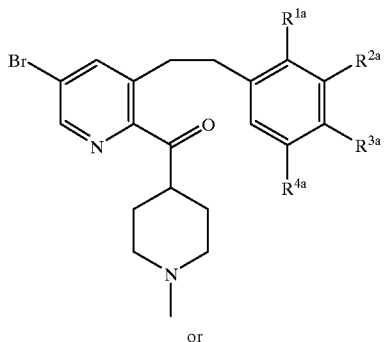

or

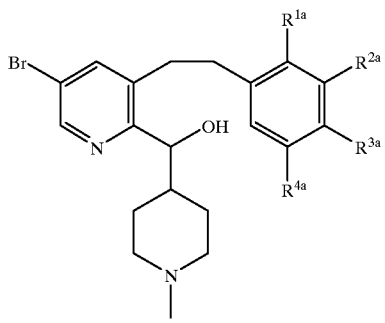

(d)(i) cyclizing the ketone with $CF_3SO_3H$ to obtain a compound of the formula

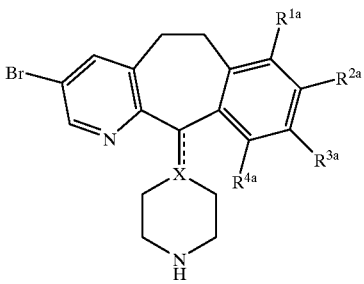

wherein the dotted line represents a double bond; or (d)(ii) cyclizing the alcohol with polyphosphoric acid to obtain a compound wherein the dotted line represents a single bond.

Methods for preparing intermediate compounds disclosed in WO 95/10516, U.S. Pat. No. 5,151,423 and described below employ a tricyclic ketone intermediate. Such intermediates of the formula

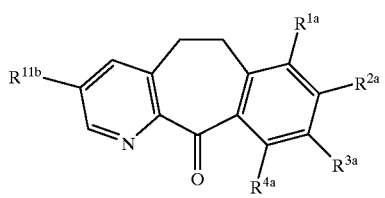

wherein $R^{11b}$, $R^{1a}$, $R^{2a}$, $R^{3a}$ and $R^{4a}$ are independently selected from the group consisting of hydrogen and halo, can be prepared by the following process comprising:

(a) reacting a compound of the formula

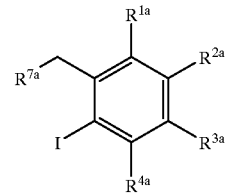

(i) with an amine of the formula $NHR^{5a}R^{6a}$, wherein $R^{5a}$ and $R^{6a}$ are as defined in the process above; in the presence of a palladium catalyst and carbon monoxide to obtain an amide of the formula:

[structure]

; or (ii) with an alcohol of the formula $R^{10a}OH$, wherein $R^{10a}$ is $C_1$–$C_6$ lower alkyl or $C_3$–$C_6$ cycloalkyl, in the presence of a palladium catalyst and carbon monoxide to obtain the ester of the formula

[structure]

followed by reacting the ester with an amine of formula $NHR^{5a}R^{6a}$ to obtain the amide;

(b) reacting the amide with an iodo-substituted benzyl compound of the formula

[structure]

wherein $R^{1a}$, $R^{2a}$, $R^{3a}$, $R^{4a}$ and $R^{7a}$ are as defined above, in the presence of a strong base to obtain a compound of the formula

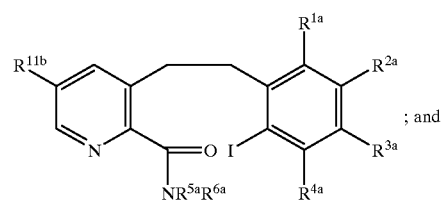

; and (c) cyclizing a compound of step (b) with a reagent of the formula $R^{8a}MgL$, wherein $R^{8a}$ is $C_1$–$C_8$ alkyl, aryl or heteroaryl and L is Br or Cl, provided that prior to cyclization, compounds wherein $R^{5a}$ or $R^{6a}$ is hydrogen are reacted with a suitable N-protecting group.

Compounds of Formula 1.0, wherein substituent a is NO (Ring I) and X is C or CH, can be made from compounds of Formula 117.0A using procedures well known to those skilled in the art. For example the compound of Formula 117.0A can be reacted with m-chloro-peroxybenzoic acid in a suitable organic solvent, e.g., dichloro-methane (usually anhydrous) or methylene chloride, at a suitable temperature, to produce a compound of Formula 117.0B

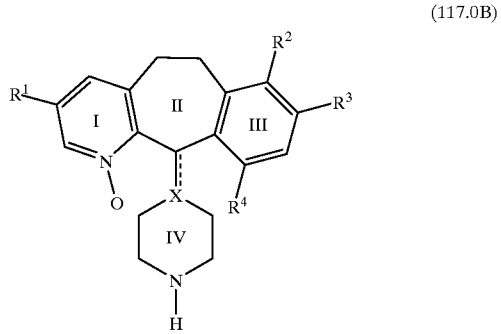

(117.0B)

Generally, the organic solvent solution of Formula 117.0A is cooled to about 0° C. before the m-chloroperoxybenzoic acid is added. The reaction is then allowed to warm to room temperature during the reaction period. The desired product can be recovered by standard separation means. For example, the reaction mixture can be washed with an aqueous solution of a suitable base, e.g., saturated sodium bicarbonate or NaOH (e.g., 1N NaOH), and then dried over anhydrous magnesium sulfate. The solution containing the product can be concentrated in vacuo. The product can be purified by standard means, e.g., by chromatography using silica gel (e.g., flash column chromatography).

Alternatively, compounds of Formula 1.0, wherein substituent a is NO and X is C or CH, can be made from compounds of Formula 1.0, wherein substituent a is N, by the m-chloroperoxybenzoic acid oxidation procedure described above.

Also, alternatively, the compounds of Formula 1.0, wherein substituent a is NO and X is C or CH, can be made from tricyclic ketone compounds

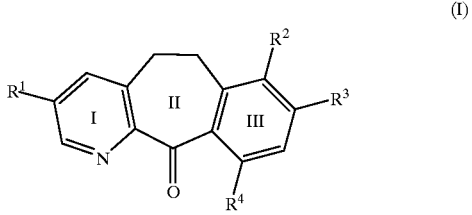

(I)

using the oxidation procedure with m-chloroperoxybenzoic acid. The oxidized intermediate compounds

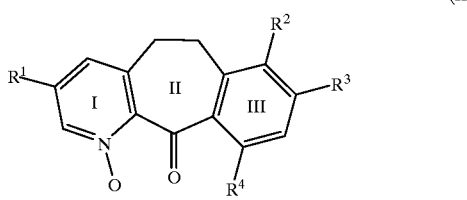

(II)

are then reacted by methods known in the art to produce compounds of the invention.

Those skilled in the art will appreciate that the oxidation reaction can be conducted on racemic mixtures and the isomers can then be separated by know techniques, or the isomers can be separated first and then oxidized to the corresponding N-oxide.

Those skilled in the art will appreciate that it is preferable to avoid an excess of m-chloroperoxybenzoic acid when the oxidation reaction is carried out on the compounds having a C-11 double bond to piperidine Ring IV. In these reactions an excess of m-chloroperoxybenzoic acid can cause epoxidation of the C-11 double bond.

(+)-Isomers of compounds of Formula 117.0A wherein X is CH can be prepared with high enantioselectivity by using a process comprising enzyme catalyzed transesterification. Preferably, a racemic compound of Formula 117.0A, wherein X is C, the double bond is present and $R^4$ is not H, is reacted with an enzyme, such as Toyobo LIP-300, and an acylating agent, such as trifluoroethly isobutyrate; the resultant (+)-amide is then hydrolyzed, for example by refluxing with an acid such as $H_2SO_4$, to obtain the corresponding optically enriched (+)-isomer wherein X is CH and $R^4$ is not H. Alternatively, a racemic compound of Formula 117.0A, wherein X is C, the double bond is present and $R^4$ is not H, is first reduced to the corresponding racemic compound of Formula 117.0A wherein X is CH and then treated with the enzyme (Toyobo LIP-300) and acylating agent as described above to obtain the (+)-amide, which is hydrolyzed to obtain the optically enriched (+)-isomer.

Compounds of the invention, wherein a is NO and X is N, can be prepared from the tricyclic ketone (II) described above. Ketone (II) can be converted to the corresponding C-11 hydroxy compound which in turn can be converted to the corresponding C-11 chloro compound

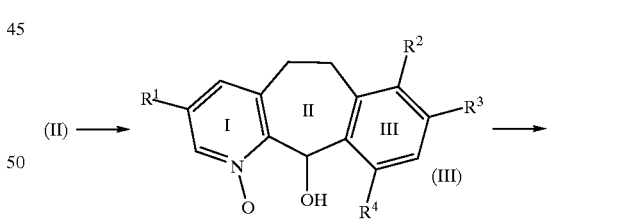

(II) → (III)

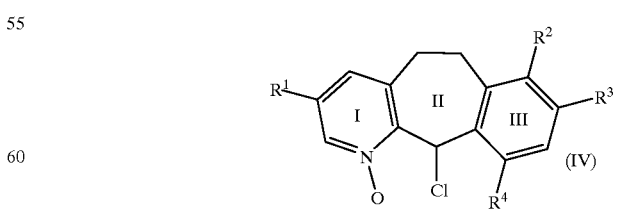

(IV)

and (IV) can then be reacted with piperazine to produce the intermediate

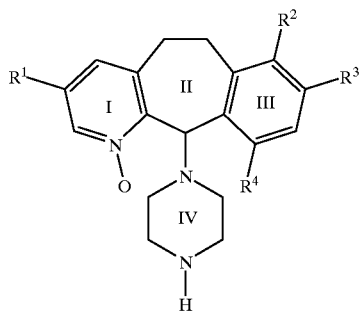

Intermediate (V) can then be reacted with the reagents, using techniques well known in the art, which will provide the desired compound.

Compounds useful in this invention are exemplified by the following examples, which should not be construed to limit the scope of the disclosure.

PREPARATIVE EXAMPLE 1

Step A:

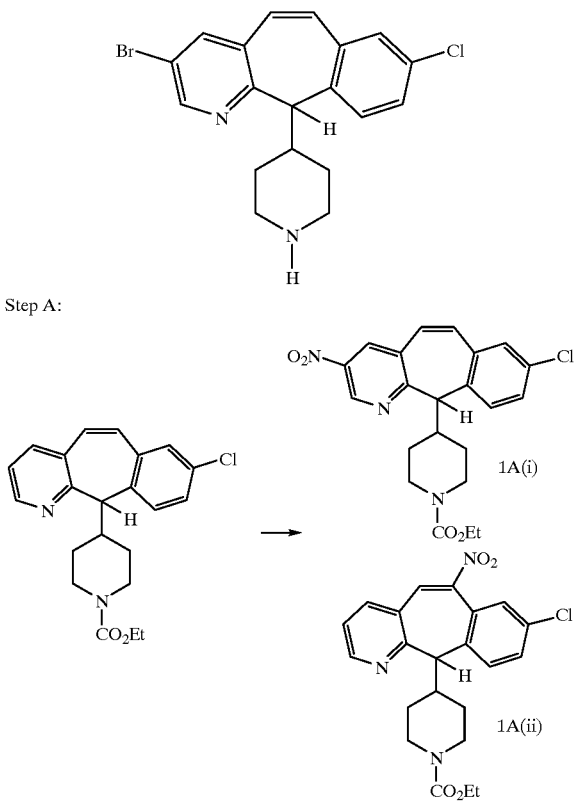

Combine 14.95 g (39 mmol) of 8-chloro-11-(1-ethoxycarbonyl-4-piperidinyl)-11H-benzo[5,6]cyclohepta[1,2-b]pyridine and 150 mL of $CH_2Cl_2$, then add 13.07 g (42.9 mmol) of $(nBu)_4NNO_3$ and cool the mixture to 0° C. Slowly add (dropwise) a solution of 6.09 mL (42.9 mmol) of TFAA in 20 mL of $CH_2Cl_2$ over 1.5 hours. Keep the mixture at 0° C. overnight, then wash successively with saturated $NaHCO_3$ (aqueous), water and brine. Dry the organic solution over $Na_2SO_4$, concentrate in vacuo to a residue and chromatograph the residue (silica gel, EtOAc/hexane gradient) to give 4.32 g and 1.90 g of the two product compounds 1A(i) and 1A(ii), respectively. Mass Spec. for compound 1A(i): $MH^+=428.2$. Mass Spec. for compound 1A(ii): $MH^+=428.3$.

Step B:

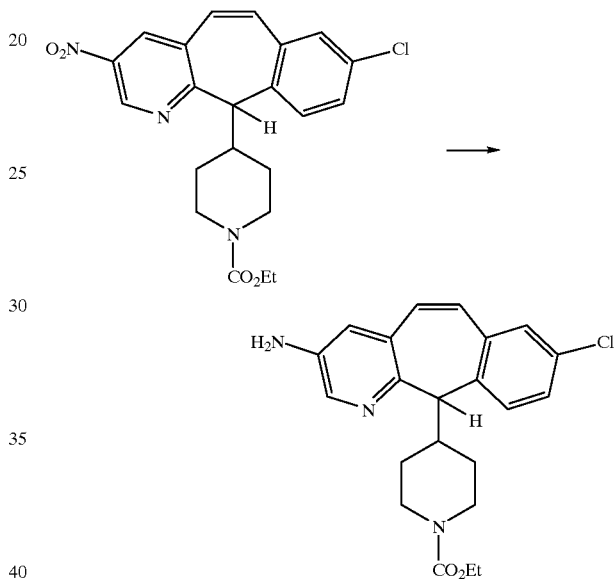

Combine 22.0 g (51.4 mmol) of the product 1A(i) from Step A, 150 mL of 85% EtOH (aqueous), 25.85 g (0.463 mole) of Fe powder and 2.42 g (21.8 mmol) of $CaCl_2$, and heat at reflux overnight. Add 12.4 g (0.222 mole) of Fe powder and 1.2 g (10.8 mmol) of $CaCl_2$ and heat at reflux for 2 hours. Add another 12.4 g (0.222 mole) of Fe powder and 1.2 g (10.8 mmol) of $CaCl_2$ and heat at reflux for 2 hours more. Filter the hot mixture through celite®, wash the celite® with 50 mL of hot EtOH and concentrate the filtrate in vacuo to a residue. Add 100 mL of anhydrous EtOH, concentrate to a residue and chromatograph the residue (silica gel, $MeOH/CH_2Cl_2$ gradient) to give 16.47 g of the product compound.

Step C:

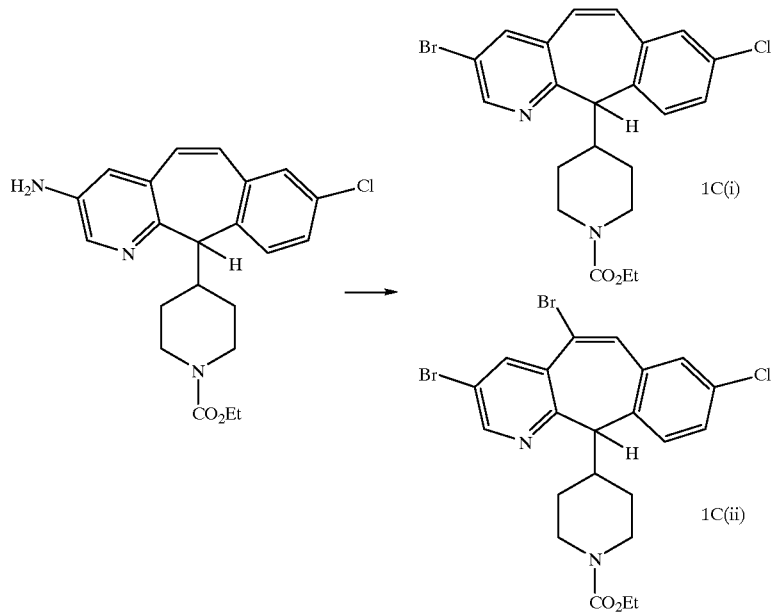

Combine 16.47 g (41.4 mmol) of the product from Step B, and 150 mL of 48% HBr (aqueous) and cool to −3° C. Slowly add (dropwise) 18 mL of bromine. then slowly add (dropwise) a solution of 8.55 g (0.124 mole) of $NaNO_2$ in 85 mL of water. Stir for 45 minutes at −3° to 0° C., then adjust to pH=10 by adding 50% NaOH (aqueous). Extract with EtOAc, wash the extracts with brine and dry the extracts over $Na_2SO_4$. Concentrate to a residue and chromatograph (silica gel, EtOAc/hexane gradient) to give 10.6 g and 3.28 g of the two product compounds 1C(i) and 1C(ii), respectively. Mass Spec. for compound 1C(i): $MH^+$=461.2. Mass Spec. for compound 1C(ii): $MH^+$=539.

Step D:

Hydrolyze the product 3C(i) of Step C by dissolving in concentrated HCl and heating to about 100° C. for @ 16 hours. Cool the mixture, the neutralize with 1 M NaOH (aqueous). Extract with $CH_2Cl_2$, dry the extracts over $MgSO_4$, filter and concentrate in vacuo to the title compound. Mass Spec.: $MH^+$=466.9.

PREPARATIVE EXAMPLE 2

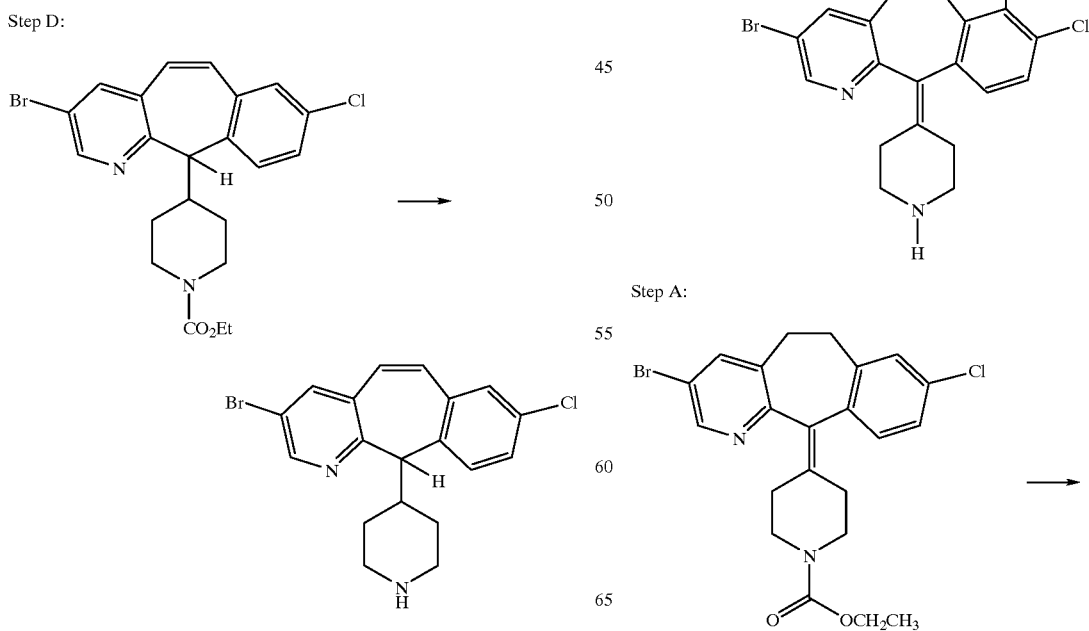

Step A:

-continued

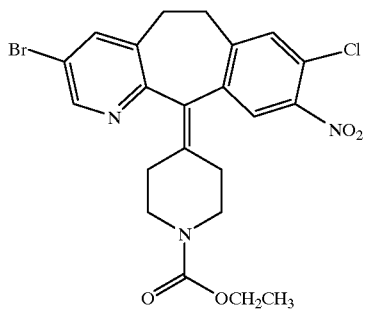

Combine 25.86 g (55.9 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 250 mL of concentrated $H_2SO_4$ at −5° C., then add 4.8 g (56.4 mmol) of $NaNO_3$ and stir for 2 hours. Pour the mixture into 600 g of ice and basify with concentrated $NH_4OH$ (aqueous). Filter the mixture, wash with 300 mL of water, then extract with 500 mL of $CH_2Cl_2$. Wash the extract with 200 mL of water, dry over $MgSO_4$, then filter and concentrate in vacuo to a residue. Chromatograph the residue (silica gel, 10% $EtOAc/CH_2Cl_2$) to give 24.4 g (86% yield) of the product. m.p.=165–167° C., Mass Spec.: $MH^+$=506 (CI). Elemental analysis: calculated—C, 52.13; H, 4.17; N, 8.29; found—C, 52,18; H, 4.51; N, 8.16.

Step B:

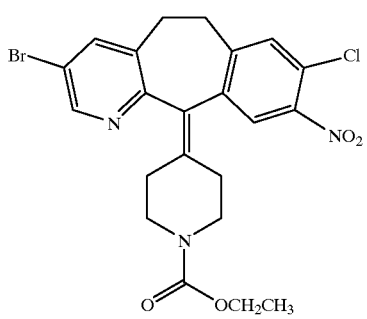

of acetone and filter to provide 19.79 g (85.6% yield) of the product. m.p.=236–237° C., Mass Spec.: $MH^+$=584 (CI). Elemental analysis: calculated—C, 45.11; H, 3.44; N, 7.17; found—C, 44.95; H, 3.57; N, 7.16

Step C:

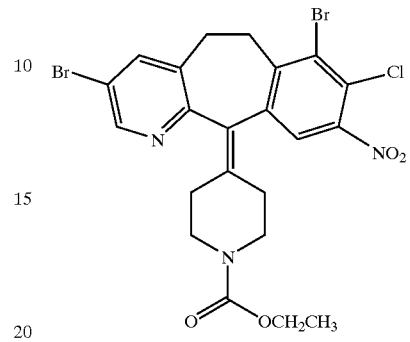

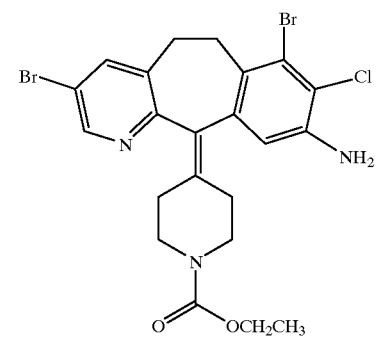

Combine 25 g (447 mmol) of Fe filings, 10 g (90 mmol) of $CaCl_2$ and a suspension of 20 g (34.19 mmol) of the product of Step B in 700 mL of 90:10 EtOH/water at 50° C. Heat the mixture at reflux overnight, filter through Celite® and wash the filter cake with 2×200 mL of hot EtOH. Combine the filtrate and washes, and concentrate in vacuo to a residue. Extract the residue with 600 mL of $CH_2Cl_2$, wash with 300 mL of water and dry over $MgSO_4$. Filter and concentrate in vacuo to a residue, then chromatograph (silica gel, 30% $EtOAc/CH_2Cl_2$) to give 11.4 g (60% yield) of the product. m.p.=211–212° C., Mass Spec.: $MH^+$=554 (CI). Elemental analysis: calculated—C, 47.55; H, 3.99; N, 7.56; found—C, 47.45; H, 4.31; N, 7.49.

Step D:

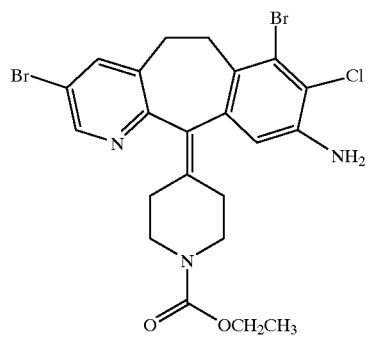

Combine 20 g (40.5 mmol) of the product of Step A and 200 mL of concentrated $H_2SO_4$ at 20° C., then cool the mixture to 0° C. Add 7.12 g (24.89 mmol) of 1,3-dibromo-5,5-dimethylhydantoin to the mixture and stir for 3 hours at 20° C. Cool to 0° C., add an additional 1.0 g (3.5 mmol) of the dibromohydantoin and stir at 20° C. for 2 hours. Pour the mixture into 400 g of ice, basify with concentrated $NH_4OH$ (aqueous) at 0° C., and collect the resulting solid by filtration. Wash the solid with 300 mL of water, slurry in 200 mL -continued

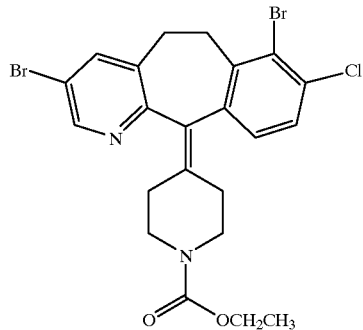

Slowly add (in portions) 20 g (35.9 mmol) of the product of Step C to a solution of 8 g (116 mmol) of NaNO₂ in 120 mL of concentrated HCl (aqueous) at −10° C. Stir the resulting mixture at 0° C. for 2 hours, then slowly add (dropwise) 150 mL (1.44 mole) of 50% H₃PO₂ at 0° C. over a 1 hour period. Stir at 0° C. for 3 hours, then pour into 600 g of ice and basify with concentrated NH₄OH (aqueous). Extract with 2×300 mL of CH₂Cl₂, dry the extracts over MgSO₄, then filter and concentrate in vacuo to a residue. Chromatograph the residue (silica gel, 25% EtOAc/hexanes) to give 13.67 g (70% yield) of the product. m.p.=163–165° C., Mass Spec.: MH⁺=539 (CI). Elemental analysis: calculated—C, 48.97; H, 4.05; N, 5.22; found—C, 48.86; H, 3.91; N, 5.18.

Step E:

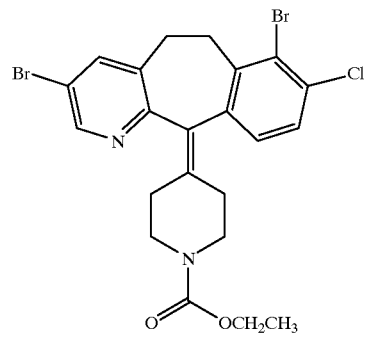

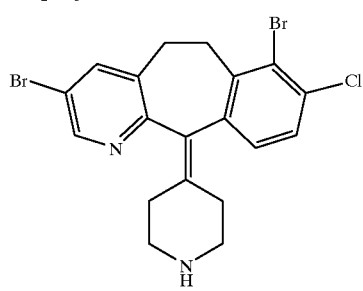

Combine 6.8 g (12.59 mmol) of the product of Step D and 100 mL of concentrated HCl (aqueous) and stir at 85° C. overnight. Cool the mixture, pour it into 300 g of ice and basify with concentrated NH₄OH (aqueous). Extract with 2×300 mL of CH₂Cl₂, then dry the extracts over MgSO₄. Filter, concentrate in vacuo to a residue, then chromatograph (silica gel, 10% MeOH/EtOAc+2% NH₄OH (aqueous)) to give 5.4 g (92% yield) of the title compound. m.p.= 172–174° C., Mass Spec.: MH⁺=467 (FAB). Elemental analysis: calculated—C, 48.69; H, 3.65; N, 5.97; found—C, 48.83; H, 3.80; N, 5.97

PREPARATIVE EXAMPLE 3

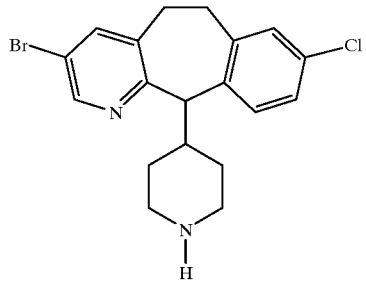

Step A:

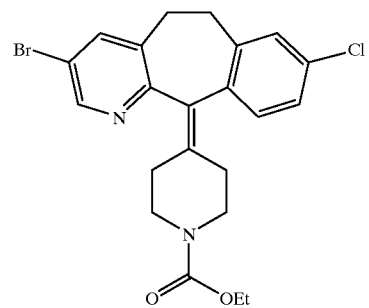

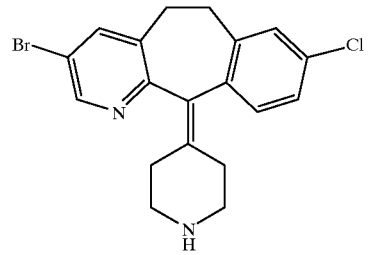

Hydrolyze 2.42 g of 4-(8-chloro-3-bromo-5,6-dihydro-11H-benzo[5,6]cyclohepta[1,2-b]pyridin-11-ylidene)-1-piperidine-1-carboxylic acid ethyl ester via substantially the same procedure as described in Preparative Example 1, Step D, to give 1.39 g (69% yield) of the product.

Step B:

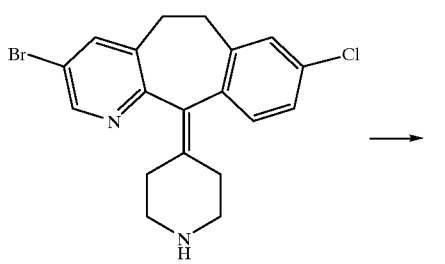

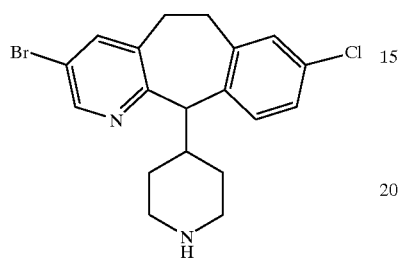

Combine 1 g (2.48 mmol) of the product of Step A and 25 mL of dry toluene, add 2.5 mL of 1 M DIBAL in toluene and heat the mixture at reflux. After 0.5 hours, add another 2.5 mL of 1 M DIBAL in toluene and heat at reflux for 1 hour. (The reaction is monitored by TLC using 50% MeOH/CH$_2$Cl$_2$+NH$_4$OH (aqueous).) Cool the mixture to room temperature, add 50 mL of 1 N HCl (aqueous) and stir for 5 min. Add 100 mL of 1 N NaOH (aqueous), then extract with EtOAc (3×150 mL). Dry the extracts over MgSO$_4$, filter and concentrate in vacuo to give 1.1 g of the title compound.

PREPARATIVE EXAMPLE 4

[racemic as well as (+)- and (-)-isomers]

Step A:

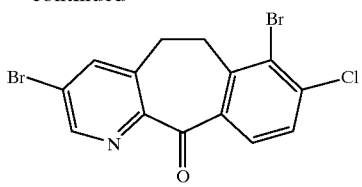

Combine 16.6 g (0.03 mole) of the product of Preparative Example 2, Step D, with a 3:1 solution of CH$_3$CN and water (212.65 mL CH$_3$CN and 70.8 mL of water) and stir the resulting slurry overnight at room temperature. Add 32.833 g (0.153 mole) of NaIO$_4$ and then 0.31 g (2.30 mmol) of RuO$_2$ and stir at room temperature give 1.39 g (69% yield) of the product. (The addition of RuO is accompanied by an exothermic reaction and the temperature climbs from 20° to 30° C.) Stir the mixture for 1.3 hrs. (temperature returned to 25° C. after about 30 min.), then filter to remove the solids and wash the solids with CH$_2$Cl$_2$. Concentrate the filtrate in vacuo to a residue and dissolve the residue in CH$_2$Cl$_2$. Filter to remove insoluble solids and wash the solids with CH$_2$Cl$_2$. Wash the filtrate with water, concentrate to a volume of about 200 mL and wash with bleach, then with water. Extract with 6 N HCl (aqueous). Cool the aqueous extract to 0° C. and slowly add 50% NaOH (aqueous) to adjust to pH=4 while keeping the temperature <30° C. Extract twice with CH$_2$Cl$_2$, dry over MgSO$_4$ and concentrate in vacuo to a residue. Slurry the residue in 20 mL of EtOH and cool to 0° C. Collect the resulting solids by filtration and dry the solids in vacuo to give 7.95 g of the product. $^1$H NMR (CDCl$_3$, 200 MHz): 8.7 (s, 1H); 7.85 (m, 6H); 7.5 (d, 2H); 3.45 (m, 2H), 3.15 (m, 2H).

Step B:

Combine 21.58 g (53.75 mmol) of the product of Step A and 500 mL of an anhydrous 1:1 mixture of EtOH and toluene, add 1.43 g (37.8 mmol) of NaBH$_4$ and heat the mixture at reflux for 10 min. Cool the mixture to 0° C., add 100 mL of water, then adjust to pH≈4–5 with 1 M HCl (aqueous) while keeping the temperature <10° C. Add 250 mL of EtOAc and separate the layers. Wash the organic layer with brine (3×50 mL) then dry over Na$_2$SO$_4$. Concentrate in vacuo to a residue (24.01 g) and chromatograph the residue (silica gel, 30% hexane/CH$_2$Cl$_2$) to give the product. Impure fractions were purified by rechromatography. A total of 18.57 g of the product was obtained. $^1$H NMR (DMSO-d$_6$, 400 MHz): 8.5 (s, 1H); 7.9 (s, 1H); 7.5 (d of d, 2H); 6.2 (s, 1H); 6.1 (s, 1H); 3.5 (m, 1H); 3.4 (m, 1H); 3.2 (m, 2H).

Step C:

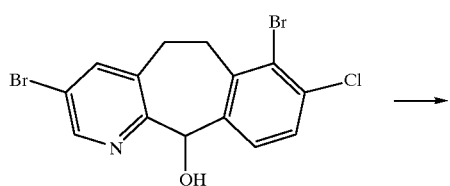

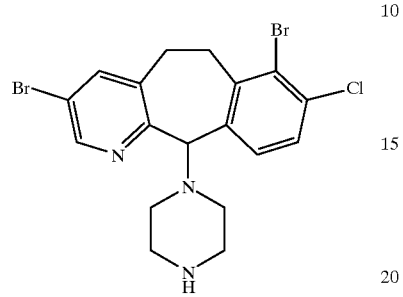

Combine 18.57 g (46.02 mmol) of the product of Step B and 500 mL of CHCl$_3$, then add 6.70 mL (91.2 mmol) of SOCl$_2$, and stir the mixture at room temperature for 4 hrs. Add a solution of 35.6 g (0.413 mole) of piperazine in 800 mL of THF over a period of 5 min. and stir the mixture for 1 hr. at room temperature. Heat the mixture at reflux overnight, then cool to room temperature and dilute the mixture with 1 L of CH$_2$Cl$_2$. Wash with water (5×200 mL), and extract the aqueous wash with CHCl$_3$ (3×100 mL). Combine all of the organic solutions, wash with brine (3×200 mL) and dry over MgSO$_4$. Concentrate in vacuo to a residue and chromatograph (silica gel, gradient of 5%, 7.5%, 10% MeOH/CH$_2$Cl$_2$+NH$_4$OH) to give 18.49 g of the title compound as a racemic mixture.

Step D - Separation of Enantiomers:

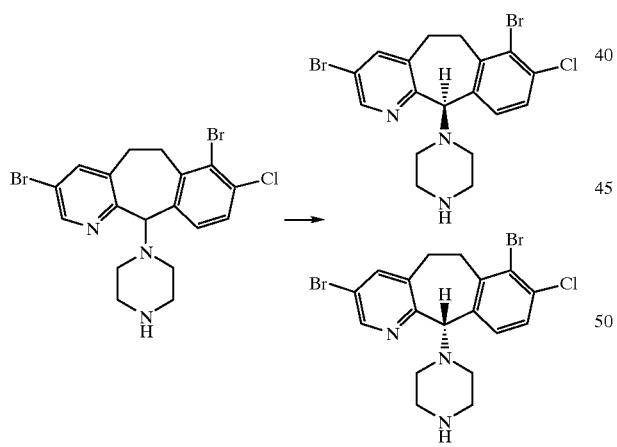

The racemic title compound of Step C is separated by preparative chiral chromatography (Chiralpack AD, 5 cm×50 cm column, flow rate 100 mL/min., 20% iPrOH/hexane+0.2% diethylamine), to give 9.14 g of the (+)-isomer and 9.30 g of the (−)-isomer.

Physical chemical data for (+)-isomer: m.p.=74.5°–77.5° C.; Mass Spec. MH$^+$=471.9; [α]$_D^{25}$=+97.4° (8.48 mg/2 mL MeOH).

Physical chemical data for (−)-isomer: m.p.=82.9°–84.5° C.; Mass Spec. MH$^+$=471.8; [α]$_D^{25}$=−97.4° (8.32 mg/2 mL MeOH).

PREPARATIVE EXAMPLE 5

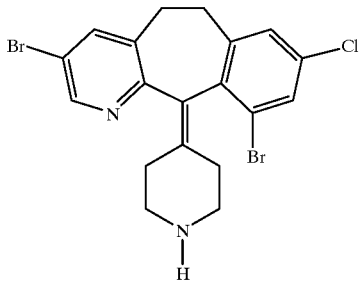

Step A:

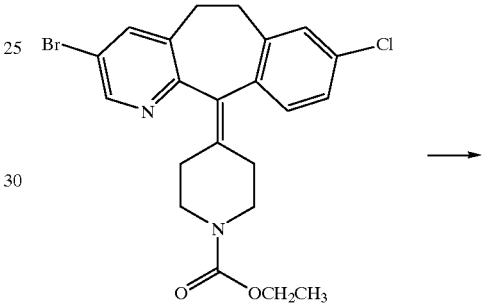

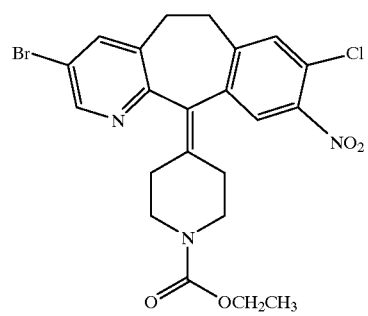

Combine 15 g (38.5 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 150 mL of concentrated H$_2$SO$_4$ at −5° C., then add 3.89 g (38.5 mmol) of KNO$_3$ and stir for 4 hours. Pour the mixture into 3 L of ice and basify with 50% NaOH (aqueous). Extract with CH$_2$Cl$_2$, dry over MgSO$_4$, then filter and concentrate in vacuo to a residue. Recrystallize the residue from acetone to give 6.69 g of the product. $^1$H NMR (CDCl$_3$, 200 MHz): 8.5 (s, 1H); 7.75 (s, 1H); 7.6 (s, 1H); 7.35 (s, 1H); 4.15 (q, 2H); 3.8 (m, 2H); 3.5–3.1 (m, 4H); 3.0–2.8 (m, 2H); 2.6–2.2 (m, 4H); 1.25 (t, 3H).

Step B:

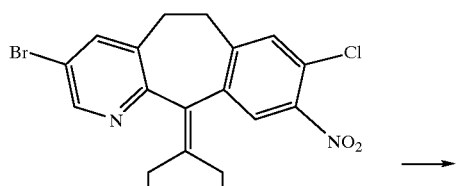

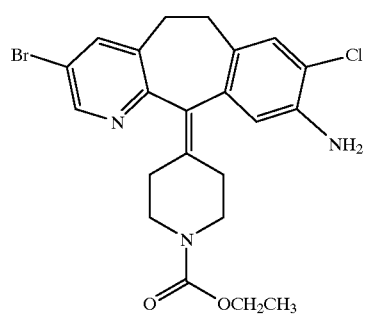

Combine 6.69 g (13.1 mmol) of the product of Step A and 100 mL of 85% EtOH/water, then add 0.66 g (5.9 mmol) of $CaCl_2$ and 6.56 g (117.9 mmol) of Fe and heat the mixture at reflux overnight. Filter the hot reaction mixture through celite® and rinse the filter cake with hot EtOH. Concentrate the filtrate in vacuo to give 7.72 g of the product. Mass Spec.: $MH^+=478.0$ Step C:

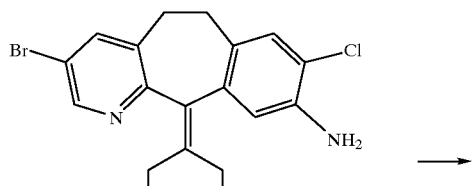

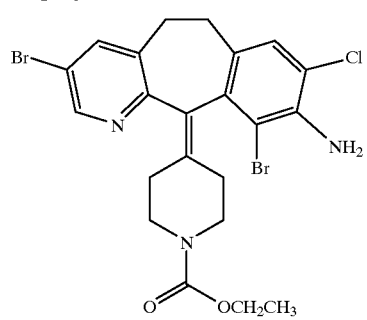

Combine 7.70 g of the product of Step B and 35 mL of HOAc, then add 45 mL of a solution of $Br_2$ in HOAc and stir the mixture at room temperature overnight. Add 300 mL of 1 N NaOH (aqueous), then 75 mL of 50% NaOH (aqueous) and extract with EtOAc. Dry the extract over $MgSO_4$ and concentrate in vacuo to a residue. Chromatograph the residue (silica gel, 20%–30% EtOAc/hexane) to give 3.47 g of the product (along with another 1.28 g of partially purified product). Mass Spec.: $MH^+=555.9$.

$^1$H NMR ($CDCl_3$, 300 MHz): 8.5 (s, 1H); 7.5 (s, 1H); 7.15 (s, 1H); 4.5 (s, 2H); 4.15 (m, 3H); 3.8 (br s, 2H); 3.4–3.1 (m, 4H); 9–2.75 (m, 1H); 2.7–2.5 (m, 2H); 2.4–2.2 (m, 2H); 1.25 (m, 3H).

Step D:

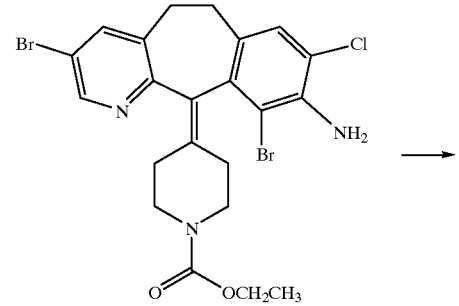

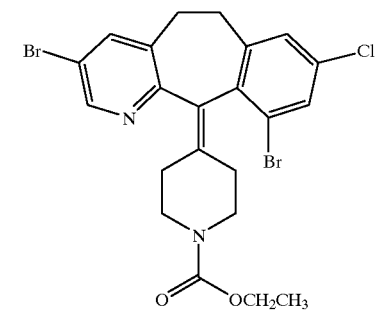

Combine 0.557 g (5.4 mmol) of t-butylnitrite and 3 mL of DMF, and heat the mixture at to 60°–70° C. Slowly add (dropwise) a mixture of 2.00 g (3.6 mmol) of the product of Step C and 4 mL of DMF, then cool the mixture to room temperature. Add another 0.64 mL of t-butylnitrite at 40° C. and reheat the mixture to 60°–70° C. for 0.5 hrs. Cool to room temperature and pour the mixture into 150 mL of water. Extract with $CH_2Cl_2$, dry the extract over $MgSO_4$ and concentrate in vacuo to a residue. Chromatograph the residue (silica gel, 10%–20% EtOAc/hexane) to give 0.74 g of the product. Mass Spec.: $MH^+=541.0$.

$^1$H NMR (CDCl3, 200 MHz): 8.52 (s, 1H); 7.5 (d, 2H); 7.2 (s, 1H); 4.15 (q, 2H); 3.9–3.7 (m, 2H); 3.5–3.1 (m, 4H); 3.0–2.5 (m, 2H); 2.4–2.2 (m, 2H); 2.1–1.9 (m, 2H); 1.26 (t, 3H).

Step E:

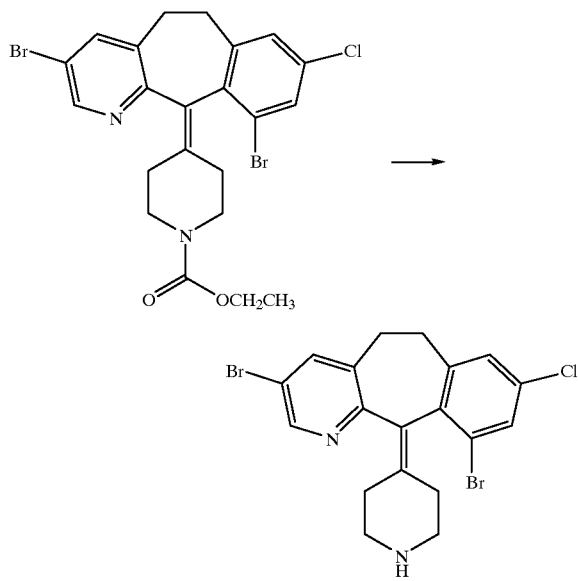

Combine 0.70 g (1.4 mmol) of the product of Step D and 8 mL of concentrated HCl (aqueous) and heat the mixture at reflux overnight. Add 30 mL of 1 N NaOH (aqueous), then 5 mL of 50% NaOH (aqueous) and extract with $CH_2Cl_2$. Dry the extract over $MgSO_4$ and concentrate in vacuo to give 0.59 g of the title compound. Mass Spec.: $M^+$=468.7. m.p.=123.9°–124.2° C.

PREPARATIVE EXAMPLE 6

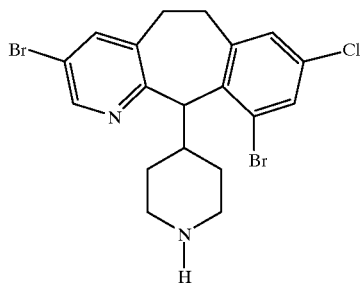

[racemic as well as (+)- and (-)-isomers]

Step A:

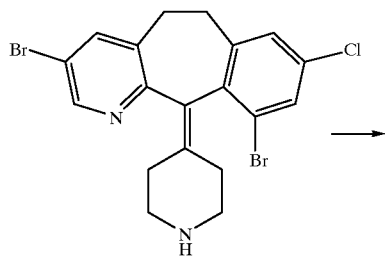

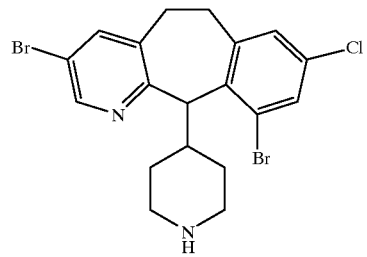

Prepare a solution of 8.1 g of the title compound from Preparative Example 5, Step E, in toluene and add 17.3 mL of a 1M solution of DIBAL in toluene. Heat the mixture at reflux and slowly add (dropwise) another 21 mL of 1 M DIBAL/toluene solution over a period of 40 min. Cool the reaction mixture to about 0° C. and add 700 mL of 1 M HCl (aqueous). Separate and discard the organic phase. Wash the aqueous phase with $CH_2Cl_2$, discard the extract, then basify the aqueous phase by adding 50% NaOH (aqueous). Extract with $CH_2Cl_2$, dry the extract over $MgSO_4$ and concentrate in vacuo to give 7.30 g of the title compound, which is a racemic mixture of enantiomers.

Step B - Separation of Enantiomers:

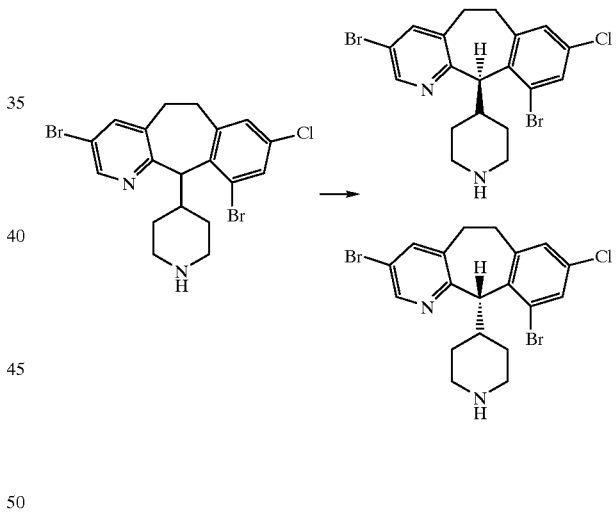

The racemic title compound of Step A is separated by preparative chiral chromatography (Chiralpack AD, 5 cm×50 cm column, using 20% iPrOH/hexane+0.2% diethylamine), to give the (+)-isomer and the (-)-isomer of the title compound.

Physical chemical data for (+)-isomer: m.p.=148.8° C.; Mass Spec. $MH^+$=469; $[\alpha]_D^{25}$=+65.6° (12.93 mg/2 mL MeOH).

Physical chemical data for (-)-isomer: m.p.=112° C.; Mass Spec. $MH^+$=469; $[\alpha]_D^{25}$=-65.2° (3.65 mg/2 mL MeOH).

PREPARATIVE EXAMPLE 7

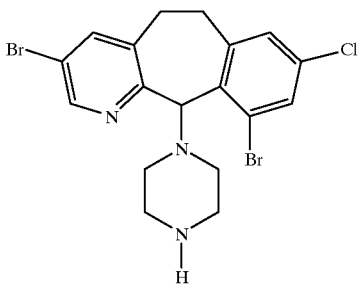

[racemic as well as (+)- and (-)-isomers]

Step A:

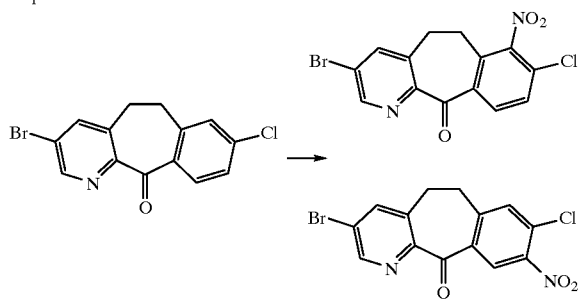

Combine 40.0 g (0.124 mole) of the starting ketone and 200 mL of $H_2SO_4$ and cool to 0° C. Slowly add 13.78 g (0.136 mole) of $KNO_3$ over a period of 1.5 hrs., then warm to room temperature and stir overnight. Work up the reaction using substantially the same procedure as described for Preparative Example 2, Step A. Chromatograph (silica gel, 20%, 30%, 40%, 50% EtOAc/hexane, then 100% EtOAc) to give 28 g of the 9-nitro product, along with a smaller quantity of the 7-nitro product and 19 g of a mixture of the 7-nitro and 9-nitro compounds.

Step B:

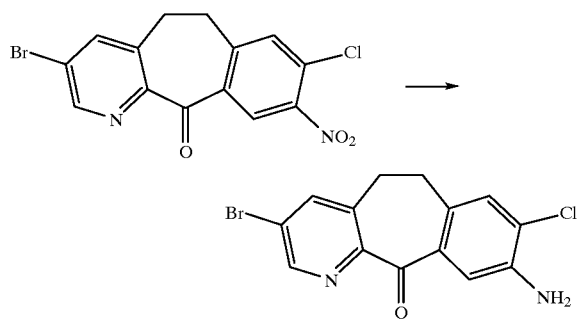

React 28 g (76.2 mmol) of the 9-nitro product of Step A, 400 mL of 85% EtOH/water, 3.8 g (34.3 mmol) of $CaCl_2$ and 38.28 g (0.685 mole) of Fe using substantially the same procedure as described for Preparative Example 2, Step C, to give 24 g of the product Step C:

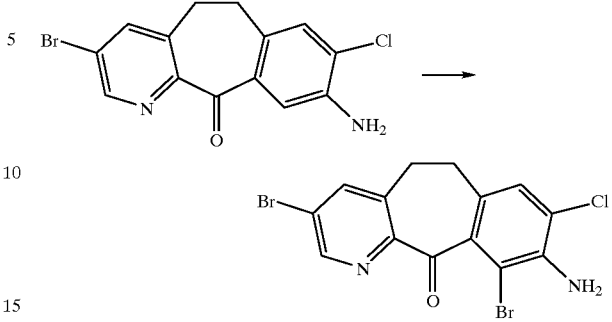

Combine 13 g (38.5 mmol) of the product of Step B, 140 mL of HOAc and slowly add a solution of 2.95 mL (57.8 mmol) of $Br_2$ in 10 mL of HOAc over a period of 20 min. Stir the reaction mixture at room temperature, then concentrate in vacuo to a residue. Add $CH_2Cl_2$ and water, then adjust to pH=8–9 with 50% NaOH (aqueous). Wash the organic phase with water, then brine and dry over $Na_2SO_4$. Concentrate in vacuo to give 11.3 g of the product.

Step D:

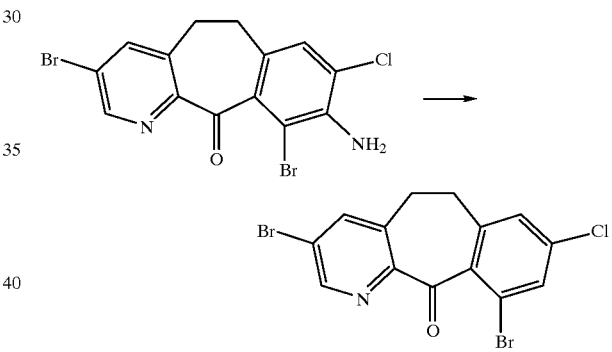

Cool 100 mL of concentrated HCl (aqueous) to 0° C., then add 5.61 g (81.4 mmol) of $NaNO_2$ and stir for 10 min. Slowly add (in portions) 11.3 g (27.1 mmol) of the product of Step C and stir the mixture at 0°–3° C. for 2.25 hrs. Slowly add (dropwise) 180 mL of 50% $H_3PO_2$ (aqueous) and allow the mixture to stand at 0° C. overnight. Slowly add (dropwise) 150 mL of 50% NaOH over 30 min., to adjust to pH=9, then extract with $CH_2Cl_2$. Wash the extract with water, then brine and dry over $Na_2SO_4$. Concentrate in vacuo to a residue and chromatograph (silica gel, 2% EtOAc/$CH_2Cl_2$) to give 8.6 g of the product.

Step E:

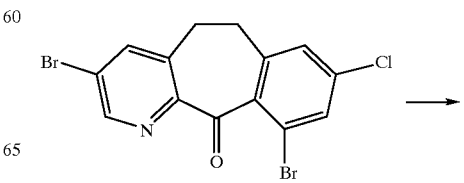

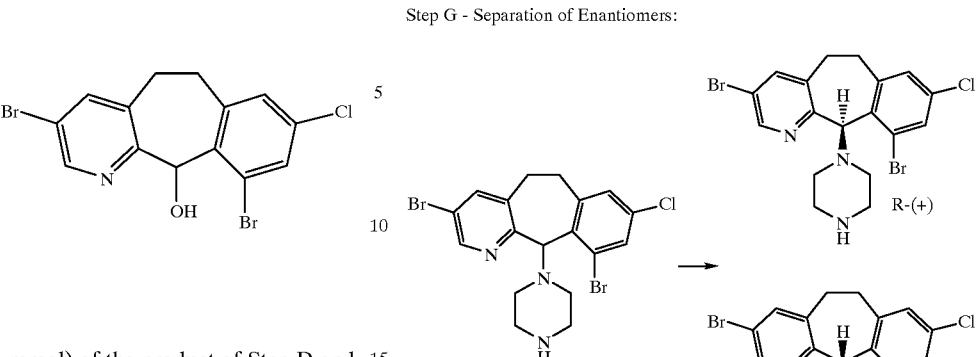

Combine 8.6 g (21.4 mmol) of the product of Step D and 300 mL of MeOH and cool to 0°–2° C. Add 1.21 g (32.1 mmol) of NaBH$_4$ and stir the mixture at ~0° C. for 1 hr. Add another 0.121 g (3.21 mmol) of NaBH$_4$, stir for 2 hr. at 0° C., then let stand overnight at 0° C. Concentrate in vacuo to a residue then partition the residue between CH$_2$Cl$_2$ and water. Separate the organic phase and concentrate in vacuo (50° C.) to give 8.2 g of the product.

Step F:

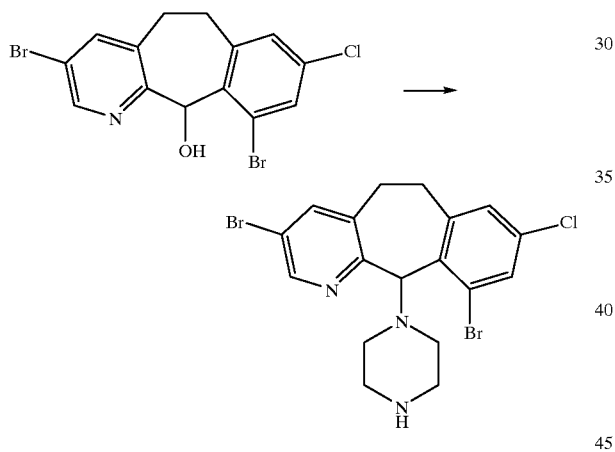

Combine 8.2 g (20.3 mmol) of the product of Step E and 160 mL of CH$_2$Cl$_2$, cool to 0° C., then slowly add (dropwise) 14.8 mL (203 mmol) of SOCl$_2$ over a 30 min. period. Warm the mixture to room temperature and stir for 4.5 hrs., then concentrate in vacuo to a residue, add CH$_2$Cl$_2$ and wash with 1 N NaOH (aqueous) then brine and dry over Na$_2$SO$_4$. Concentrate in vacuo to a residue, then add dry THF and 8.7 g (101 mmol) of piperazine and stir at room temperature overnight. Concentrate in vacuo to a residue, add CH$_2$Cl$_2$, and wash with 0.25 N NaOH (aqueous), water, then brine. Dry over Na$_2$SO$_4$ and concentrate in vacuo to give 9.46 g of the crude product. Chromatograph (silica gel, 5% MeOH/CH$_2$Cl$_2$+NH$_3$) to give 3.59 g of the title compound, as a racemate. $^1$H NMR (CDCl$_3$, 200 MHz): 8.43 (d, 1H); 7.55 (d, 1H); 7.45 (d, 1H); 7.11 (d, 1H); 5.31 (s, 1H); 4.86–4.65 (m, 1H); 3.57–3.40 (m, 1H); 2.98–2.55 (m, 6H); 2.45–2.20 (m, 5H).

Step G - Separation of Enantiomers:

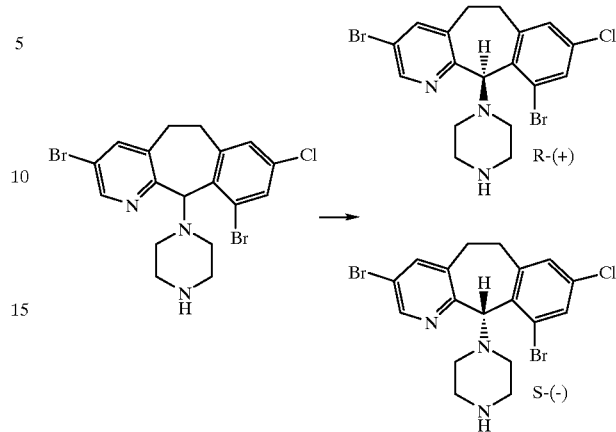

The racemic title compound from Step F (5.7 g) is chromatographed as described for Preparative Example 4, Step D, using 30% iPrOH/hexane+0.2% diethylamine, to give 2.88 g of the R-(+)-isomer and 2.77 g of the S-(−)-isomer of the title compound.

Physical chemical data for the R-(+)-isomer: Mass Spec. MH$^+$=470.0; $[\alpha]_D^{25}$=+12.1° (10.9 mg/2 mL MeOH).

Physical chemical data for the S-(−)-isomer: Mass Spec. MH$^+$=470.0; $[\alpha]_D^{25}$=−13.2° (11.51 mg/2 mL MeOH).

PREPARATIVE EXAMPLE 8

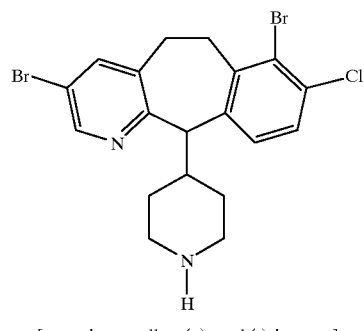

[racemic as well as (+)- and (−)-isomers]

Step A:

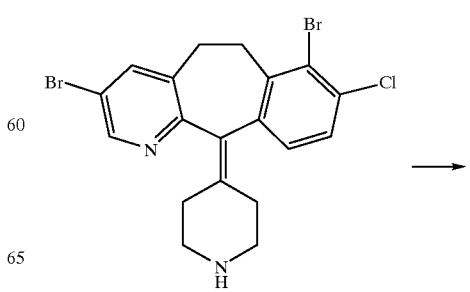

-continued

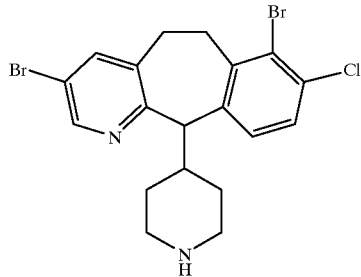

Combine 13 g (33.3 mmol) of the title compound from Preparative Example 2, Step E, and 300 mL of toluene at 20° C., then add 32.5 mL (32.5 mmol) of a 1 M solution of DIBAL in toluene. Heat the mixture at reflux for 1 hr., cool to 20° C., add another 32.5 mL of 1 M DIBAL solution and heat at reflux for 1 hr. Cool the mixture to 20° C. and pour it into a mixture of 400 g of ice, 500 mL of EtOAc and 300 mL of 10% NaOH (aqueous). Extract the aqueous layer with $CH_2Cl_2$ (3×200 mL), dry the organic layers over $MgSO_4$, then concentrate in vacuo to a residue. Chromatograph (silica gel, 12% $MeOH/CH_2Cl_2$+4% $NH_4OH$) to give 10.4 g of the title compound as a racemate. Mass Spec.: $MH^+$=469 (FAB). Partial $^1H$ NMR ($CDCl_3$, 400 MHz): 8.38 (s, 1H); 7.57 (s, 1H); 7.27 (d, 1H); 7.06 (d, 1H); 3.95 (d, 1H).

The racemic title compound of Step A is separated by preparative chiral chromatography (Chiralpack AD, 5 cm×50 cm column, using 5% iPrOH/hexane+0.2% diethylamine), to give the (+)-isomer and the (−)-isomer of the title compound.

Physical chemical data for (+)-isomer: Mass Spec. $MH^+$= 469 (FAB); $[\alpha]_D^{25}$=+43.5° (c=0.402, EtOH); partial $^1H$ NMR ($CDCl_3$, 400 MHz): 8.38 (s, 1H); 7.57 (s, 1H); 7.27 (d, 1H); 7.05 (d, 1H); 3.95 (d, 1H).

Physical chemical data for (−)-isomer: Mass Spec. $MH^+$= 469 (FAB); $[\alpha]_D^{25}$=−41.8° (c=0.328 EtOH); partial $^1H$ NMR ($CDCl_3$, 400 MHz): 8.38 (s, 1H); 7.57 (s, 1H); 7.27 (d, 1H); 7.05 (d, 1H); 3.95 (d, 1H).

PREPARATIVE EXAMPLE 9

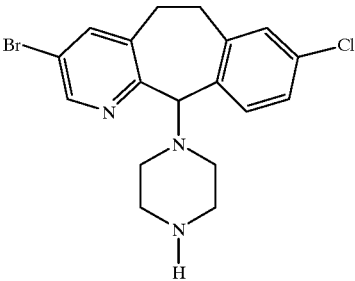

[racemic as well as R-(+)- and S-(−)-isomers]

Step B - Separation of Enantiomers:

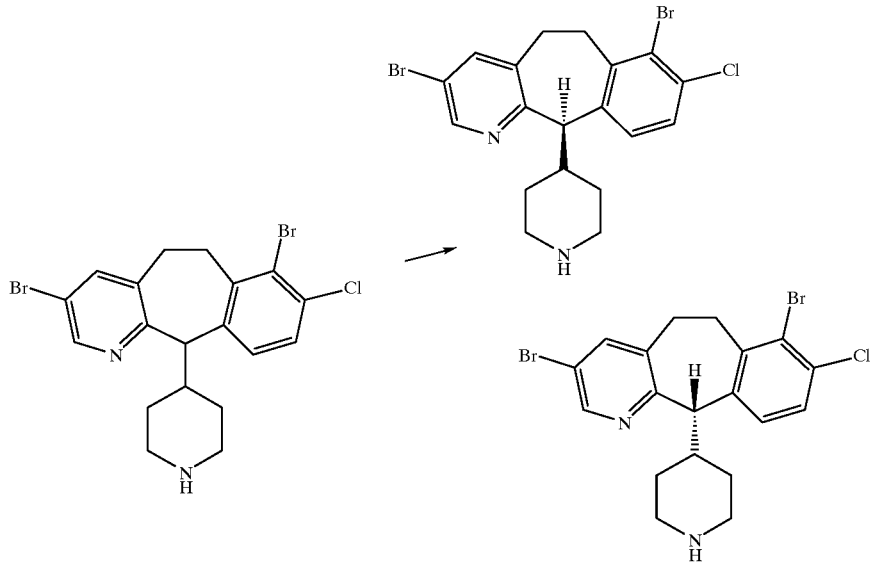

The compound

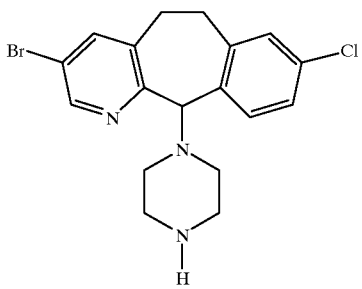

is prepared according to the procedures of Preparative Example 40 of WO 95/10516 (published Apr. 20, 1995), by following the procedures described in Example 193 of WO 95/10516.

The (+)- and (−)-isomers can be separated by following essentially the same procedure as Step D of Preparative Example 4.

Physical chemical data for the R-(+)-isomer: $^{13}$C NMR (CDCl$_3$): 155.8 (C); 146.4 (CH); 140.5 (CH); 140.2 (C); 136.2 (C); 135.3 (C); 133.4 (C); 132.0 (CH); 129.9 (CH); 125.6 (CH); 119.3 (C); 79.1 (CH); 52.3 (CH$_2$); 52.3 (CH$_2$); 45.6 (CH$_2$); 45.6 (CH$_2$); 30.0 (CH$_2$); 29.8 (CH$_2$). $[\alpha]_D^{25}$=+25.8° (8.46 mg/2 mL MeOH).

Physical chemical data for the S-(−)-isomer: $^{13}$C NMR (CDCl$_3$): 155.9 (C); 146.4 (CH); 140.5 (CH); 140.2 (C); 136.2 (C); 135.3 (C); 133.3 (C); 132.0 (CH); 129.9 (CH); 125.5 (CH); 119.2 (C); 79.1 (CH); 52.5 (CH$_2$); 52.5 (CH$_2$); 45.7 (CH$_2$); 45.7 (CH$_2$); 30.0 (CH$_2$); 29.8 (CH$_2$). $[\alpha]_D^{25}$=−27.9° (8.90 mg/2 mL MeOH).

PREPARATIVE EXAMPLE 10

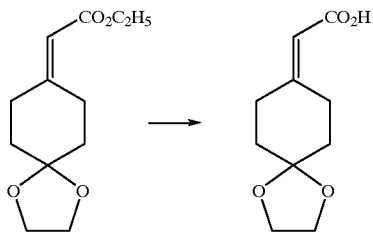

Dissolve 0.1 g (0.449 mmol) of ethyl 2-[4,4-(ethylenedioxy)-cyclohexylidene]acetate (Tetrahedron (1995) 51, 10259) in 2 mL of ethanol containing 0.074 g (1.32 mmol) of potassium hydroxide. Stir for 2 hr at 60° C., concentrate under vacuum, and dissolve the residue in 20 mL of water. Adjust to pH 4 with 1 N HCl and extract with ethyl acetate. Dry over magnesium sulfate and concentrate under vacuum to yield 0.56 g of the product as a white solid.

PREPARATIVE EXAMPLE 11

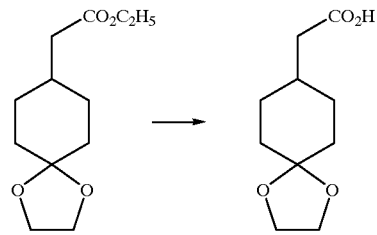

Follow the procedure of Preparative Example 1, but using ethyl 2-[4,4-(ethylenedioxy)cyclohexyl]acetate (Tetrahedron 995) 51, 10259) instead of 2-[4,4-(ethylenedioxy)cycloxylidene]acetate to obtain the product as a white solid.

PREPARATIVE EXAMPLE 12

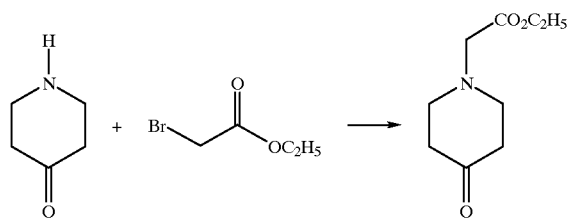

Dissolve 10 g (5.1 mmol) of 4-piperidone in 150 mL of acetonitrile containing 8.99 g (65.1 mmole) of K$_2$CO$_3$. Stir under nitrogen and add 7.22 mL of ethyl bromoacetate. Reflux for 2 hr, cool to room temperature and filter. Concentrate the filtrate under vacuum and partition the residue between water and ethyl acetate. Dry the organic layer over magnesium sulfate and concentrate under vacuum to give the product as a brown oil.

PREPARATIVE EXAMPLE 13

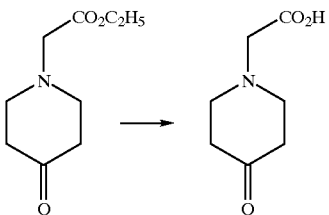

Follow the procedure of Preparative Example 10, but using the product of Preparative Example 12 instead of ethyl 2-[4,4-(ethylenedioxy)cyclohexylidene]acetate to obtain the product as a brown solid.

PREPARATIVE EXAMPLE 14

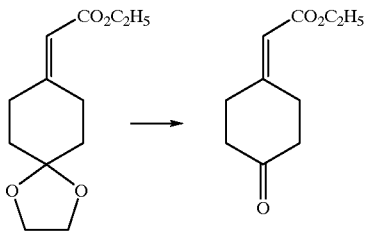

Dissolve 0.48 g (2.12 mmol) of ethyl 2-[4,4-(ethylenedioxy)cyclohexylidene]acetate (Tetrahedron (1995) 51, 10259) in 10 mL of ethanol containing 0.4 mL of 20% aqueous sulfuric acid. Stir for 18 hr at 25° C. and 2 hr at 60° C. Concentrate under vacuum, and dissolve the residue in 20 mL of water. Adjust to pH 7 with aqueous $NaHCO_3$ and extract with ethyl ether. Dry the organic layer over magnesium sulfate and concentrate under vacuum to yield 0.306 g of the product as an oil.

PREPARATIVE EXAMPLE 15

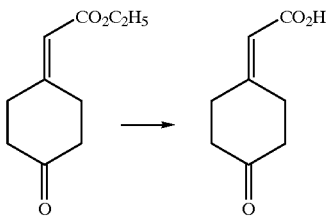

Follow the procedure of Preparative Example 10, but using the product of Preparative Example 14 instead of ethyl 2-[4,4-(ethylenedioxy)cyclohexylidene]-acetate to obtain the product as a yellow solid.

PREPARATIVE EXAMPLE 16

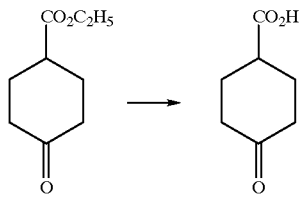

Follow the procedure of Preparative Example 10, but using commercially available ethyl 4-oxocyclohexylcarboxylate instead of ethyl 2-[14,4-(ethylenedioxy)cyclohexylidene]acetate to obtain the product as an oil (J. Chem. Soc. (1950) 1379).

PREPARATIVE EXAMPLE 17

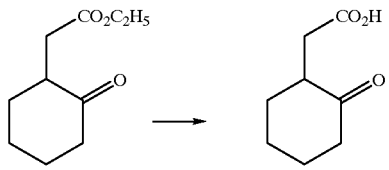

Follow the procedure of Preparative Example 10, but using commercially available ethyl 2-cyclohexanoneacetate instead of ethyl 2-[14,4-(ethylenedioxy)cyclohexylidene] acetate to obtain the product as an oil.

PREPARATIVE EXAMPLE 18

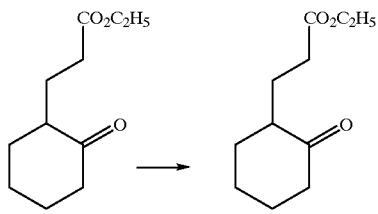

Follow the procedure of Preparative Example 10, but using commercially available ethyl 3-(2-oxocyclohexyl) propionate instead of ethyl 2-[4,4-(ethylenedioxy) cyclohexylidene]acetate to obtain the product as a white solid.

PREPARATIVE EXAMPLE 19

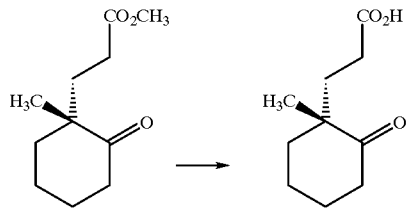

Follow the procedure of Preparative Example 10, but using commercially available methyl (R)-(+)-1-methyl-2-oxo-cyclohexanepropionate instead of ethyl 2-[4,4-(ethylenedioxy)cyclohexylidene]acetate to obtain the product as an oil.

EXAMPLE 1

(+)-4-(3,10-Dibromo-8-chloro-6,11-dihydro-5H-benzo[5,6]cyclohepta[1,2-b]pyridine-11(R)-yl-1-[(4-oxocyclohexyl)acetyl]piperidine

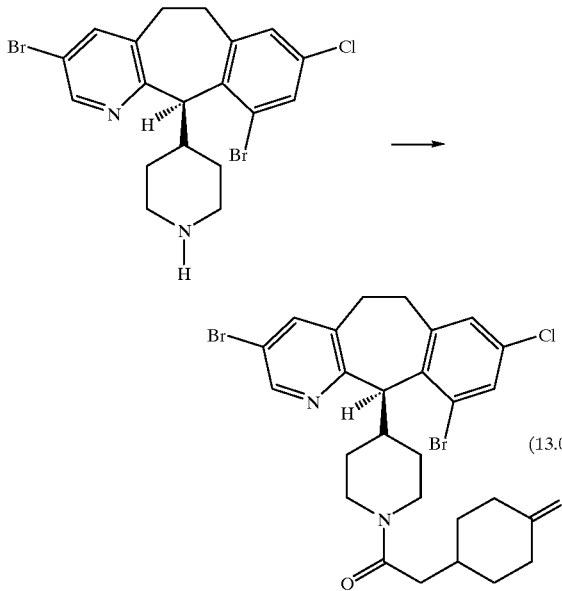

Dissolve the (+) product of Preparative Example 6, Step B, (2.0 g, 4.25 mmol) in 100 mL of DMF, stir at room temperature and add 0.86 g (8.5 mmol) of 4-methylmorpholine, 1.1 g (5.53 mmol) of DEC, 0.75 g (5.53 mmol) of HOBT and 0.86 g (5.52 mmole) of 4-oxocyclohexylacetic acid (Tetrahedron (1995) 51, 10259 and Helv. Chim. Acta, (1957) 40, 1999). Stir the mixture at room temperature for 18 hr, then concentrate in vacuo to a residue and partition between ethyl acetate and water. Wash the organic phase with aqueous sodium bicarbonate solution then brine. Dry the organic phase over magnesium sulfate, filter and concentrate in vacuo to a residue. Chromatograph the residue on silica gel, eluting with ethyl acetate—hexane (75%–25%) to yield the product (1.74 g) as a white solid. M.p.=123.8°–125.1° C., Mass Spec.: MH+=609. $[\alpha]_D^{24.6°C.}$=+61.3°, c=0.166, methylene chloride.

EXAMPLE 2

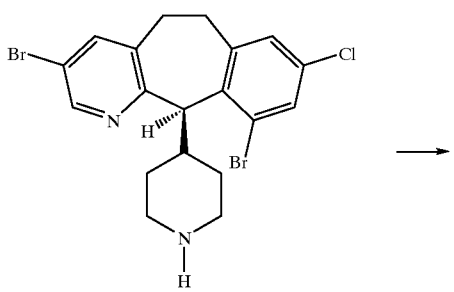

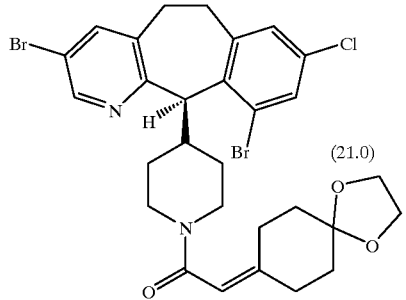

Following the procedure of Example 1 but using the product of Preparative Example 10 instead of 4-oxocyclohexylacetic acid, obtain the product as a white solid mp=136.8–138.7° C.

EXAMPLE 3

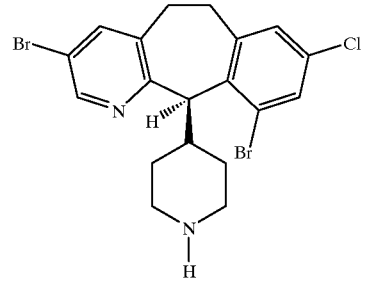

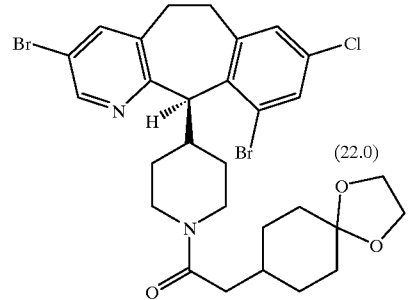

Following the procedure of Example 1 but using the product of Preparative Example 11 instead of 4-oxocyclohexylacetic acid, obtain the product as a white solid mp=128.4–133° C.

EXAMPLE 4

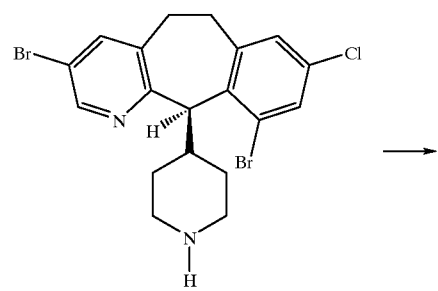

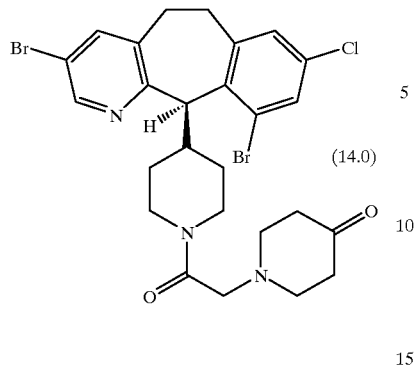

(14.0)

Following the procedure of Example 1 but using the product of Preparative Example 13 instead of 4-oxocyclohexylacetic acid, obtain the product as a white solid mp=121.3–125.8° C.

EXAMPLE 5

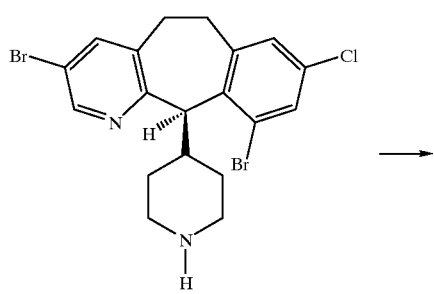

→

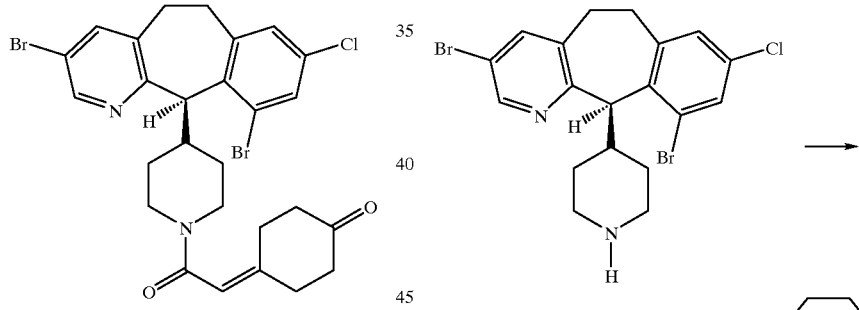

Following the procedure of Example 1 but using the product of Preparative Example 15 instead of 4-oxocyclohexylacetic acid, obtain the product as a white solid mp=208.1–209.9° C.

EXAMPLE 6

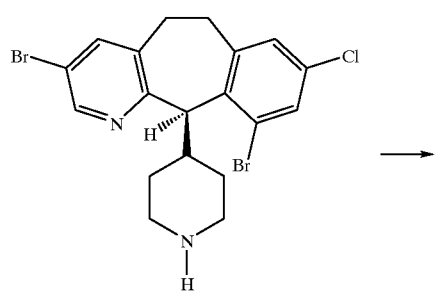

→

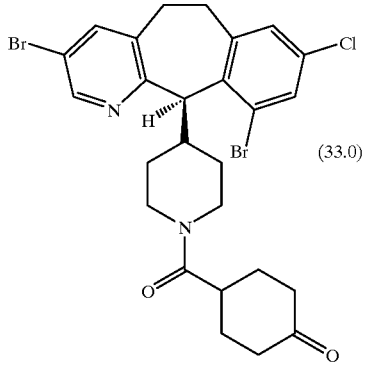

(33.0)

Following the procedure of Example 1 but using the product of Preparative Example 16 instead of 4-oxocyclohexylacetic acid, obtain the product as a white solid mp=125.4–127.7° C.

EXAMPLE 7

Following the procedure of Example 1 but using the product of Preparative Example 17 instead of 4-oxocyclohexylacetic acid, obtain the product as a white solid mp=118.5–122.4° C.

EXAMPLE 8

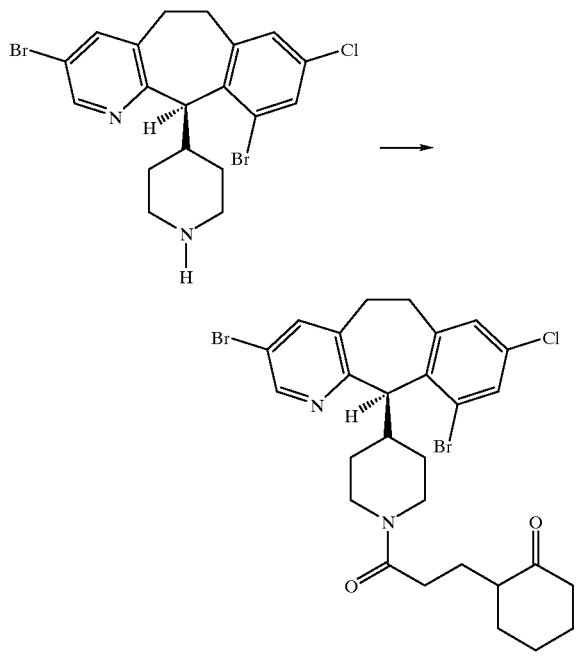

Following the procedure of Example 1 but using the product of Preparative Example 9 instead of 4-oxocyclohexylacetic acid, obtain the product as a white solid mp=110.5–114.8° C.

EXAMPLE 9

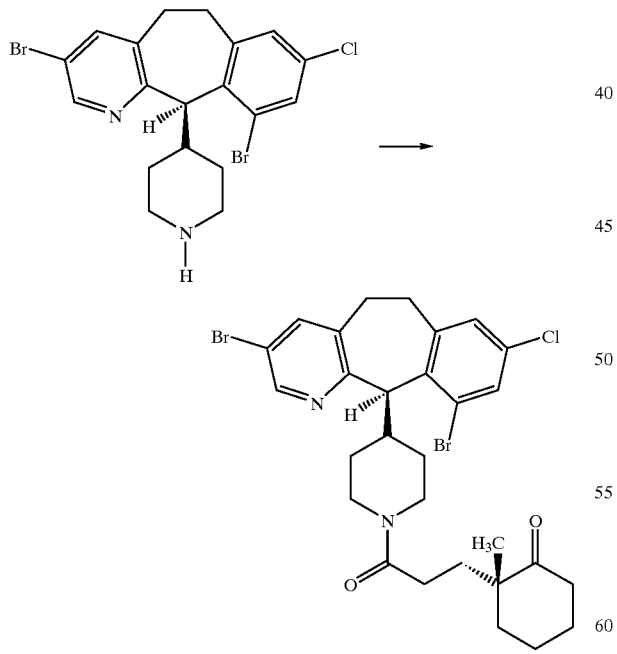

Following the procedure of Example 1 but using the product of Preparative Example 19 instead of 4-oxocyclohexylacetic acid, obtain the product as a white solid mp=113.5–116.8° C.

EXAMPLES 10 AND 11

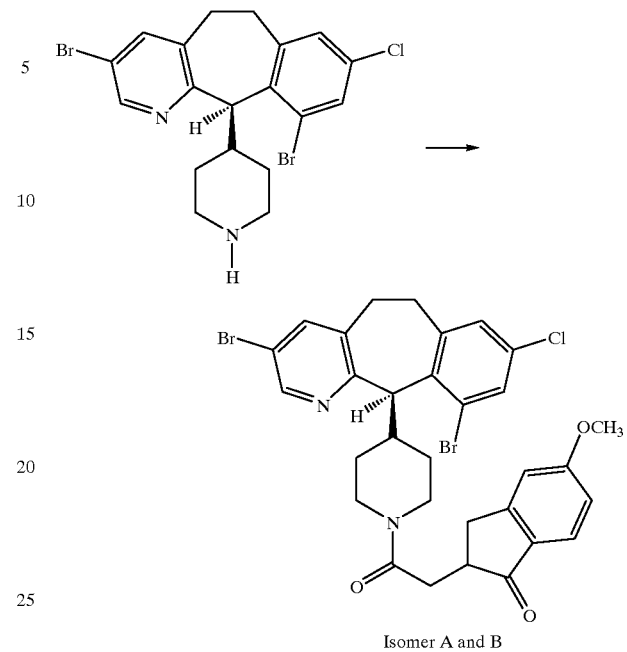

Following the procedure of Example 1 but using commercially available 5-methoxy-1-indanone-3-acetic acid instead of 4-oxo-cyclohexylacetic acid, to obtain the products: Isomer A (Example 10) as a white solid mp=140.4–145.3° C., and Isomer B (Example 11) as a white solid mp=135.1–139.4° C.

EXAMPLE 12

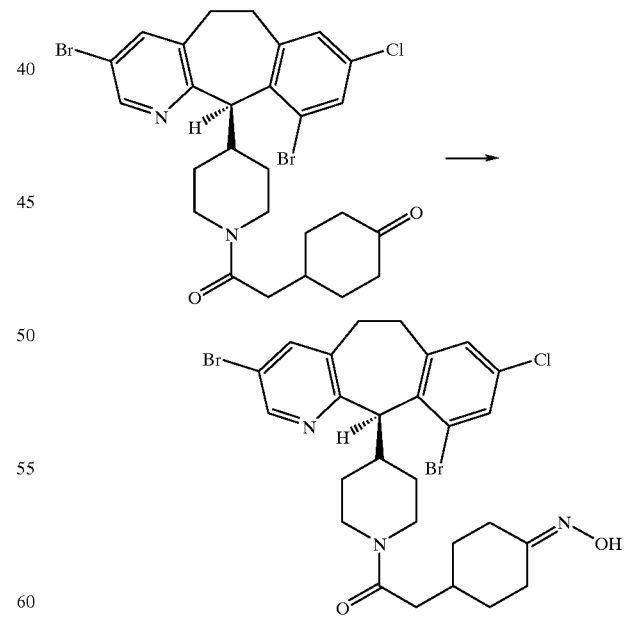

Dissolve 0.5 g (0.821 mmol) of the product of Example 1 in 5 mL of pyridine then add 0.285 g (4.11 mmol) of hydroxylamine hydrochloride and stir at 25° C. under nitrogen for 18 hr. Pour the reaction into 40 mL of water and extract with three 50 mL portions of dichloromethane. The combined organic layers were dried kover magnesium sulfate and concentrated under vacuum. The resulting residue was chromatographed on silica gel using ethyl acetate-hexane (80%–20%) to give the product as a white solid mp=140.3–143.5° C.

EXAMPLE 13

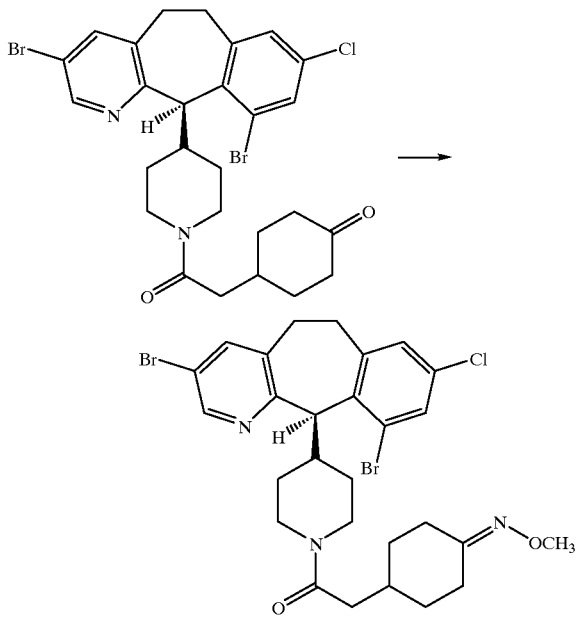

Follow the procedure of Example 12, but using methoxyamine hydrochloride instead of hydroxylamine hydrochloride, and chromatograph on silica gel using ethyl acetate-hexame (90%–10%) to obtain the product as a white solid mp=102.1–105.4° C.

EXAMPLE 14

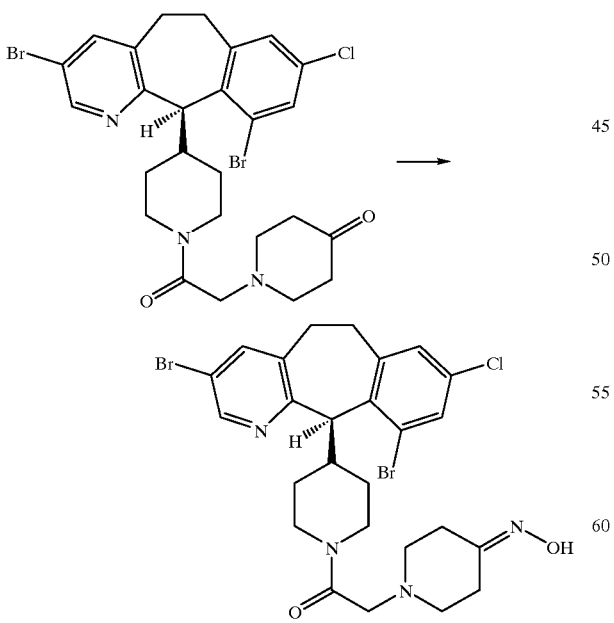

Following the procedure of Example 12, but using the product of Example 4 instead of the product of Example 1,
and chromatograph on silica gel using dichloromethane (saturated with ammonia)-methanol (97%–3%) to obtain the product as a white solid mp=147.2–152.2° C.

EXAMPLE 15

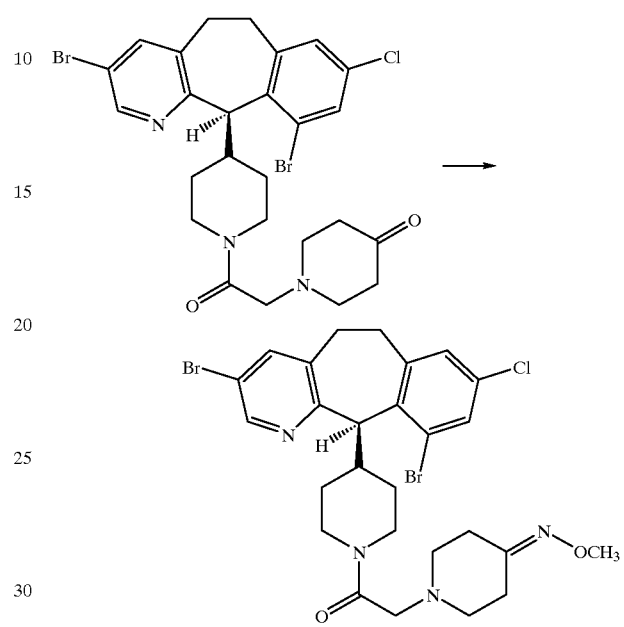

Following the procedure of Example 12, but using the product of Example 4 instead of the product of Example 1, and using methoxyamine hydrochloride instead of hydroxylamine hydrochloride, and chromatograph on silica gel using dichloromethane-methanol (98%–2%) to obtain the product as a white solid mp=105.5–108.8° C.

EXAMPLE 16

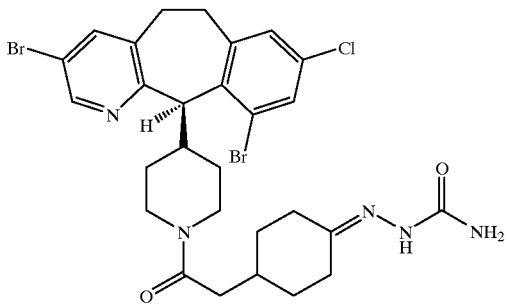

Following the procedure of Example 12, but using semicarbazide hydrochloride instead of hydroxylamine hydrochloride, and ethanol instead of pyridine, and chromatograph on silica gel using dichloromethane-methanol (96%–4%) to obtain the product as a white solid mp=167.2–169.4° C.

EXAMPLE 17

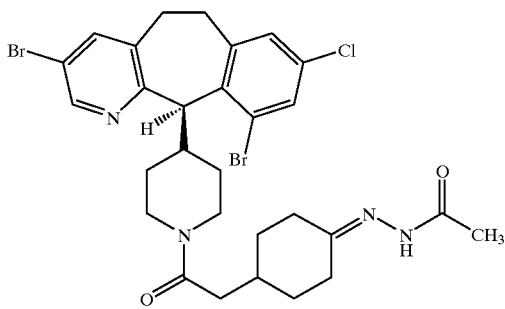

Following the procedure of Example 12, but using acetic hydrazide instead of hydroxylamine hydrochloride, and ethanol instead of pyridine, and chromatograph on silica gel using dichloromethane-methanol (95%–5%) to obtain the product as a white solid mp=152.5–155.5° C.

EXAMPLE 18

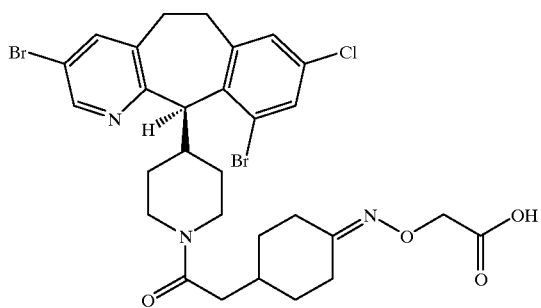

Following the procedure of Example 12, but using carboxymethoxylamine hemihydrochloride instead of hydroxylamine hydrochloride, and ethanol instead of pyridine, and chromatograph on silica gel using dichloromethane-methanol (containing a trace of acetic acid) (95%–5%) to obtain the product as a white solid mp=95.7–97.3° C.

EXAMPLE 19

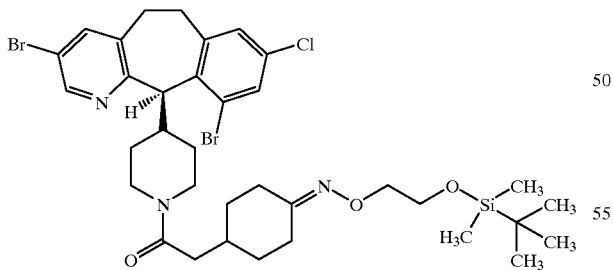

Dissolve 0.1 g (0.16 mmol) of the product of Example 12 in 5 mL of dry DMF. Cool to 0° C. under nitrogen and add 9.7 mg (0.242 mmol) of sodium hydride (60% in mineral oil) and stir for 0.5 hr. Add dropwise 0.045 g (0.189 mmol)2-tert-butyldimethylsilyoxybromoethane (freshly passed through alumina) and stir reaction at 0° C. for 0.5 hr. Add 20 mL of water then 25 mL of saturated, aqueous sodium bicarbonate solution. Extract with three 25 mL portions of dichloromethane. Dry the combined organic layers over magnesium sulfate and concentrate under vacuum. Chromatograph the crude material by preparative silica gel TLC using ethyl acetate-hexane (90%–10%) to give the product as a white solid mp=87.2°–90.3° C.

EXAMPLE 20

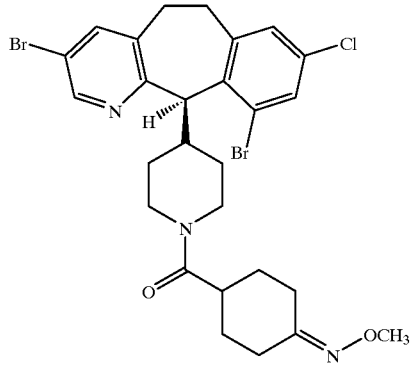

Following the procedure of Example 12, but using the product of Example 6 instead of the product of Example 1 and methoxylamine hydrochloride instead of hydroxylamine hydrochloride, and ethanol instead of pyridine, and chromatograph on silica gel using dichloromethane(saturated with ammonia)-methanol (95%–5%) to obtain the product as a white solid mp=120.4–123.8° C.

EXAMPLE 21

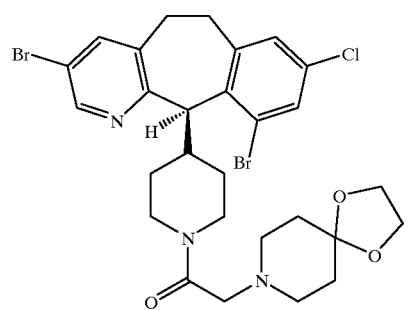

Dissolve 0.05 g (0.0819 mmol) of the product of Example 4 and 0.15 mL of ethylene glycol in 1.5 mL of acetic acid at 60° C. then cool to 35° C. and add 0.1 mL of boron trifluoride diethyl etherate and stir at 25° C. for 2.5 hr. Add 15 mL of water and extract with two 30 mL portions of ether. Dry organic layers over magnesium sulfate and concentrate under vacuum. Chromatograph the residue on silica gel using 100% dichloromethane followed by dichloromethane-methanol 97%–3% to obtain 0.036 g of the product as a white solid mp=130.2–134.9° C.

EXAMPLE 22

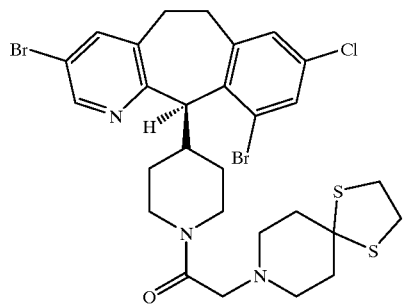

Follow the procedure of Example 21, but use 1,2-ethanedithiol instead of ethylenegylcol to obtain the product as a white solid mp=135.8–138.5° C.

EXAMPLE 23

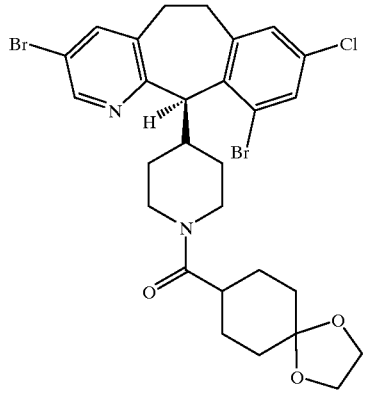

Dissolve 120 mg (0.2 mmol) of the product of Example 6 in 10 mL of toluene containing 14 mg (0.07 mmol) of 4-toluenesulfonic acid and reflux for 1 hr. Add 1 mL of toluene and 2 mL of ethylene glycol. Reflux for 3 hr using a Dean Stark water separator. Add 10 mL of aqueous, saturated sodium bicarbonate solution and extract with two 50 mL portions of ethyl acetate. Dry the combined organic layers over magnesium sulfate and concentrate under vacuum. Chromatograph the residue on silica gel using ethyl acetate-dichloromethane (70%–30%) to give 80 mg of the product as a white solid mp=119.3–121.6° C.

EXAMPLES 24–27

Reaction of the tricyclic amine

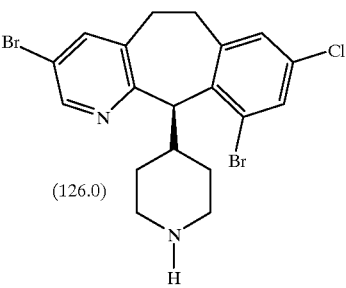

(126.0)

with the reagents and carboxylic acids listed in Table 8 provides compounds of the formula

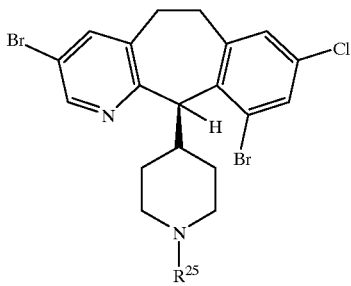

wherein $R^{25}$ is defined in Table 8. The formula number of the carboxylic acids used refers to the acids:

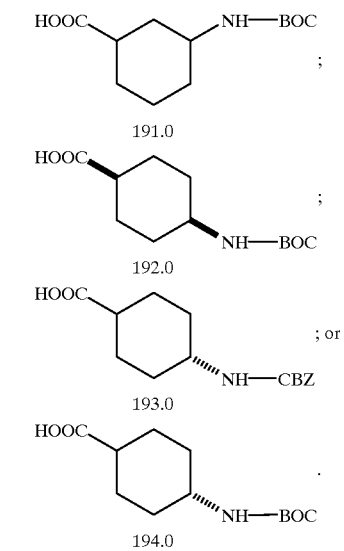

The formula numbers for the $R^{25}$ substituent refer to the substituents:

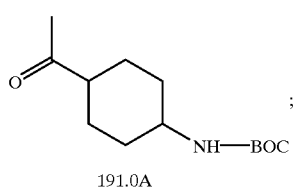

191.0A

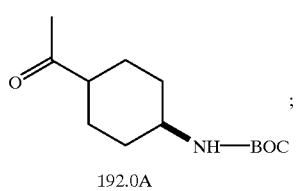

192.0A

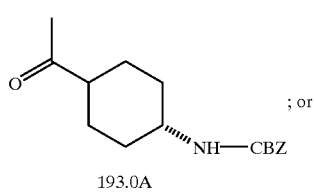

193.0A

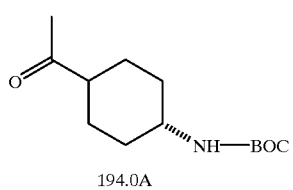

194.0A

TABLE 8

| Ex. | Stereo-chemistry | Reaction Conditions | R²⁵ and mp (° C.) |
|---|---|---|---|
| 24 | 1,3-trans racemic | 191.0 + 126.0, DEC.HCl/-NMM/HOBT.H₂O/DMF 20-30° C. | 191.0A white solid 139.0–140.9 |
| 25 | 1,4-cis | 192.0 + 126.0, DEC.HCl/-NMM/HOBT.H₂O/DMF 20-30° C. | 192.0A white solid 127.1–132.2 |
| 26 | 1,4-trans | 193.0 + 126.0, DEC.HCl/-NMM/HOBT.H₂O/DMF 20-30° C. | 193.0A white solid 139.0–140.9 heating 2–3° C./min. |
| 27 | 1,4-trans | 194.0 + 126.0, DEC.HCl/-NMM/HOBT.H₂O/DMF 20-30° C. | 194.0A white solid 134.7–144.7 heating 2–3° C./min. |

EXAMPLE 28

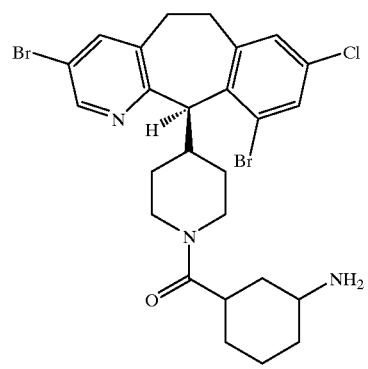

The product of Example 24 is reacted with TFA in $CH_2Cl_2$ at a temperature of about 20–30° C. to afford the the compound as a 1,3-trans racemic mixture. The compound was obtained as an off white solid having a mp of 134.5–137.7° C.

EXAMPLE 29

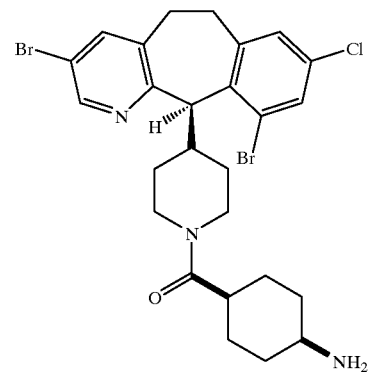

Follow the procedure of Example 28, but use the product of Example 25 to obtain the 1,4-cis compound as a white solid having a mp of 125.8–129.4° C.

EXAMPLE 30

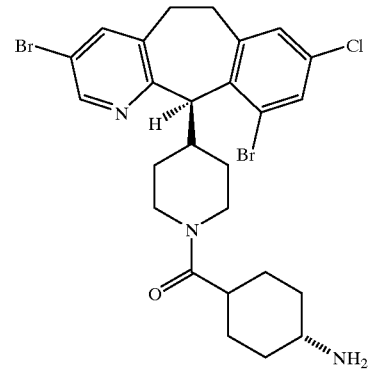

React the product of Example 27 with 10% (v/v) H₂SO₄ in dioxane to obtain the 1,4-trans compound as as a white solid having a mp of 188.3–190.7° C. (heating 2–3° C./min.).
EXAMPLES 31–41
Use the compound, reagents and conditions indicated in Table 9 to obtain the compound of the formula:
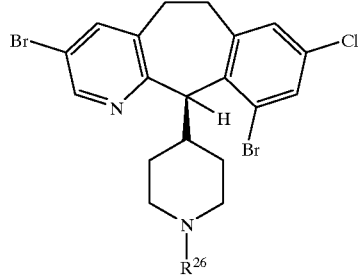
wherein $R^{26}$ is defined in Table 9. The formula numbers in Table 9 refer to:
195.0
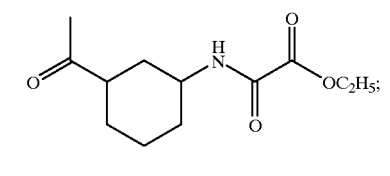
196.0
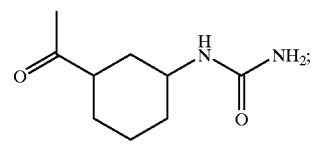
196.0
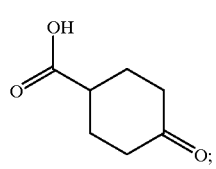
197.0
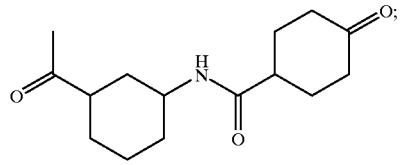
(198.0)
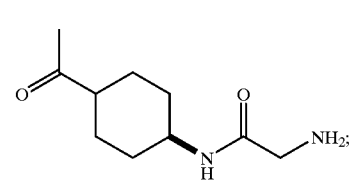
(199.0)
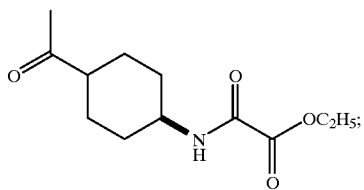
(200.0)
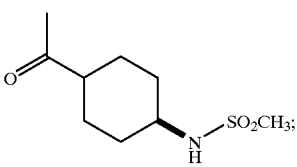
(201.0)
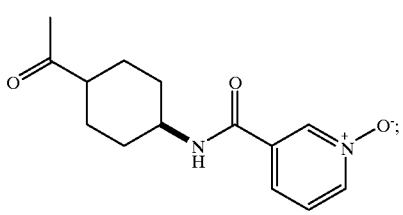
(202.0)
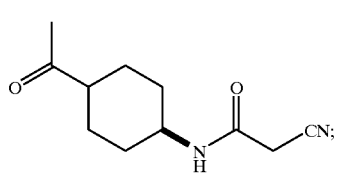
(203.0)
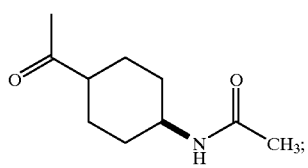
(204.0)
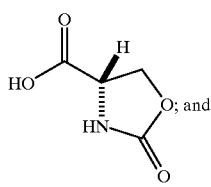
(205.0)
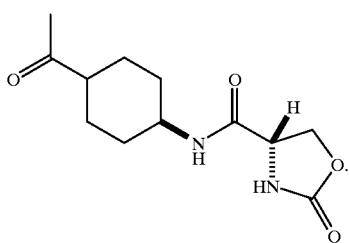

TABLE 9

| Ex. | Stereo-chemistry | Reaction Conditions | $R^{26}$ and mp (° C.) |
|---|---|---|---|
| 31 | 1,3-trans racemic | Product of Ex. 28/ethyl oxalyl chloride/Et$_3$N/-CH$_2$Cl$_2$ 20–30° C. | 195.0 white solid 141.6–143.9 |
| 32 | 1,3-trans racemic | Product of Ex. 28/TMS-NCO/CH$_2$Cl$_2$ 20–30° C. | 196.0 white solid 151.9–153.4 |
| 33 | 1,3-trans racemic | 196.0/Ex. 28/DEC.HCl/-NMM/HOBT.H$_2$O/DMF 20–30° C. | 197.0 white solid 145.5–146.9 |
| 34 | 1,4-cis | Product of Ex. 29/TMS-NCO/CH$_2$Cl$_2$ 20–30° C. | 198.0 white solid 183.9–185.8 |
| 35 | 1,4-cis | Product of Ex. 29/ethyl oxalyl chloride/Et$_3$N/-CH$_2$Cl$_2$ 20–30° C. | 199.0 white solid 134.0–135.5 |
| 36 | 1,4-cis | Product of Ex. 29/-ClSO$_2$CH$_3$/Et$_3$N/CH$_2$Cl$_2$ 20–30° C. | 200.0 white solid 131.1–133.4 |
| 37 | 1,4-cis | Product of Ex. 29/-nicotinic acid N-oxide/-DEC.HCl/NMM/-HOBT.H$_2$O/DMF 20–30° C. | 201.0 white solid 173.3–174.9 |
| 38 | 1,4-cis | CNCH$_2$C(O)OH/Product of Ex. 29/DEC.HCl/NMM/-HOBT.H$_2$O/DMF 20–30° C. | 202.0 white solid 160.9–162.4 |
| 39 | 1,4-cis | Product of Ex. 29/acetyl chloride/Et$_3$N/CH$_2$Cl$_2$ 20–30° C. | 203.0 white solid 147.2–150.0 |
| 40 | 1,4-cis | 204.0/Product of Ex. 29/-DEC.HCl/NMM/-HOBT.H$_2$O/DMF 20–30° C. | 205.0 white solid 192.1–195.2 |
| 41 | 1,4-trans | Product of Ex. 29/ethyl oxalyl chloride/Et$_3$N/-CH$_2$Cl$_2$ 20–30° C. | 199.0 white solid [a]$D^{22.0°}$= +39.7, c = 0.0013 CH$_2$Cl$_2$ |

ASSAYS

FPT IC$_{50}$ (inhibition of farnesyl protein transferase, in vitro enzyme assay) and COS Cell IC$_{50}$ (Cell-Based Assay) were determined following the assay procedures described in WO 95/10516, published Apr. 20, 1995. GGPTs IC$_{50}$ (inhibition of geranylgeranyl protein transferase, in vitro enzyme assay), Cell Mat Assay, and anti-tumor activity (in vivo anti-tumor studies) could be determined by the assay procedures described in WO 95/10516. The disclosure of WO 95/10516 is incorporated herein by reference thereto.

Additional assays can be carried out by following essentially the same procedure as described above, but with substitution of alternative indicator tumor cell lines in place of the T24-BAG cells. The assays can be conducted using either DLD-1-BAG human colon carcinoma cells expressing an activated K-ras gene or SW620-BAG human colon carcinoma cells expressing an activated K-ras gene. Using other tumor cell lines known in the art, the activity of the compounds of this invention against other types of cancer cells could be demonstrated.

Soft Agar Assay:

Anchorage-independent growth is a characteristic of tumorigenic cell lines. Human tumor cells can be suspended in growth medium containing 0.3% agarose and an indicated concentration of a farnesyl transferase inhibitor. The solution can be overlayed onto growth medium solidified with 0.6% agarose containing the same concentration of farnesyl transferase inhibitor as the top layer. After the top layer is solidified, plates can be incubated for 10–16 days at 37° C. under 5% CO$_2$ to allow colony outgrowth. After incubation, the colonies can be stained by overlaying the agar with a solution of MIT (3-[4,5-dimethylthiazol-2-yl]-2,5-diphenyltetrazolium bromide, Thiazolyl blue) (1 mg/mL in PBS). Colonies can be counted and the IC$_{50}$'s can be determined.

The results FPT IC$_{50}$ results are given in Table 10. In Table 10, "nM" represents nanomolar.

TABLE 10

| Compound | FPT IC$_{50}$ (nM) | Compound | FPT IC$_{50}$ (nM) |
|---|---|---|---|
| 13.0 | 2.2 | 14.0 | 2.6 |
| 16.0 | 16% at 160 | 17.0A | 170 |
| 17.0B | 32% at 140 | 18.0 | 5.0 |
| 19.0 | 10.7 | 20.0 | 7.0 |
| 21.0 | 10.7 | 22.0 | 4.7 |
| 23.0 | 2.7 | 24.0 | 4.7 |
| 25.0 | 4.4 | 26.0 | 6.0 |
| 27.0 | 6.7 | 28.0 | 35 |
| 29.0 | 3.0 | 30.0 | 4.3 |
| 31.0 | 1.9 | 32.0 | 97 |
| 33.0 | 5.1 | 34.0 | 10.7 |
| 35.0 | 8.2 | 36.0 | 67 |
| 37.0 | 14 | 38.0 | 6.2 |
| 39.0 | 23 | 40.0 | 2.9 |
| 42.1 | 21 | 43.0 | 150 |
| 44.0 | 13.9 | 45.0 | 17.6 |
| 46.0 | 34 | 49.1 | 15.6 |
| 68.0 | >160 | 69.0 | 7.8 |
| 70.0 | 11 | — | — |

Compound 69 had a COS IC$_{50}$ of 30 nM.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

Pharmaceutical Dosage Form Examples

EXAMPLE A

| | Tablets | | |
|---|---|---|---|
| No. | Ingredients | mg/tablet | mg/tablet |
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

| | Capsules | | |
|---|---|---|---|
| No. | Ingredient | mg/capsule | mg/capsule |
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound selected from:

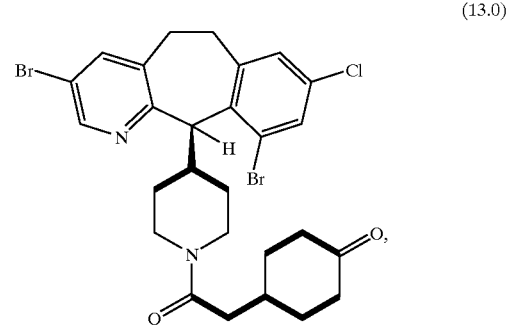

(13.0)

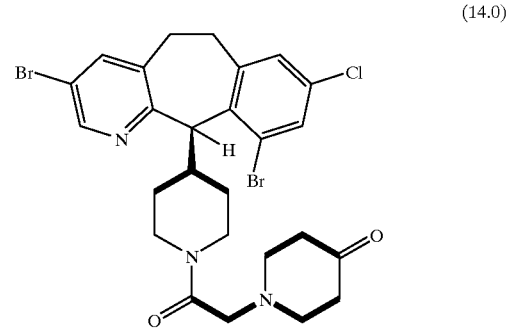

(14.0)

-continued
(17.0A)
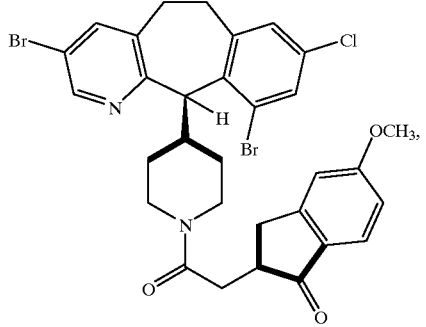
(Isomer A)
(18.0)
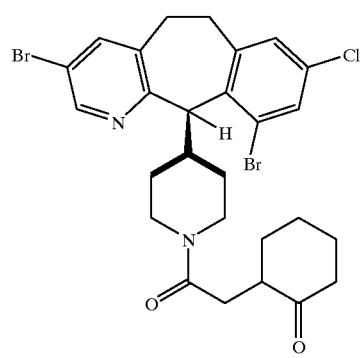
,
(19.0)
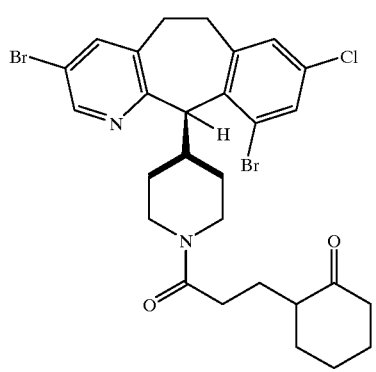
,
(20.0)
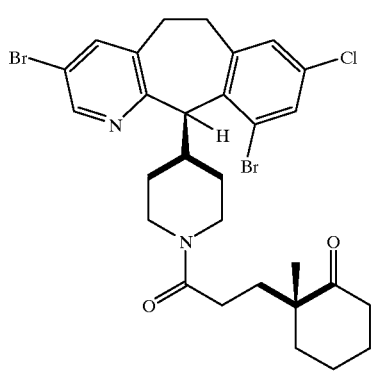
-continued
(21.0)
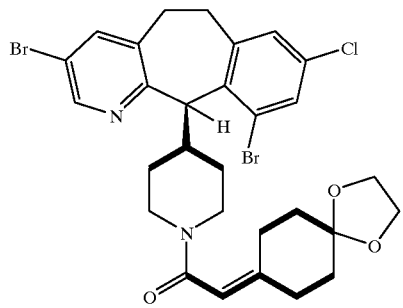
,
(22.0)
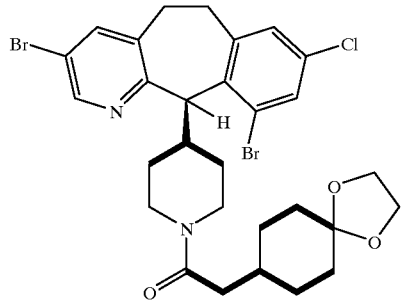
(23.0)
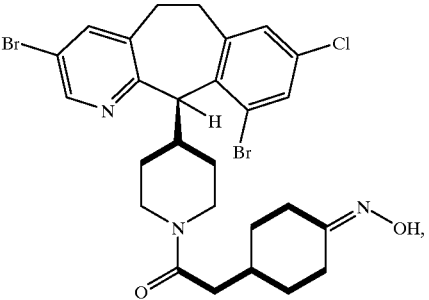
(24.0)
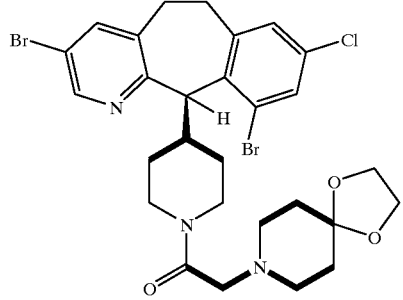
(25.0)
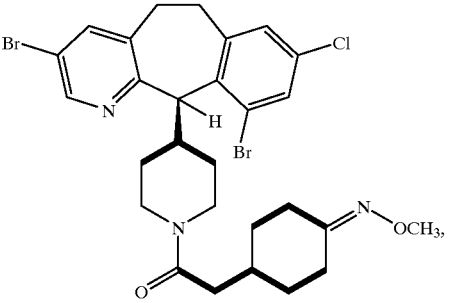

(26.0)
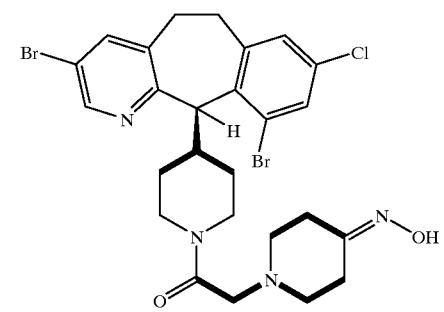
(27.0)
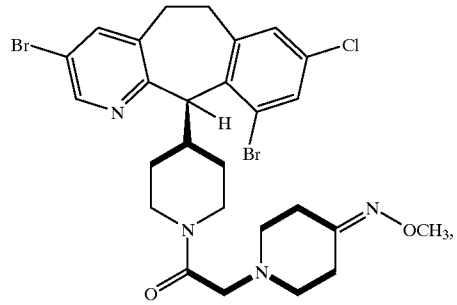
(28.0)
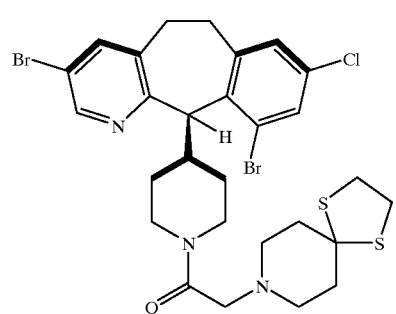
(29.0)
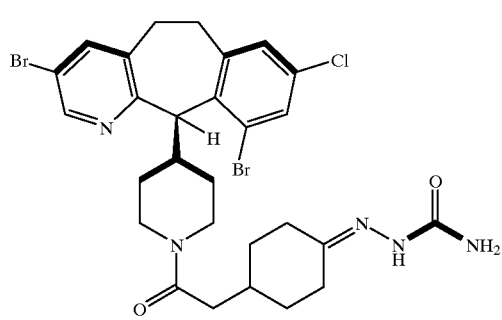
(30.0)
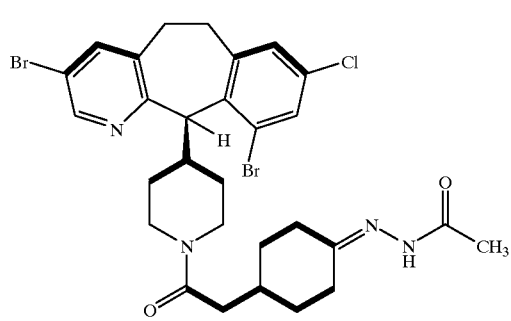
(31.0)
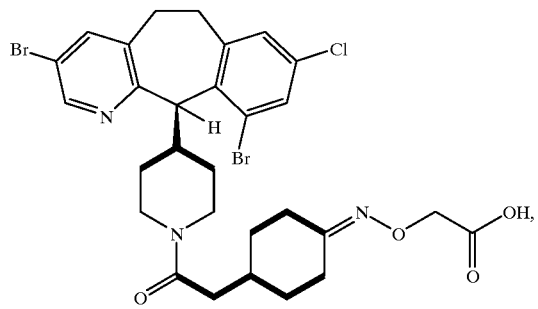
(32.0)
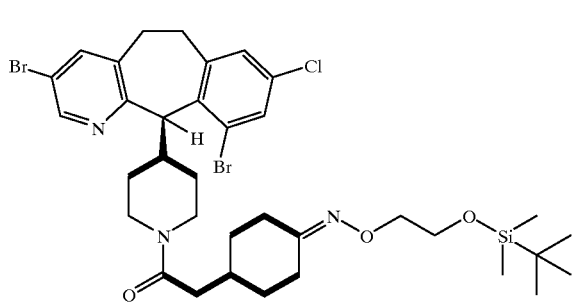
(33.0)
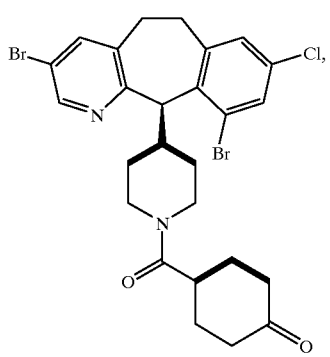
(34.0)
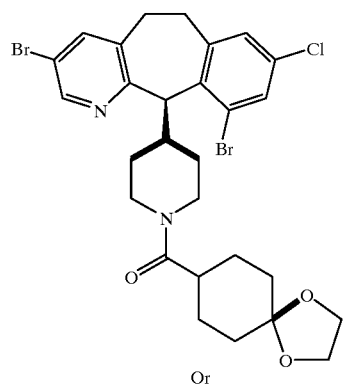
Or -continued (35.0)

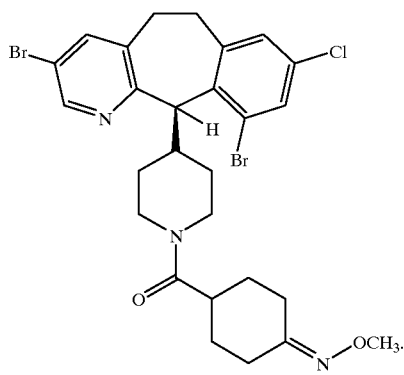

2. A compound selected from compounds of the formula:

(1.18)

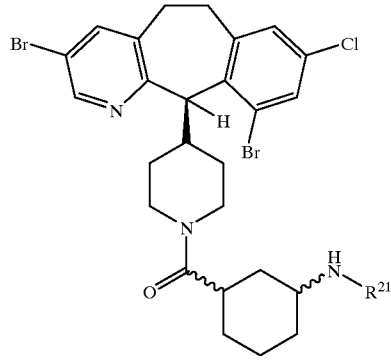

wherein R²¹ is selected from the substituents listed in Table 2:

TABLE 2

| Compound | R²¹ |
|---|---|
| 43.0 | -C(=O)-O-C(CH₃)₃ |
| 44.0 | H |
| 45.0 | -C(=O)-NH₂ |
| 46.0 | -C(=O)-C(=O)-OC₂H₅ |
| 49.1 | -C(=O)-C(=O)-NH₂ |

3. A method of inhibiting farnesyl protein transferase in tumor cells expressing an activated ras oncogene comprising administering to a human in need thereof, a farnesyl protein transferase inhibiting amount of a compound of claim 1.

4. The method of claim 3 wherein the tumor cells are pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumor cells, breast tumor cells and prostate tumor cells.

5. A pharmaceutical composition comprising an effective amount of a compound of claim 1, in combination with a pharmaceutically acceptable carrier.

6. A compound selected from:

(36.0)

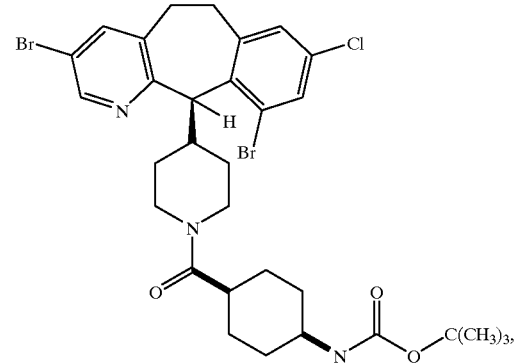

(37.0)

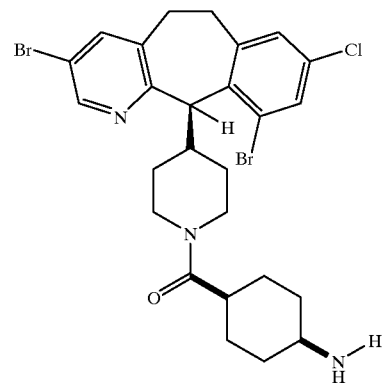

(38.0)

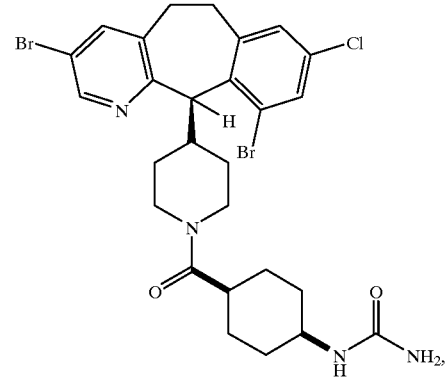

-continued
(39.0)
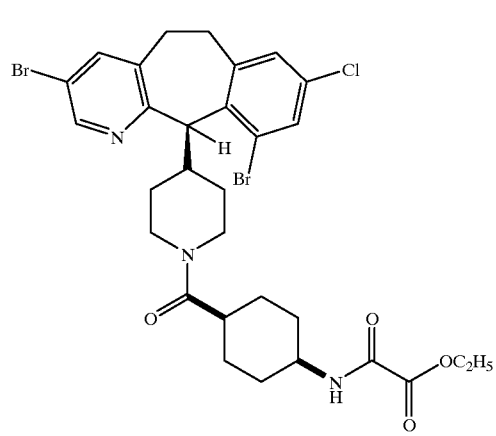
(40.0)
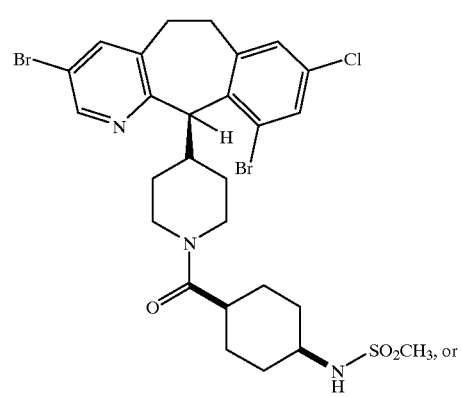
(42.1)
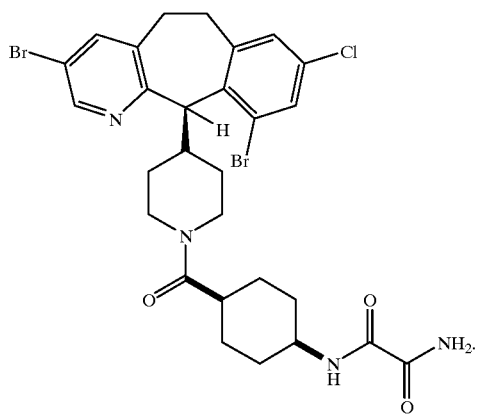
7. A compound selected from:
(68.0)
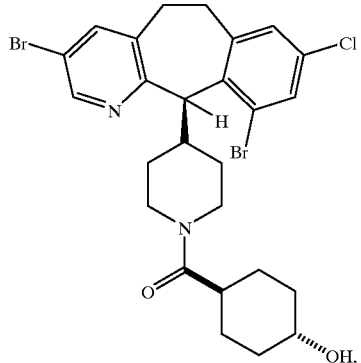
(69.0)
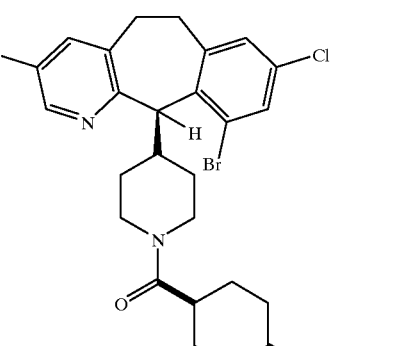
(70.0)
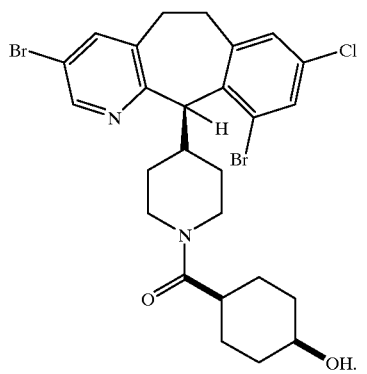
8. A method of inhibiting farnesyl protein transferase in tumor cells expressing an activated ras oncogene comprising administering a human in need thereof, a farnesyl protein transferase inhibiting amount of a compound of claim 2.

9. The method of claim 8 wherein the tumor cells are pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumor cells, breast tumor cells and prostate tumor cells.

10. A pharmaceutical composition comprising an effective amount of a compound of claim 2, in combination with a pharmaceutically acceptable carrier.

11. A method of inhibiting farnesyl protein transferase in tumor cells expressing an activated ras oncogene comprising administering to a human in need thereof, a farnesyl protein transferase inhibiting amount of a compound of claim 6.

12. The method of claim 11 wherein the tumor cells are pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumor cells, breast tumor cells and prostate tumor cells.

13. A pharmaceutical composition comprising an effective amount of a compound of claim 6, in combination with a pharmaceutically acceptable carrier.

14. A method of inhibiting farnesyl protein transferase in tumor cells expressing an activated ras oncogene comprising administering to a human in need thereof, a farnesyl protein transferase inhibiting amount of a compound of claim 7.

15. The method of claim 14 wherein the tumor cells are pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumor cells, breast tumor cells and prostate tumor cells.

16. A pharmaceutical composition comprising an effective amount of a compound of claim 7, in combination with a pharmaceutically acceptable carrier.

\* \* \* \* \*